US007396813B2

(12) United States Patent
Adang et al.

(10) Patent No.: US 7,396,813 B2
(45) Date of Patent: Jul. 8, 2008

(54) METHOD FOR INHIBITING INSECTS WITH AN INSECT CADHERIN ECTODOMAIN

(75) Inventors: Michael J. Adang, Athens, GA (US); Gang Hua, Athens, GA (US); Jiang Chen, Athens, GA (US); Mohd Amir Fursan Abdullah, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 42 days.

(21) Appl. No.: 11/040,472

(22) Filed: Jan. 21, 2005

(65) Prior Publication Data

US 2005/0283857 A1    Dec. 22, 2005

Related U.S. Application Data

(60) Provisional application No. 60/538,715, filed on Jan. 22, 2004.

(51) Int. Cl.
*A01N 37/18* (2006.01)
*C12N 15/82* (2006.01)

(52) U.S. Cl. .......................................... 514/2; 800/279
(58) Field of Classification Search ....................... None
See application file for complete search history.

(56) References Cited

U.S. PATENT DOCUMENTS

| 5,712,248 | A | 1/1998 | Kalman et al. |
| 6,423,502 | B2 | 7/2002 | Bulla |
| 6,455,266 | B1 | 9/2002 | Bulla |

FOREIGN PATENT DOCUMENTS

WO    WO 01/34807    5/2001

OTHER PUBLICATIONS

Lazar et al, 1988, Mol. Cell. Biol. 8:1247-1252.*
Hill et al, 1998, Biochem. Biophys. Res. Comm. 244:573-577.*
Guo et al, 2004, Proc. Natl. Acad. Sci. USA 101: 9205-9210.*
Abdullah, M.A.F., et al., "Enhancement of Cry19Aa mosquitocidal activity against *Aedes aegypti* by mutations . . . ," Appl. Environ. Microbiol. (2004), pp. 3769-3771, vol. 70.
Abdullah, M.A.F., et al., "Introduction of Culex toxicity into *Bacillus thuringiensis* Cry4Ba by protein engineering," Appl. Environ. Microbiol. (2003), pp. 5343-5353, vol. 69.
Dorsch, J.A., et al., "Cry1A toxins of *Bacillus thuringiensis* bind specifically to a region adjacent . . . ," Insect Biochem. Molec. Biol. (2002), pp. 1025-1036, vol. 32.
Francis, B.R., et al., "Further characterization of BT-R1, the cadherin-like receptor for Cry1Ab toxin . . . ," Insect Biochem. Molec. Biol. (1997), pp. 541-550, vol. 27.
Gahan, L.J., et al., "Identification of a gene associated with B.t. resistance in *Heliothis virescens*," Science (2001), pp. 857-860, vol. 293.
Gomez, B., et al., "Hydropathic complementarity determines interaction of epitope (869) HITDTNNK(876) in *Manduca sexta* . . . ," J. Biol. Chem. (2002), pp. 30137-30143, vol. 277.
Gomez, I., et al., "Molecular basis for *Bacillus thuringiensis* Cry1Ab toxin specificity: two structural determinants . . . ," Biochem. (2003), pp. 10482-10489, vol. 42.
Gomez, I., et al., "Mapping the epitope in cadherin-like receptors involved in *Bacillus thuringiensis* Cry1A toxin . . . ," J. Biol. Chem. (2001), pp. 28906-28912, vol. 276.
Gomez, I., et al., "Cadherin-like receptor binding facilitates proteolytic cleavage of helix alpha-1 in domain I and oligomer . . . ," FEBS Lett. (2002), pp. 242-246, vol. 513.
Hara, H., et al., "A cadherin-like protein functions as a receptor for *Bacillus thuringiensis* Cry1Aa and Cry1Ac toxins on midgut . . . ," FEBS Lett. (2003), pp. 29-34, vol. 538.
Hua, G., et al., "Fluorescent-based assays establish Manduca sexta Bt-R1a cadherin as a receptor for multiple . . . ," Insect Biochem. Molec. Biol. (2004), pp. 193-202, vol. 34.
Keeton, T.P. et al., "Ligand specificity and affinity of BT-R1, the *Bacillus thuringiensis* toxin receptor from . . . ," Appl. Environ. Microbiol. (1997), pp. 3419-3425, vol. 63.
Morin, S. et al., "Three cadherin alleles associated with resistance to *Bacillus thuringiensis* in pink bollworm," Proc. Natl. Acad. Sci. U.S.A. (2003), pp. 5004-5009, vol. 100.
Nagamatsu, Y., et al., "Identification of Bombyx mori midgut receptor for *Bacillus thuringiensis* insecticidal . . . ," Biosci. Biotechnol. Biochem. (1998), pp. 718-726, vol. 62.
Nagamatsu, Y., et al., "The cadherin-like protein is essential to specificity determination and cytotoxic action of the Bacillus . . . ," FEBS Lett. (1999), pp. 385-390, vol. 460.
Tsuda, Y., et al., "Cytotoxic activity of *Bacillus thuringiensis* Cry proteins on mammalian cells transfected with cadherin-like . . . ," Biochem. J. (2003), pp. 697-703, vol. 369.
Vadlamudi, R.K., et al., "A specific binding protein from Manduca sexta for the insecticidal toxin of Bacillus . . . ," J. Biol. Chem. (1993), pp. 12334-12340, vol. 268.
Vadlamudi, R.K., et al., "Cloning and expression of a receptor for an insecticidal toxin of *Bacillus thuringiensis*," J. Biol. Chem. (1995), pp. 5490-5494, vol. 270.
Xie, R., et al., "Single amino acid mutations in the cadherin receptor from H.v. affects its toxin binding ability to Cry1A . . . ," J. Biol. Chem. (2005), pp. 8416-8425, vol. 280.

* cited by examiner

*Primary Examiner*—Anne Kubelik
(74) *Attorney, Agent, or Firm*—Saliwanchik, Lloyd & Saliwanchik

(57) ABSTRACT

The subject invention pertains to the use of peptide fragments of cadherins (including cadherin-like proteins). The subject invention includes a cell (and use thereof) comprising a polynucleotide that expresses the peptide fragment. The subject invention includes methods of feeding the peptides to insects. In preferred embodiments, the peptides are fed to target insects together with one or more insecticidal proteins, preferably (but not limited to) *B.t.* Cry proteins. When used in this manner, the peptide fragment can not only enhance the apparent toxin activity of the Cry protein against the insect species that was the source of the receptor but also against other insect species. Preferably, the cadherin is a *Bacillus thuringiensis* (*B.t.*) insecticidal crystal protein (Cry) toxin receptor. Preferably, the peptide fragment is a binding domain of the receptor. In some preferred embodiments, the peptide is the binding domain nearest to the membrane proximal ectodomain. Corresponding domains are identifiable in a variety of *B.t.* toxin receptors.

15 Claims, 20 Drawing Sheets

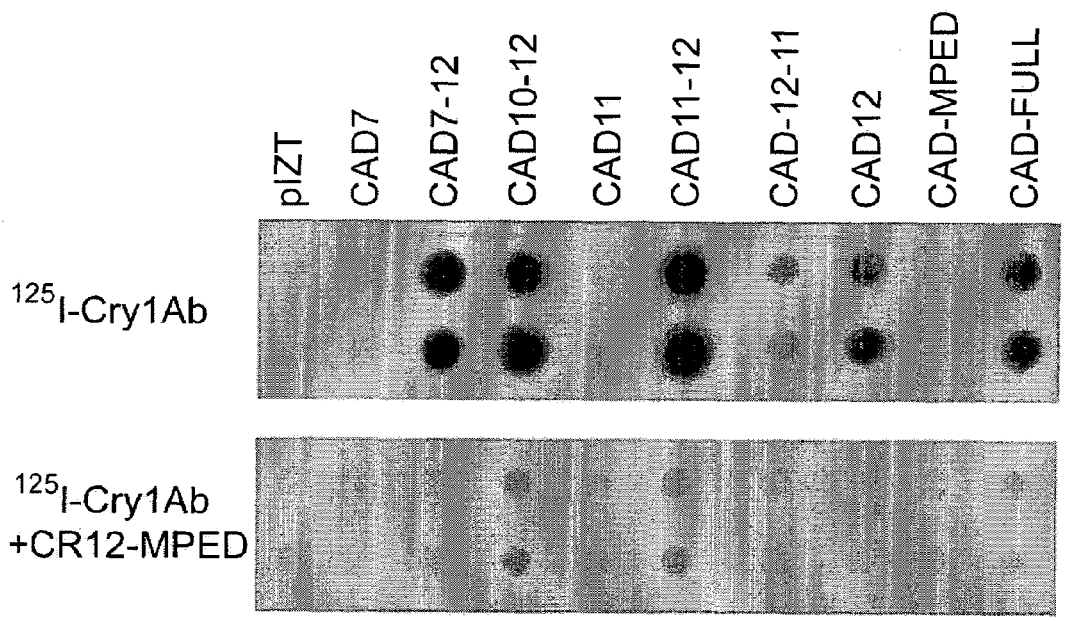

Fig. 2

MHHHHHHSSGLVPRGSGMKETAAAKFERQHMDSPDLGTDDDDKAMGISTA
6x His-tag    thrombin    S-tag    enterokinase   Ms-cad 1362
          digestion site

DSIGRELLRLHATQSEGAAITYAIDYDTMVVDPSLEAVRQSAFVLNAQTG

VLTLNIQPTATMHGLFKFEVTATDTAGAQDRTDVTVYVVSSQNRVYFVF

VNTLQQVEDNRDFIADTFSAGFNMTCNIDQVVPANDPVTGVALEHSTQM

RGHFIRDNVPVLADEIEQIRSDLVLLSSIQTTLAARSLVLQDLLTNSSPDSA

PARAPPPPPLRSGC (SEQ ID NO:14)
Ms-cad 1567

*P. xyostella*

Fig. 5E

**Bioassay of Cry1A toxins on *Plutella xylostella* (R)**

| Cry1Aa | Cry1Aa: CR12-MPED (1:100) | Cry1Ab | Cry1Ab: CR12-MPED (1:100) |

| Cry1Ac | Cry1Ac: CR12-MPED (1:100) | Control | CR12-MPED (100) |

Fig. 5F

Bioassay of Cry1A toxins on *Manduca sexta*

| Cry1Aa | Cry1Aa: CR12-MPED (1:1) | Cry1Aa: CR12-MPED (1:10) | Cry1Aa: CR12-MPED (1:100) |
| Cry1Ab | Cry1Ab: CR12-MPED (1:1) | Cry1Ab: CR12-MPED (1:10) | Cry1Ab: CR12-MPED (1:100) |
| Cry1Ac | Cry1Ac: CR12-MPED (1:1) | Cry1Ac: CR12-MPED (1:10) | Cry1Ac: CR12-MPED (1:100) |
| Control ($H_2O$) | CR12-MPED (1) | CR12-MPED (10) | CR12-MPED (100) |

Fig. 6A

Bioassay of Cry1A toxins on *Heliothis virescens*

| Cry1Aa | Cry1Aa: CR12-MPED (1:1) | Cry1Aa: CR12-MPED (1:10) | Cry1Aa: CR12-MPED (1:100) |
|---|---|---|---|

| Cry1Ac | Cry1Ac: CR12-MPED (1:1) | Cry1Ac: CR12-MPED (1:10) | Cry1Ac: CR12-MPED (1:100) |
|---|---|---|---|

| Control (H$_2$O) | Control (Tris) | CR12-MPED (100) | CR12-MPED (100) |
|---|---|---|---|

Fig. 6B

Bioassay of Cry1A toxins on *Helicoverpa zea*

| Cry1Aa | Cry1Aa:<br>CR12-MPED<br>(1:1) | Cry1Aa:<br>CR12-MPED<br>(1:1) | Cry1Aa:<br>CR12-MPED<br>(1:1) |
|---|---|---|---|

| Cry1Ab | Cry1Ab:<br>CR12-MPED<br>(1:1) | Cry1Ab:<br>CR12-MPED<br>(1:1) | Cry1Ab:<br>CR12-MPED<br>(1:1) |
|---|---|---|---|

| Cry1Ac | Cry1Ac:<br>CR12-MPED<br>(1:1) | Cry1Ac:<br>CR12-MPED<br>(1:10) | Cry1Ac:<br>CR12-MPED<br>(1:10) |
|---|---|---|---|

| Control<br>(H$_2$O) | Control<br>(Tris) | CR12-MPED<br>(100) | CR12-MPED<br>(100) |
|---|---|---|---|

Fig. 6C

Bioassay of Cry1A toxins on *Spodoptera frugiperda*

Cry1Aa | Cry1Aa: CR12-MPED (1:1) | Cry1Aa: CR12-MPED (1:10) | Cry1Aa: CR12-MPED (1:100)

Cry1Ab | Cry1Ab: CR12-MPED (1:1) | Cry1Ab: CR12-MPED (1:10) | Cry1Ab: CR12-MPED (1:100)

Cry1Ac | Cry1Ac: CR12-MPED (1:1) | Cry1Ac: CR12-MPED (1:10) | Cry1Ac: CR12-MPED (1:100)

Control ($H_2O$) | CR12-MPED (100)

Fig. 6D

**Bioassay of Cry1A toxins on *Plutella xylostella* (S)**

| Cry1Aa | Cry1Aa: CR12-MPED (1:100) | Cry1Ab | Cry1Ab: CR12-MPED (1:100) |
| Cry1Ac | Cry1Ac: CR12-MPED (1:100) | Control (H$_2$O) | CR12-MPED (100) |

Fig. 6E

**Bioassay of Cry1A toxins on *Plutella xylostella* (R)**

| Cry1Aa | Cry1Aa: CR12-MPED (1:100) | Cry1Ab | Cry1Ab: CR12-MPED (1:100) |

| Cry1Ac | Cry1Ac: CR12-MPED (1:100) | Control | CR12-MPED (100) |

Fig. 6F

Enhancing effect of BtB$_2$ on Cry1Ab toxicity to *Manduca sexta* Larvae

Fig. 7

Bioassay of Cry1Ac with Cadherin fragments on Soybean looper larvae

SEQUENCE LISTING

<160> NUMBER OF SEQ ID NOS: 13

<210> SEQ ID NO 1
<211> LENGTH: 618
<212> TYPE: DNA
<213> ORGANISM: Manduca sexta

<400> SEQUENCE: 1

```
gggatatcca cagcggactc catcggcaga gagctgctca gattacatgc gacccagtct      60
gaaggcgcgg ccattactta tgctatagac tacgataaca tggtagtgga ccccagcctg     120
gaggcagtga gacagtcggc tttcgtactg aacgctcaaa ccggagtgct gacgcttaat     180
atccagccca cggccacgat gcatggactg ttcaaattcg aagtcacagc tactgacacg     240
gccggcgctc aggaccgcac cgacgtcacc gtgtacgtgg tatcctcgca gaaccgcgtc     300
tacttcgtgt tcgtcaacac gctgcaacag gtcgaagaca acagagactt tatcgcggac     360
accttcagcg ctgggttcaa catgacctgc aacatcgacc aagtggtgcc cgccaacgac     420
cccgtcaccg gcgtggcgct ggagcacagc acgcagatgc gcggccactt catacggac     480 aacgtacccg tactcgctga tgagatagaa cagatccgta gtgacctagt cctcctgagc     540
tcgatacaaa caacgctggc ggcgcgatcg ctggtgttgc aggacttgtt gaccaactcc     600
agcccggact cggcgcct                                                   618
```

<210> SEQ ID NO 2
<211> LENGTH: 206
<212> TYPE: PRT
<213> ORGANISM: Manduca sexta

<400> SEQUENCE: 2

```
Gly Ile Ser Thr Ala Asp Ser Ile Gly Arg Glu Leu Leu Arg Leu His
  1               5                  10                  15
Ala Thr Gln Ser Glu Gly Ala Ala Ile Thr Tyr Ala Ile Asp Tyr Asp
                 20                  25                  30
Thr Met Val Val Asp Pro Ser Leu Glu Ala Val Arg Gln Ser Ala Phe
             35                  40                  45
Val Leu Asn Ala Gln Thr Gly Val Leu Thr Leu Asn Ile Gln Pro Thr
 50                  55                  60
Ala Thr Met His Gly Leu Phe Lys Phe Glu Val Thr Ala Thr Asp Thr
 65                  70                  75                  80
Ala Gly Ala Gln Asp Arg Thr Asp Val Thr Val Tyr Val Val Ser Ser
                 85                  90                  95
Gln Asn Arg Val Tyr Phe Val Phe Val Asn Thr Leu Gln Gln Val Glu
                100                 105                 110
Asp Asn Arg Asp Phe Ile Ala Asp Thr Phe Ser Ala Gly Phe Asn Met
                115                 120                 125
Thr Cys Asn Ile Asp Gln Val Val Pro Ala Asn Asp Pro Val Thr Gly
130                 135                 140
Val Ala Leu Glu His Ser Thr Gln Met Arg Gly His Phe Ile Arg Asp
145                 150                 155                 160
Asn Val Pro Val Leu Ala Asp Glu Ile Glu Gln Ile Arg Ser Asp Leu
                165                 170                 175
Val Leu Leu Ser Ser Ile Gln Thr Thr Leu Ala Ala Arg Ser Leu Val
                180                 185                 190
Leu Gln Asp Leu Leu Thr Asn Ser Ser Pro Asp Ser Ala Pro
                195                 200                 205
```

<210> SEQ ID NO 3
<211> LENGTH: 975
<212> TYPE: DNA
<213> ORGANISM: Manduca sexta

<400> SEQUENCE: 3

```
gcgtcctcag aacatgctgt cgctttcata gaaaagagtg ccggcatgga agagtctcac        60
caacttcctc tagcacaaga catcaagaac catctctgtg aagacgactg tcacagcatt       120
tactatcgta ttatcgatgg caacagcgag ggtcatttcg gcctggatcc tgttcgcaac       180
aggttgttcc tgaagaaaga gctgataaga aacaaagtg cctcccacac tctgcaagtg        240
gcggctagta actcgcccga tggtggcatt ccacttcctg cttccatcct tactgtcact       300
gttaccgtga gggaggcaga ccctcgtcca gtgtttatga gggaattgta caccgcaggg       360
atatccacag cggactccat cggcagagag ctgctcagat acatgcgac ccagtctgaa        420
ggcgcggcca ttacttatgc tatagactac gatacaatgg tagtggaccc cagcctggag       480
gcagtgagac agtcggcttt cgtactgaac gctcaaaccg gagtgctgac gcttaatatc       540
cagcccacgg ccacgatgca tggactgttc aaattcgaag tcacagctac tgacacggcc       600
ggcgctcagg accgcaccga cgtcaccgtg tacgtggtat cctcgcagaa ccgcgtctac       660
ttcgtgttcg tcaacacgct gcaacaggtc gaagacaaca gagactttat cgcggacacc       720
ttcagcgctg ggttcaacat gacctgcaac atcgaccaag tggtgcccgc aaacgacccc       780
gtcaccggcg tggcgctgga gcacagcacg cagatgcgcg gccacttcat acgggacaac       840
gtaccccgtac tcgctgatga gatagaacag atccgtagtg acctagtcct cctgagctcg       900
```

```
atacaaacaa cgctggcggc gcgatcgctg gtgttgcagg acttgttgac caactccagc    960
ccggactcgg cgcct                                                     975
```

<210> SEQ ID NO 4
<211> LENGTH: 324
<212> TYPE: PRT
<213> ORGANISM: Manduca sexta

<400> SEQUENCE: 4

```
Ser Ser Glu His Ala Val Ala Phe Ile Glu Lys Ser Ala Gly Met Glu
1               5                   10                  15

Glu Ser His Gln Leu Pro Leu Ala Gln Asp Ile Lys Asn His Leu Cys
            20                  25                  30

Glu Asp Asp Cys His Ser Ile Tyr Tyr Arg Ile Asp Gly Asn Ser
        35                  40                  45

Glu Gly His Phe Gly Leu Asp Pro Val Arg Asn Arg Leu Phe Leu Lys
    50                  55                  60

Lys Glu Leu Ile Arg Glu Gln Ser Ala Ser His Thr Leu Gln Val Ala
65                  70                  75                  80

Ala Ser Asn Ser Pro Asp Gly Gly Ile Pro Leu Pro Ala Ser Ile Leu
                85                  90                  95

Thr Val Thr Val Thr Val Arg Glu Ala Asp Pro Arg Pro Val Phe Met
            100                 105                 110

Arg Glu Leu Tyr Thr Ala Gly Ile Ser Thr Ala Asp Ser Ile Gly Arg
        115                 120                 125

Glu Leu Leu Arg Leu His Ala Thr Gln Ser Glu Gly Ala Ala Ile Thr
    130                 135                 140

Tyr Ala Ile Asp Tyr Asp Thr Met Val Val Asp Pro Ser Leu Glu Ala
145                 150                 155                 160

Val Arg Gln Ser Ala Phe Val Leu Asn Ala Gln Thr Gly Val Leu Thr
                165                 170                 175

Leu Asn Ile Gln Pro Thr Ala Thr Met His Gly Leu Phe Lys Phe Glu
            180                 185                 190

Val Thr Ala Thr Asp Thr Ala Gly Ala Gln Asp Arg Thr Asp Val Thr
        195                 200                 205

Val Tyr Val Val Ser Ser Gln Asn Arg Val Tyr Phe Val Phe Val Asn
    210                 215                 220

Thr Leu Gln Gln Val Glu Asp Asn Arg Asp Phe Ile Ala Asp Thr Phe
225                 230                 235                 240

Ser Ala Gly Phe Asn Met Thr Cys Asn Ile Asp Gln Val Val Pro Ala
                245                 250                 255

Asn Asp Pro Val Thr Gly Val Ala Leu Glu His Ser Thr Gln Met Arg
            260                 265                 270

Gly His Phe Ile Arg Asp Asn Val Pro Val Leu Ala Asp Glu Ile Glu
        275                 280                 285

Gln Ile Arg Ser Asp Leu Val Leu Leu Ser Ser Ile Gln Thr Thr Leu
    290                 295                 300

Ala Ala Arg Ser Leu Val Leu Gln Asp Leu Leu Thr Asn Ser Ser Pro
305                 310                 315                 320

Asp Ser Ala Pro
```

<210> SEQ ID NO 5
<211> LENGTH: 819
<212> TYPE: DNA
<213> ORGANISM: Manduca sexta

<400> SEQUENCE: 5

```
gttgacaacg gggagtggca tctcatcatc acgcaaagac aggattacga gttgcccggc    60
atgcagcagt acatgttcaa tgtgcgcgtg gacggccagt cgctggtggc aggcgtgtct   120
ctcgctatcg tcaacataga tgacaacgcg cccatcatac aaaacttcga gccttgccgg   180
gttcctgaac tgggcgagcc agggttgaca gaatgcacat accaagtatc ggacgcggac   240
ggacggatca gtacagagtt catgacgttc aggatcgaca gcgttcgtgg cgacgaggag   300
accttctaca tcgaacggac gaatatcccc aaccaatgga tgtggctaaa tatgaccttg   360
ggcgttaata cctcgctcaa cttcgtcacc agtccgctgc atatattcag cgtgacagcc   420
ctggactcgc tcccgaacac ccacacggtg actatgatgg tgcaagtggc gaatgtgaac   480
agccgtccgc cgcgctggct ggagatcttc gctgtccaac agtttgaaga gaaatcttac   540
caaaacttca cagtgagggc gatcgacgga gacactgaga tcaatatgcc tatcaactac   600
aggctgatca caaatgagga agacacattc ttcagcatcg aggccctgcc tggtggaaaa   660
agcggggcta tattccacgt gtcaccaatt gaccgcgaca cactgcaacg agaggtgttt   720
ccacttacga tcgtcgctta caaatacgat gaggaagctt tctccacatc aacaaacgtg   780
gtcatcattg tgacagacat caacgaccaa agacctgaa                          819
```

<210> SEQ ID NO 6
<211> LENGTH: 273
<212> TYPE: PRT
<213> ORGANISM: Manduca sexta

<400> SEQUENCE: 6

```
Val Asp Asn Gly Glu Trp His Leu Ile Ile Thr Gln Arg Gln Asp Tyr
  1               5                  10                  15

Glu Leu Pro Gly Met Gln Gln Tyr Met Phe Asn Val Arg Val Asp Gly
             20                  25                  30

Gln Ser Leu Val Ala Gly Val Ser Leu Ala Ile Val Asn Ile Asp Asp
         35                  40                  45

Asn Ala Pro Ile Ile Gln Asn Phe Glu Pro Cys Arg Val Pro Glu Leu
     50                  55                  60

Gly Glu Pro Gly Leu Thr Glu Cys Thr Tyr Gln Val Ser Asp Ala Asp
 65                  70                  75                  80

Gly Arg Ile Ser Thr Glu Phe Met Thr Phe Arg Ile Asp Ser Val Arg
                 85                  90                  95

Gly Asp Glu Glu Thr Phe Tyr Ile Glu Arg Thr Asn Ile Pro Asn Gln
            100                 105                 110

Trp Met Trp Leu Asn Met Thr Leu Gly Val Asn Thr Ser Leu Asn Phe
        115                 120                 125

Val Thr Ser Pro Leu His Ile Phe Ser Val Thr Ala Leu Asp Ser Leu
    130                 135                 140

Pro Asn Thr His Thr Val Thr Met Met Val Gln Val Ala Asn Val Asn
145                 150                 155                 160

Ser Arg Pro Pro Arg Trp Leu Glu Ile Phe Ala Val Gln Gln Phe Glu
                165                 170                 175

Glu Lys Ser Tyr Gln Asn Phe Thr Val Arg Ala Ile Asp Gly Asp Thr
            180                 185                 190

Glu Ile Asn Met Pro Ile Asn Tyr Arg Leu Ile Thr Asn Glu Glu Asp
        195                 200                 205

Thr Phe Phe Ser Ile Glu Ala Leu Pro Gly Gly Lys Ser Gly Ala Ile
```

```
             210                 215                 220
Phe His Val Ser Pro Ile Asp Arg Asp Thr Leu Gln Arg Glu Val Phe
225                 230                 235                 240

Pro Leu Thr Ile Val Ala Tyr Lys Tyr Asp Glu Glu Ala Phe Ser Thr
                245                 250                 255

Ser Thr Asn Val Val Ile Ile Val Thr Asp Ile Asn Asp Gln Arg Pro
            260                 265                 270

Glu

<210> SEQ ID NO 7
<211> LENGTH: 5646
<212> TYPE: DNA
<213> ORGANISM: Anopheles gambiae

<400> SEQUENCE: 7
atggaacaga atcgctcaac cgataagcta cagatggaaa tactcaagcg aaccgtctgc      60
cggctcaaac cgtcggccca ccggtgccta ttggccggat ctcattcctt cacgcagcta     120
gtgctctgcc tcatcctaag cgccaccctg gtcagctgca accgtgcgcc agtgtttctg     180
atcgacgatc atgcggaaat agttatacga ttgagggagt ccccgagac gcccgtgggg      240 acgctgatct accggctgcg tgggtacgat gcggatggcg atccgcttac ctttggcgtg     300
cagaagagtg ccgacagcca catcataaga ctgaaacaga cacttccag cgaagcgttc      360 gtctacctca ccacgagct cgaccgggag gcacgcgaag agtacacgct catcctcacg     420
ctcaccgatg ggcggctcgg tgagggtaac ttcgtgacgc agagcttcct gctgctggtg     480
gaagatatca cgataatga gccgatcttt aaaccgttcg cctctgtgct ggaggtagcg     540
gaggacagtc cgccggggat tttgaccacg ctggaggccg tcgataagga cgagggtgcg     600
tacgggcagg tcgtgtacta catccaaggg ttaagcgagg agaacaacgt gttttcgatc     660
tccacttcca atgggaaggg tgtggtacgg ctggcccgag cgctggacta cgagcggcaa     720
catttctatc acatcaatgt gctggcagtg gaccgggcga tacaggggag gatcaacact     780
ggaactgcag cactgctcgt gagagtgaag gacgtgaggg accagccgcc cgagtttctg     840
gtaacgcaac cggtggtacg aatatccgag gatgctccaa ttggaacgga agtgattgcg     900
aggatgatct attctctttc aacagtcaaa gctgtggatg tgatcgagg aattaataat     960 cgaattattt acgggatttc aaacaacggc agtgaactgt ttgagattga tcggttgaag    1020
ggttcactgc gaacgaaaca gaagctcgac agggaggact ccacgaatcc catcaacggt    1080
gctttcatac tggaagtggt tgcgattgaa gagagcaagc tacagcctgc gccttcctca    1140
acaatggaga tcaccgtgat cgtgacggat gtgaacgacg aaataccacg cttccgaagc    1200
gacggctatg agtgtgagat tggcgagaac gcacaggaga acacgctggc ccggttcatc    1260
gacggcagca tcaacgaggt gttttgactac gatcagggta aaaatggcac gtttcgactg    1320
tcgctccatc cgccgagtga catcttcgag gtgattccaa agcgagcgat caacgaggcc    1380
acattcgggt tgcgtgtgaa ggatccgtcc atgctcgatt acgagcgggt tcgggagctg    1440
tccctcacag tggtggcgag tgaggttgag tccgctggtc gtaccagtac cgcccagata    1500
cgggtggtcg tgctgatca aacgataac tttcccgagt tttcacagcc cgtctacgac      1560
attgatgtac cggagaatgt gatagccggt acggtgttgt tgcagctaca agcaacggat    1620
agtgattcgg gcctgttcgg cacggagggt gtacggtacg cgaacctgac tggtagtatc    1680
tcgagctttc tccatctgga tccacacgct ggcacggtga cacttatggc atcggagagt    1740
```

```
cccgtgtttg atcgtgaaat catccaaaag cactacctct cggtggaggc ccgtgataat    1800
ggcggtcggg gcaatcggaa cacggtgcca ctgatactga acgtgctcga tgtgaacgac    1860
aatgccccag tgtttgtgca gaagcggtac gaggtgagac tgaaggagaa tgcgtttgag    1920
tttgagtccc cgatcgtggt ggaagcgcgt gacagcgacc tagaaggctc gccgaacagt    1980
gcggtagagt atcggttgat tggtgctcac cattccgact acttccatgt ggataggcgc    2040
acgggaagac tctcagtgcg tgaagcagtt gactttgaac ggttggaaag tagtggcggt    2100
agtggtgaca cgcgaaccat tgcacttacc attgaggcgg cggatggtgg ggagccaccg    2160
ctgactgccc aggtcgaggt gacggtgtac gtgcaggacg tgaacgatta tgcgcccgtt    2220
tttctggagt cacagtacgc gatcgtcata ccggaggaca cgccgagcgg gttgcccgtg    2280
ctgcgcgtga ccgcgatgga tggagatggg tcttttccca acaaccacgt cacgtaccgg    2340
atacagcagg gtggtgatgg taggttcgta ataggagcta gtacaggcga gatatcgatc    2400
acgcacggtg catcgctgga tccgaatctg ctcgcgcccg atgcgctggg ctcggggtca    2460
acgtacgtgc tggaggtgtt cgctaccgat ggtggcaatg gagatcagca gctgcaagga    2520
tcctgtctgg tgaacaatac gcccgtcggc accgaagtgt accggctgat ggccaccgat    2580
ccggacgagg gtgcaatgct gcggtactac atcgatcgaa gcctatcgga gggcaagact    2640
gaggagggtg cactggtgaa gctggacgat tatgactttg cggcggcctt catactgaac    2700
gaaacgaatg gactgctcaa gatagcaaag ctgctggatc gcgaaaagat tgccgaaatc    2760
aagctggcct gtgtggtgga ggacgtagcg gccgagcggg gtgaccagat ggcaaacacc    2820
ttcctcaaga tcaccgtgct cgacgagaac gacaacaatc ccaagttccg caaaccgttc    2880
tacaaacact ccattgcgga aaacagtcag tacggtgtgg cggtatgtac ggtggtggcc    2940
gaagatgccg atcagaacaa aacggtcaag tacagcttgg aaggggagaa gggtgtgctg    3000
gagttgctgc acgttgatga cgagacgggg gagattgtgg tgcgcaatcg gatcgatcat    3060
gaggagtaca gttggttgaa cttctcggta cgggcggctg atacgggcac gccgccgaga    3120
gcgtcctttg tggaggtgtt cgtgcaggtg ctggatgaga acgacaacaa tccttacttt    3180
gtggacagcg tgaacgatta ctacgtgtcg gagaatgcaa gcgtgggagc ggagatagcg    3240
atcatactgg cgaaggatct agattcgggg gatttcggac gcatcacgta catactggat    3300
cgtgttagct cgaaggagaa gtttagcatt gatccggaga aaggaatact acgagtagcg    3360
ggagcattgg atcgggaaga gacagctgag tatatgttgg cagtagaggc atgggataac    3420
tatccttacg gctatctcaa cggtgaaagc cgcaacgctt taaacacat actgatacac     3480 gtgctggacg acaatgacaa cgttcccgtg atccagaaac cttccgggtg tagtatgatc    3540
accgagtacc acaacatcaa cgatccgatc gtgaagctgc gggcaaccga tgcggacgac    3600
ccaaccaatg gaaacggtca actgagcttc gacattgtgg acccctcggg gatattctac    3660
atccagcagg tgtcggccca gtacgcagaa atatattccc gcgggccgct aaagaatctg    3720
cacggcaact acacgctgga gctgatagtg agcgatcttg gcggcgtacc gaacacggcc    3780
cgagagtcgg tggacatctg tgtgacggat ttcaacgacc atgcgccagt gtttgttgtc    3840
cccagtggaa atacaactgt gaaggtgttt gagaacacaa cgctcggtaa gccgttcttt    3900
caagtgcacg cgtacgatga agatgtcggc gaaaatgcga ttgtgcgcta ccgactgaag    3960
atggacacga tggcaacttt cgcaagtttt cccctcgaca aggagacggg cgagcttagc    4020
ctcgctgcgc ctctcgatcg cgagcagcag atgatgtacg atctgcgcat cgaagcgtac    4080
gatcagggta taccgacgcc gctcagcagt acggtcgatc tgatcgtgta cgtgcgggac    4140
```

```
gtcaacgaca atctacctca gtttttgctc aaggaaatca gtcttaactt tacggagcac      4200
atgacaccgg gcacggaaag aatacgcctg cccgacacgg tcgaccagga ctatctggac      4260
ccgctggacg gtccggcggc gagtgtggtt tgctactaca tcgtgcacgg caacgaggat      4320
ggacactttg gactggatcc agtgtcacac gatctaacgg tggagaaaga gctcgatcgg      4380
gagaaaaaat ctctgtacaa gctgcacatt aaggcgacgg aggagtgcac gaacgcgaat      4440
ctatcgttgg acacgaccag tcactcgggc aatctcctaa aggctactgt gtacataaac      4500
gacatcaacg acaactcgcc agtgtttgag tcgaaaatat tcaccggcgg tatctcaacg      4560
tcgtcgctgt tcggtgccac aattcttcag ctgcaggcca cggacgaaga cgatggattg      4620
aacggattgg ttcggtacta tcggcacggc gaggtgcgga aaacgcttgc cgaggggttg      4680
gacgatttgc gcagcgatcc gttcctggtc gaggcggaca cgggccaagt gttgctgaac      4740
tttttccccc agaagtcgat gcgcggctac tttgactttt ccgtgctggc gaacgattcg      4800
tacggctgcc atgatcgggc gcacgtgttc atctatctga tacgggagga tcagcgggta      4860
aagtttatac tgcgccaacg gccgtccgag attcgtcaca acattcaaag ttttcgcgag      4920
atcttgagca atgtgagtgg atgcatcgtg aacattgacg atatacgggt gcacgagaat      4980
ccggacggtt cggttgatag gaccaagagc gacatgttta tgcatctggt cgatcagaag      5040
aacaactccg tgctggaggt acatcaggtg ctgcagttgc tggatacgca cgtggaaaag      5100
cttgatcgac tgtttaagga attcaacgtc ttggacactc aagcgtcgga gctggtccaa      5160
acggcagaga tggacgagct gtccgtcaac ataaatatgg cgtttgtgac caacattttg      5220
ctcggcgcgc tgctgatcgt tgtaatagga ctgtcgatct cacagcgttt atcctaccgc      5280
agacagctac gggcagcgaa gatagctgcc tttggctcca cgggtcctag tcgcatgtat      5340
caggaagtgc tcggcgccgt accgaacacg aacaagcaca gcatgaaggg cagcaacccg      5400
atctggatcg gcagcggcac accggagggc gaatgggcga aggacgagtt cgacaagtgc      5460
aaggatgcga tcgacgcaca gtacgaacga tcgctcagct cgggcttctt catcgacaac      5520
tgtctgcagt acgaggcacg gaagggtttc gccggggccg aagcgaacaa cgccgccaac      5580
tatcagctca gcgggacag cgagacgacg ctgtgcgccc ggaacttgga aacgaccgaa      5640
ctgtaa                                                                 5646
```

<210> SEQ ID NO 8
<211> LENGTH: 1881
<212> TYPE: PRT
<213> ORGANISM: Anopheles gambiae

<400> SEQUENCE: 8

```
Met Glu Gln Asn Arg Ser Thr Asp Lys Leu Gln Met Glu Ile Leu Lys
1               5                   10                  15

Arg Thr Val Cys Arg Leu Lys Pro Ser Ala His Arg Cys Leu Leu Ala
            20                  25                  30

Gly Ser His Ser Phe Thr Gln Leu Val Leu Cys Leu Ile Leu Ser Ala
        35                  40                  45

Thr Leu Val Ser Cys Asn Arg Ala Pro Val Phe Leu Ile Asp Asp His
    50                  55                  60

Ala Glu Ile Val Ile Arg Leu Arg Glu Phe Pro Glu Thr Pro Val Gly
65                  70                  75                  80

Thr Leu Ile Tyr Arg Leu Arg Gly Tyr Asp Ala Asp Gly Asp Pro Leu
                85                  90                  95
```

```
Thr Phe Gly Val Gln Lys Ser Ala Asp Ser His Ile Ile Arg Leu Lys
            100                 105                 110

Gln Asn Thr Ser Ser Glu Ala Phe Val Tyr Leu Asn His Glu Leu Asp
        115                 120                 125

Arg Glu Ala Arg Glu Glu Tyr Thr Leu Ile Leu Thr Leu Thr Asp Gly
    130                 135                 140

Arg Leu Gly Glu Gly Asn Phe Val Thr Gln Ser Phe Leu Leu Leu Val
145                 150                 155                 160

Glu Asp Ile Asn Asp Asn Glu Pro Ile Phe Lys Pro Phe Ala Ser Val
                165                 170                 175

Leu Glu Val Ala Glu Asp Ser Pro Pro Gly Ile Leu Thr Thr Leu Glu
            180                 185                 190

Ala Val Asp Lys Asp Glu Gly Ala Tyr Gly Gln Val Val Tyr Tyr Ile
        195                 200                 205

Gln Gly Leu Ser Glu Glu Asn Asn Val Phe Ser Ile Ser Thr Ser Asn
    210                 215                 220

Gly Lys Gly Val Val Arg Leu Ala Arg Ala Leu Asp Tyr Glu Arg Gln
225                 230                 235                 240

His Phe Tyr His Ile Asn Val Leu Ala Val Asp Arg Ala Ile Gln Gly
                245                 250                 255

Arg Ile Asn Thr Gly Thr Ala Ala Leu Leu Val Arg Val Lys Asp Val
            260                 265                 270

Glu Asp Gln Pro Pro Glu Phe Leu Val Thr Gln Pro Val Val Arg Ile
        275                 280                 285

Ser Glu Asp Ala Pro Ile Gly Thr Glu Val Ile Ala Arg Met Ile Tyr
    290                 295                 300

Ser Leu Ser Thr Val Lys Ala Val Asp Gly Asp Arg Gly Ile Asn Asn
305                 310                 315                 320

Arg Ile Ile Tyr Gly Ile Ser Asn Asn Gly Ser Glu Leu Phe Glu Ile
                325                 330                 335

Asp Arg Leu Lys Gly Ser Leu Arg Thr Lys Gln Lys Leu Asp Arg Glu
            340                 345                 350

Asp Ser Thr Asn Pro Ile Asn Gly Ala Phe Ile Leu Glu Val Val Ala
        355                 360                 365

Ile Glu Glu Ser Lys Leu Gln Pro Ala Pro Ser Ser Thr Met Glu Ile
    370                 375                 380

Thr Val Ile Val Thr Asp Val Asn Asp Glu Ile Pro Arg Phe Arg Ser
385                 390                 395                 400

Asp Gly Tyr Glu Cys Glu Ile Gly Glu Asn Ala Gln Glu Asn Thr Leu
                405                 410                 415

Ala Arg Phe Ile Asp Gly Ser Ile Asn Glu Val Phe Tyr Asp Gln
            420                 425                 430

Gly Lys Asn Gly Thr Phe Arg Leu Ser Leu His Pro Pro Ser Asp Ile
        435                 440                 445

Phe Glu Val Ile Pro Lys Arg Ala Ile Asn Glu Ala Thr Phe Gly Leu
    450                 455                 460

Arg Val Lys Asp Pro Ser Met Leu Asp Tyr Glu Arg Val Arg Glu Leu
465                 470                 475                 480

Ser Leu Thr Val Val Ala Ser Glu Val Glu Ser Ala Gly Arg Thr Ser
                485                 490                 495

Thr Ala Gln Ile Arg Val Val Val Leu Asp Gln Asn Asp Asn Phe Pro
            500                 505                 510

Glu Phe Ser Gln Pro Val Tyr Asp Ile Asp Val Pro Glu Asn Val Ile
```

-continued

```
             515                 520                 525
Ala Gly Thr Val Leu Leu Gln Leu Gln Ala Thr Asp Ser Asp Ser Gly
        530                 535                 540
Leu Phe Gly Thr Glu Gly Val Arg Tyr Ala Asn Leu Thr Gly Ser Ile
545                 550                 555                 560
Ser Ser Phe Leu His Leu Asp Pro His Ala Gly Thr Val Thr Leu Met
                565                 570                 575
Ala Ser Glu Ser Pro Val Phe Asp Arg Glu Ile Ile Gln Lys His Tyr
            580                 585                 590
Leu Ser Val Glu Ala Arg Asp Asn Gly Gly Arg Gly Asn Arg Asn Thr
        595                 600                 605
Val Pro Leu Ile Leu Asn Val Leu Asp Val Asn Asp Asn Ala Pro Val
    610                 615                 620
Phe Val Gln Lys Arg Tyr Glu Val Arg Leu Lys Glu Asn Ala Phe Glu
625                 630                 635                 640
Phe Glu Ser Pro Ile Val Val Glu Ala Arg Asp Ser Asp Leu Glu Gly
                645                 650                 655
Ser Pro Asn Ser Ala Val Glu Tyr Arg Leu Ile Gly Ala His His Ser
            660                 665                 670
Asp Tyr Phe His Val Asp Arg Arg Thr Gly Arg Leu Ser Val Arg Glu
        675                 680                 685
Ala Val Asp Phe Glu Arg Leu Glu Ser Ser Gly Gly Ser Gly Asp Thr
    690                 695                 700
Arg Thr Ile Ala Leu Thr Ile Glu Ala Ala Asp Gly Gly Glu Pro Pro
705                 710                 715                 720
Leu Thr Ala Gln Val Glu Val Thr Val Tyr Val Gln Asp Val Asn Asp
                725                 730                 735
Tyr Ala Pro Val Phe Leu Glu Ser Gln Tyr Ala Ile Val Ile Pro Glu
            740                 745                 750
Asp Thr Pro Ser Gly Leu Pro Val Leu Arg Val Thr Ala Met Asp Gly
        755                 760                 765
Asp Gly Ser Phe Pro Asn Asn His Val Thr Tyr Arg Ile Gln Gln Gly
    770                 775                 780
Gly Asp Gly Arg Phe Val Ile Gly Ala Ser Thr Gly Glu Ile Ser Ile
785                 790                 795                 800
Thr His Gly Ala Ser Leu Asp Pro Asn Leu Leu Ala Pro Asp Ala Leu
                805                 810                 815
Gly Ser Gly Ser Thr Tyr Val Leu Glu Val Phe Ala Thr Asp Gly Gly
            820                 825                 830
Asn Gly Asp Gln Gln Leu Gln Gly Ser Cys Leu Val Asn Asn Thr Pro
        835                 840                 845
Val Gly Thr Glu Val Tyr Arg Leu Met Ala Thr Asp Pro Asp Glu Gly
    850                 855                 860
Ala Met Leu Arg Tyr Tyr Ile Asp Arg Ser Leu Ser Glu Gly Lys Thr
865                 870                 875                 880
Glu Glu Gly Ala Leu Val Lys Leu Asp Asp Tyr Asp Phe Ala Ala Ala
                885                 890                 895
Phe Ile Leu Asn Glu Thr Asn Gly Leu Leu Lys Ile Ala Lys Leu Leu
            900                 905                 910
Asp Arg Glu Lys Ile Ala Glu Ile Lys Leu Ala Cys Val Val Glu Asp
        915                 920                 925
Val Ala Ala Glu Arg Gly Asp Gln Met Ala Asn Thr Phe Leu Lys Ile
    930                 935                 940
```

```
Thr Val Leu Asp Glu Asn Asp Asn Pro Lys Phe Arg Lys Pro Phe
945                 950                 955                 960

Tyr Lys His Ser Ile Ala Glu Asn Ser Gln Tyr Gly Val Ala Val Cys
            965                 970                 975

Thr Val Val Ala Glu Asp Ala Asp Gln Asn Lys Thr Val Lys Tyr Ser
        980                 985                 990

Leu Glu Gly Glu Lys Gly Val Leu Glu Leu Leu His Val Asp Asp Glu
    995                 1000                1005

Thr Gly Glu Ile Val Val Arg Asn Arg Ile Asp His Glu Glu Tyr
1010                1015                1020

Ser Trp Leu Asn Phe Ser Val Arg Ala Ala Asp Thr Gly Thr Pro
1025                1030                1035

Pro Arg Ala Ser Phe Val Glu Val Phe Val Gln Val Leu Asp Glu
1040                1045                1050

Asn Asp Asn Asn Pro Tyr Phe Val Asp Ser Val Asn Asp Tyr Tyr
1055                1060                1065

Val Ser Glu Asn Ala Ser Val Gly Ala Glu Ile Ala Ile Ile Leu
1070                1075                1080

Ala Lys Asp Leu Asp Ser Gly Asp Phe Gly Arg Ile Thr Tyr Ile
1085                1090                1095

Leu Asp Arg Val Ser Ser Lys Glu Lys Phe Ser Ile Asp Pro Glu
1100                1105                1110

Lys Gly Ile Leu Arg Val Ala Gly Ala Leu Asp Arg Glu Glu Thr
1115                1120                1125

Ala Glu Tyr Met Leu Ala Val Glu Ala Trp Asp Asn Tyr Pro Tyr
1130                1135                1140

Gly Tyr Leu Asn Gly Glu Ser Arg Asn Ala Phe Lys His Ile Leu
1145                1150                1155

Ile His Val Leu Asp Asp Asn Asp Asn Val Pro Val Ile Gln Lys
1160                1165                1170

Pro Ser Gly Cys Ser Met Ile Thr Glu Tyr His Asn Ile Asn Asp
1175                1180                1185

Pro Ile Val Lys Leu Arg Ala Thr Asp Ala Asp Pro Thr Asn
1190                1195                1200

Gly Asn Gly Gln Leu Ser Phe Asp Ile Val Asp Pro Ser Gly Ile
1205                1210                1215

Phe Tyr Ile Gln Gln Val Ser Ala Gln Tyr Ala Glu Ile Tyr Ser
1220                1225                1230

Arg Gly Pro Leu Lys Asn Leu His Gly Asn Tyr Thr Leu Glu Leu
1235                1240                1245

Ile Val Ser Asp Leu Gly Gly Val Pro Asn Thr Ala Arg Glu Ser
1250                1255                1260

Val Asp Ile Cys Val Thr Asp Phe Asn Asp His Ala Pro Val Phe
1265                1270                1275

Val Val Pro Ser Gly Asn Thr Thr Val Lys Val Phe Glu Asn Thr
1280                1285                1290

Thr Leu Gly Lys Pro Phe Phe Gln Val His Ala Tyr Asp Glu Asp
1295                1300                1305

Val Gly Glu Asn Ala Ile Val Arg Tyr Arg Leu Lys Met Asp Thr
1310                1315                1320

Met Gly Asn Phe Arg Lys Phe Ser Leu Asp Lys Glu Thr Gly Glu
1325                1330                1335
```

```
Leu Ser Leu Ala Ala Pro Leu Asp Arg Glu Gln Gln Met Met Tyr
    1340            1345                1350

Asp Leu Arg Ile Glu Ala Tyr Asp Gln Gly Ile Pro Thr Pro Leu
    1355            1360                1365

Ser Ser Thr Val Asp Leu Ile Val Tyr Val Arg Asp Val Asn Asp
    1370            1375                1380

Asn Leu Pro Gln Phe Leu Leu Lys Glu Ile Ser Leu Asn Phe Thr
    1385            1390                1395

Glu His Met Thr Pro Gly Thr Glu Arg Ile Arg Leu Pro Asp Thr
    1400            1405                1410

Val Asp Gln Asp Tyr Leu Asp Pro Leu Asp Gly Pro Ala Ala Ser
    1415            1420                1425

Val Val Cys Tyr Tyr Ile Val His Gly Asn Glu Asp Gly His Phe
    1430            1435                1440

Gly Leu Asp Pro Val Ser His Asp Leu Thr Val Glu Lys Glu Leu
    1445            1450                1455

Asp Arg Glu Lys Lys Ser Leu Tyr Lys Leu His Ile Lys Ala Thr
    1460            1465                1470

Glu Glu Cys Thr Asn Ala Asn Leu Ser Leu Asp Thr Thr Ser His
    1475            1480                1485

Ser Gly Asn Leu Leu Lys Ala Thr Val Tyr Ile Asn Asp Ile Asn
    1490            1495                1500

Asp Asn Ser Pro Val Phe Glu Ser Lys Ile Phe Thr Gly Gly Ile
    1505            1510                1515

Ser Thr Ser Ser Leu Phe Gly Ala Thr Ile Leu Gln Leu Gln Ala
    1520            1525                1530

Thr Asp Glu Asp Asp Gly Leu Asn Gly Leu Val Arg Tyr Tyr Arg
    1535            1540                1545

His Gly Glu Val Arg Lys Thr Leu Ala Glu Gly Leu Asp Asp Leu
    1550            1555                1560

Arg Ser Asp Pro Phe Leu Val Glu Ala Asp Thr Gly Gln Val Leu
    1565            1570                1575

Leu Asn Phe Phe Pro Gln Lys Ser Met Arg Gly Tyr Phe Asp Phe
    1580            1585                1590

Ser Val Leu Ala Asn Asp Ser Tyr Gly Cys His Asp Arg Ala His
    1595            1600                1605

Val Phe Ile Tyr Leu Ile Arg Glu Asp Gln Arg Val Lys Phe Ile
    1610            1615                1620

Leu Arg Gln Arg Pro Ser Glu Ile Arg His Asn Ile Gln Ser Phe
    1625            1630                1635

Arg Glu Ile Leu Ser Asn Val Ser Gly Cys Ile Val Asn Ile Asp
    1640            1645                1650

Asp Ile Arg Val His Glu Asn Pro Asp Gly Ser Val Asp Arg Thr
    1655            1660                1665

Lys Ser Asp Met Phe Met His Leu Val Asp Gln Lys Asn Asn Ser
    1670            1675                1680

Val Leu Glu Val His Gln Val Leu Gln Leu Leu Asp Thr His Val
    1685            1690                1695

Glu Lys Leu Asp Arg Leu Phe Lys Glu Phe Asn Val Leu Asp Thr
    1700            1705                1710

Gln Ala Ser Glu Leu Val Gln Thr Ala Glu Met Asp Glu Leu Ser
    1715            1720                1725

Val Asn Ile Ile Trp Leu Phe Val Thr Asn Ile Leu Leu Gly Ala
```

-continued

```
            1730                1735                1740
Leu Leu Ile Val Val Ile Gly Leu Ser Ile Ser Gln Arg Leu Ser
    1745                1750                1755

Tyr Arg Arg Gln Leu Arg Ala Ala Lys Ile Ala Ala Phe Gly Ser
    1760                1765                1770

Thr Gly Pro Ser Arg Met Tyr Gln Glu Val Leu Gly Ala Val Pro
    1775                1780                1785

Asn Thr Asn Lys His Ser Met Lys Gly Ser Asn Pro Ile Trp Ile
    1790                1795                1800

Gly Ser Gly Thr Pro Glu Gly Glu Trp Ala Lys Asp Glu Phe Asp
    1805                1810                1815

Lys Cys Lys Asp Ala Ile Asp Ala Gln Tyr Glu Arg Ser Leu Ser
    1820                1825                1830

Ser Gly Phe Phe Ile Asp Asn Cys Leu Gln Tyr Glu Ala Arg Lys
    1835                1840                1845

Gly Phe Ala Gly Ala Glu Ala Asn Asn Ala Ala Asn Tyr Gln Leu
    1850                1855                1860

Lys Arg Asp Ser Glu Thr Thr Leu Cys Ala Arg Asn Leu Glu Thr
    1865                1870                1875

Thr Glu Leu
    1880
```

<210> SEQ ID NO 9
<211> LENGTH: 639
<212> TYPE: DNA
<213> ORGANISM: Anopheles gambiae

<400> SEQUENCE: 9

```
ggtatctcaa cgtcgtcgct gttcggtgcc acaattcttc agctgcaggc cacggacgaa      60
gacgatggat tgaacggatt ggttcggtac tatcggcacg gcgaggtgcg gaaaacgctt     120
gccgagggt tggacgattt cgcagcgat ccgttcctgg tcgaggcgga cacgggccaa      180
gtgttgctga actttttccc ccagaagtcg atgcgcggct actttgactt ttccgtgctg     240
gcgaacgatt cgtacggctg ccatgatcgg gcgcacgtgt tcatctatct gatacgggag     300
gatcagcggg taaagtttat actgcgccaa cggccgtccg agattcgtca acacattcaa     360
agttttcgcg agatcttgag caatgtgagt ggatgcatcg tgaacattga cgatatacgg     420
gtgcacgaga atccggacgg ttcggttgat aggaccaaga gcgacatgtt tatgcatctg     480
gtcgatcaga gaacaactc cgtgctggag gtacatcagg tgctgcagtt gctggatacg     540
cacgtggaaa agcttgatcg actgtttaag gaattcaacg tcttggacac tcaagcgtcg     600
gagctggtcc aaacggcaga gatggacgag ctgtccgtc                           639
```

<210> SEQ ID NO 10
<211> LENGTH: 213
<212> TYPE: PRT
<213> ORGANISM: Anopheles gambiae

<400> SEQUENCE: 10

```
Gly Ile Ser Thr Ser Ser Leu Phe Gly Ala Thr Ile Leu Gln Leu Gln
1               5                   10                  15

Ala Thr Asp Glu Asp Gly Leu Asn Gly Leu Val Arg Tyr Tyr Arg
            20                  25                  30

His Gly Glu Val Arg Lys Thr Leu Ala Glu Gly Leu Asp Asp Leu Arg
        35                  40                  45
```

```
Ser Asp Pro Phe Leu Val Glu Ala Asp Thr Gly Gln Val Leu Leu Asn
 50                  55                  60

Phe Phe Pro Gln Lys Ser Met Arg Gly Tyr Phe Asp Phe Ser Val Leu
 65                  70                  75                  80

Ala Asn Asp Ser Tyr Gly Cys His Asp Arg Ala His Val Phe Ile Tyr
                 85                  90                  95

Leu Ile Arg Glu Asp Gln Arg Val Lys Phe Ile Leu Arg Gln Arg Pro
            100                 105                 110

Ser Glu Ile Arg His Asn Ile Gln Ser Phe Arg Glu Ile Leu Ser Asn
        115                 120                 125

Val Ser Gly Cys Ile Val Asn Ile Asp Asp Ile Arg Val His Glu Asn
    130                 135                 140

Pro Asp Gly Ser Val Asp Arg Thr Lys Ser Asp Met Phe Met His Leu
145                 150                 155                 160

Val Asp Gln Lys Asn Asn Ser Val Leu Glu Val His Gln Val Leu Gln
                165                 170                 175

Leu Leu Asp Thr His Val Glu Lys Leu Asp Arg Leu Phe Lys Glu Phe
            180                 185                 190

Asn Val Leu Asp Thr Gln Ala Ser Glu Leu Val Gln Thr Ala Glu Met
        195                 200                 205

Asp Glu Leu Ser Val
    210

<210> SEQ ID NO 11
<211> LENGTH: 5534
<212> TYPE: DNA
<213> ORGANISM: Anopheles gambiae

<400> SEQUENCE: 11
gggggggggg ggggtcgttg aaagctgtcc gctgcaggtg catgattaac gcggtttgac      60
cgcaggcaca cagcgttttg tttgaagtgg aaattttatc ttcttttgt cgttgtagtt     120 gttactgcgc ttcattgcat tcaaagagtg tgttaattag tgtaccggct gctggcggcc     180
ttaattaaat cgtgtgaatc acagcagcga gagaacggag aaatgaaatg tgttgctagt     240
aaatttaaca tgtggttgca cttgggttgg ttgctggggt tgctgctggt cctgttgccg     300
ttggtccgat gccaaggatg gggcgaacca cggttcgaga cgggaaatgt ggaaaatata     360
tccctcgccg catacaacga ggcgcagctt cagcaagatg tctggatggt ggaggagatg     420
gatgcaccgt tcgtgctgct ctacatcaat taccaaggac cgtccgagcc tacgatacgc     480
gagtcaccgg ccgatcttga cgcaaggcta cagctgtccg agggtggccg ctggtcgatc     540
gtaatcaatc gccggcagga ctacgaggtg catcagcgta gcagtctcat tctgctggcc     600
gtcgaatcca cggctatccc gtacgcgatc gtggtcaact tggtgaacgt gctggacaat     660
gcgcccgtca tgacgcccca aggtagctgt gagattgagg agttgcgcgg ggactttgtg     720
acggactgtc tgtttaacgt gtaccatgcg gacgggttcg aggagaatgg cattggcaat     780
tcgagcacga acgagctgtc gttcgagatc ggtgatgtgg ccggtgcgcg ggaccacttt     840
acgtacgtgc cctccacggt gaccccttcc cagccgatct acaacaagct gttcaatttg     900
aaagttttaa agcagctgga ctacaccgag aacgctatat ttaacttcat caccactgtg     960
tacgacctag accggacgca ctcttttcaag atgagtacga tcgttcaggt acgcaacgtc    1020
gatagccggc ctccgatctt tagccgaccg ttcaccagcg aacgaatcat ggaaaaggaa    1080
ccattttacg cgaccgtgat cgcaatcgac cgagacactg gactaaacaa accgatctgt    1140
```

```
tacgagctga cggctctagt cccggaatat cagaaatatt tcgaaattgg acaaactgat    1200
ggaaagctga ccgtgcaccc gattgatcga gatgcggaac agaacgagct gtacaccttt    1260
acgattgtag cgtacaagtg tcacaaccgg ctgctgaaca cctccagcga gggtgcaatc    1320
attttgctgg acaaaaatga caacattccc gaaatataca tgaagccgct tgagctggag    1380
ttttgggaaa acaccatcat ggagctgcca ttcgacgagc tcgtcattca cgatcgcgat    1440
ctcggcgaga atgcccggta cgaggtgcgg ctggccgaaa cggtagcagg cgtacagcag    1500
acagcggact cgttcaccat catccctggc aacgggtacc agcgtgtatc gttcacgatc    1560
aacatcaaca atgcgaccag cctggactat gagctgccgg agcgtcaaac gtttgtgctg    1620
cacgttaccg ctcacgaacc gatcgaaccg acgcacgaaa gcacccagcc gattacgatt    1680
cggctcaaaa actggaacga tgaggtaccg aagtttggcc gcgatgagta ccagatcagc    1740
gtgcccgaaa cgatcggagc gggcgagctg ttggcaacga tcaccgtgac cgatcgcgac    1800
atagacgatg gtattaagct gtccgcactg ggacggttgg ctgaaagttt aagcgtcacc    1860
gagctgccgg tcagtgccga gcccgagact aacctccccc tgtacgggtt cgaaatcact    1920
accaaggtgg agacatcttt cgactacgat attgcgaaag aggtgatagt gcagctgcag    1980
gctgaagata cgctgcgcac ggctaaacaa gaaagcctgc atcagatctt ctcgcagcta    2040
accatcacgg tgatagacgt gaacaataag ccgccccaaa ttacgctgcc tcgcggtacg    2100
atgcacattt tggaaaactc ggtcgccgac agtgcggtta tcattggcga ggagcagata    2160
gcacagatca tcggcacaga tcccgacacc gaggcggagc tggagtttag tatcgattgg    2220
agcaacagct acggcaccaa gagcggaatc cgggcgaagg cggaaacata cgaaaactgt    2280
ttctacatac acgaggaaaa ggtaaaccgt cagcgaacga tcggaaccat ccgtgtgaat    2340
cccacgttcc ccctggacgt cgatcacgaa atgtacgaca cactgttcct ggtcattcgg    2400
ctggtggacc ggaatcagac gatcctgccc aacacggtgg aaactgtagt ggcgatacag    2460
attgacgatg agaacgataa tgctccttac tttgacaaca gcacgctcac ggtggtacgg    2520
tcggttaagg aacgatcgga ctcgggcgta acgatcggta acatcatcgc tcacgacatt    2580
gacggaccag gaaataacga ataacgttc gcgatggaac caatcgatcc ggcccacaaa    2640
ggatggatga acattgacga caacggtacc gtaagggtgg agggcaatcg atcgatcgac    2700
tgtgacatcc cgcccatcga caaggtgcta cagaacgtaa ccatatcgga ctggaagtgg    2760
agtaactggc acgtgtttga aattgtcctg atggacacca acaacaagca gccgtatcac    2820
gatcccttcc cgaacgatgg gcaggtgtac cagtttgaga aaatacccte caatacagcc    2880 atcgtgcggg tggagggcaa agatcaggat cgcgatgtcc cgtaccatac cgtgtcgtac    2940
gagatcaact atcgggattt tccgcagctg cagcgttact tcgaggtgga cagtaccggg    3000
cgggcgtacg tgaaggaaaa caacgatctg ctcgatcgag atgcgggtct tgagagcatt    3060
atgattaaca tcgtgatgct ggataatgcg ggcggatatg acattcaaaa tcgtgtatcg    3120
acaaacatca atctcactct gctcgacatc aacgatcata cgccaaagct accggagctg    3180
gcagcggacg aactgaaggt gtcggagaac gccaagcagg gctacatcgt aaagacaccc    3240
tttgctgcac ttgacctaga tgacaagcgt acgccaaatg caaagatcaa ctactacatc    3300
gaagagatga cgccagagcc ggaaactccc ctattctcgc tagaaaatat agacgaatac    3360
aatgcggtgc caagggtggc tcaagatctg aaaggatttt acggaacgtg gacactgaaa    3420
attaaggcct gtgatcgtgg cagtgagtac gaaccaataa ttccactaac ggaagaaccg    3480
aaggacaatt gcgaaacacg cgactacgag ctgacggtgg aaccgttcaa ctacaacact    3540
```

```
cccagcatta cctacccctc ccgtagcgca cagctccgtc taaagtacga atcgctacaa    3600
aacggacgcc cgctggtcga gactaatggg tccccgttgc cgaaattcga agccatcgat    3660
gatgatggtg gcatatatgg agacgtaacg ttttcactga ccagcacaaa tgacggtgag    3720
caggaccacg aagtgttccg ggtggataaa gttgacaaca aaacgggcct gctagtgttg    3780
gaaaattcgc tcgccgtaca accgttcccg aaaaactaca gcatcaccgt gattgccagg    3840
gatggcggtg acaggcagtc ggaagccgct attcacgtcg tcttcatcaa catgacgggc    3900
gagccggcct ttctggagcc gaccttcgat acggacttta cagaaaatga agagggtcgc    3960
gatgagagac ggcagctacc gtttgccgag gatccgaaga acgcgggcct tccccgggc     4020 gctgagacga acgtgtacta tttcatcgat aagacgtacg gtaatgcgag ccatctgttt    4080
caactggacc gcgtcagcaa tgtgctgcag ctggcccagc tgctcgaccg ggaagagata    4140
ccgacgcccg aaatccgaat cgtggccacc aacaacgaaa atagcccgcc ggatacggtg    4200
ctcgaatcgt cccctcgct gctggtcgtc cgcatcaagg tgaacgatgt gaacgacaat     4260
ccgccggtgt ttcagcagcg gctgtacgcc gccggcatca ccacgaacga ccgcgtcccg    4320
aaggcactgt ttcgcgtgta cgccgaagat ccggacgagg acgaaatcat ccggtacgag    4380
ttggtgaacg ggacggcggt cggtgaaaac ctgcaaacgg acgggctgcc cttccggctc    4440
catccggaca gtggagagct aacgctgacg tccaaggtac agccgaacca gaacgggtac    4500
tatcagctca ccctgatcgc gttcgatcgg gacgatacgc acaatgatac ggtgccggcc    4560
aaggtgtaca tcgtgtcgga atcgaaccgc gtgacgttcg tgtttctgaa cagcgtcgag    4620
gagattgatc aaccggacgt gcggaagttt cttgcccaag agctgaccgg tgcgtacgaa    4680
atggaatgca acatcgacga catcgaccag acgacggcga cgacggtag acaggccggg     4740 gggtctagca gcgccctcac ggacgttcgg acccacttca tccaggacaa tcaggcggtg    4800
gaggcgagcc ggatacagca gcgatcctcg aaccggacgt tcgtcaccgt gctcaagacg    4860
acgctgcgca ctcgcggcct ctccctgcag gacgtaccgc ccctggcgac ggaagcgctg    4920
accgaggcgg acgaaacgct gcagatcatc ctgattgtgg tatcggcggc cctagccgtc    4980
ctgtgcgtga tactgttcgt ggcgttcttc atcaagatcc gcagcctaaa tcgccagctg    5040
aaggccctgt ccgcgaccga ttttgggtcg atttcgtccg agctgaatgg gaagccgacg    5100
cgcaacgtgc ccacaacgaa catcttctcg atcgagggct ccaatccggt gcttaacgat    5160
aacgagttcc gagaccggat gggtggtggt ggtggcggtg tttatgacga tctcagtcta    5220
caatcggaag aatccgactt caacgacgtg gacagggaca ttttcgcacc gaagcgaaag    5280
gagagtctta atcccgcgct cctggagcac atacgccagc gttcgctaaa cccaatggcg    5340
aacggaaccg acaagagcaa cgacggtgcg cctacctcca accataaaaa gctcgacgaa    5400
actgacgacg agctgtccca ccggttctag gcgcgtgtgta gtggtttcga tgtcgatggt    5460
tttatgtgct ggtttggtgt taattttagc tgtaaataca ttttactgtt attggatgaa    5520
aaaaaaaaaa aaaa                                                      5534
```

<210> SEQ ID NO 12
<211> LENGTH: 636
<212> TYPE: DNA
<213> ORGANISM: Anopheles gambiae

<400> SEQUENCE: 12

```
ggcatcacca cgaacgaccg cgtcccgaag gcactgtttc gcgtgtacgc cgaagatccg      60
```

-continued

```
gacgaggacg aaatcatccg gtacgagttg gtgaacggga cggcggtcgg tgaaaacctg      120
caaacggacg ggctgccctt ccggctccat ccggacagtg gagagctaac gctgacgtcc      180
aaggtacagc cgaaccagaa cgggtactat cagctcaccc tgatcgcgtt cgatcgggac      240
gatacgcaca atgatacggt gccggccaag gtgtacatcg tgtcggaatc gaaccgcgtg      300
acgttcgtgt ttctgaacag cgtcgaggag attgatcaac cggacgtgcg gaagtttctt      360
gcccaagagc tgaccggtgc gtacgaaatg gaatgcaaca tcgacgacat cgaccagacg      420
acggcgagcg acggtagaca ggccgggggg tctagcagcg ccctcacgga cgttcggacc      480
cacttcatcc aggacaatca ggcggtggag gcgagccgga tacagcagcg atcctcgaac      540
cggacgttcg tcaccgtgct caagacgacg ctgcgcactc gcggcctctc cctgcaggac      600
gtaccgcccc tggcgacgga agcgctgacc gaggcg                                636
```

<210> SEQ ID NO 13
<211> LENGTH: 1735
<212> TYPE: PRT
<213> ORGANISM: Anopheles gambiae

<400> SEQUENCE: 13

```
Met Lys Cys Val Ala Ser Lys Phe Asn Met Trp Leu His Leu Gly Trp
1               5                   10                  15

Leu Leu Gly Leu Leu Val Leu Leu Pro Leu Val Arg Cys Gln Gly
            20                  25                  30

Trp Gly Glu Pro Arg Phe Glu Thr Gly Asn Val Glu Asn Ile Ser Leu
        35                  40                  45

Ala Ala Tyr Asn Glu Ala Gln Leu Gln Gln Asp Val Trp Met Val Glu
    50                  55                  60

Glu Met Asp Ala Pro Phe Val Leu Leu Tyr Ile Asn Tyr Gln Gly Pro
65                  70                  75                  80

Ser Glu Pro Thr Ile Arg Glu Ser Pro Ala Asp Leu Asp Ala Arg Leu
                85                  90                  95

Gln Leu Ser Glu Gly Gly Arg Trp Ser Ile Val Ile Asn Arg Arg Gln
            100                 105                 110

Asp Tyr Glu Val His Gln Arg Ser Ser Leu Ile Leu Leu Ala Val Glu
        115                 120                 125

Ser Thr Ala Ile Pro Tyr Ala Ile Val Val Asn Leu Val Asn Val Leu
    130                 135                 140

Asp Asn Ala Pro Val Met Thr Ala Gln Gly Ser Cys Glu Ile Glu Glu
145                 150                 155                 160

Leu Arg Gly Asp Phe Val Thr Asp Cys Leu Phe Asn Val Tyr His Ala
                165                 170                 175

Asp Gly Phe Glu Glu Asn Gly Ile Gly Asn Ser Ser Thr Asn Glu Leu
            180                 185                 190

Ser Phe Glu Ile Gly Asp Val Ala Gly Ala Arg Asp His Phe Thr Tyr
        195                 200                 205

Val Pro Ser Thr Val Thr Pro Ser Gln Pro Ile Tyr Asn Lys Leu Phe
    210                 215                 220

Asn Leu Lys Val Leu Lys Gln Leu Asp Tyr Thr Glu Asn Ala Ile Phe
225                 230                 235                 240

Asn Phe Ile Thr Thr Val Tyr Asp Leu Asp Arg Thr His Ser Phe Lys
                245                 250                 255

Met Ser Thr Ile Val Gln Val Arg Asn Val Asp Ser Arg Pro Pro Ile
            260                 265                 270
```

```
Phe Ser Arg Pro Phe Thr Ser Glu Arg Ile Met Glu Lys Glu Pro Phe
            275                 280                 285

Tyr Ala Thr Val Ile Ala Ile Asp Arg Asp Thr Gly Leu Asn Lys Pro
        290                 295                 300

Ile Cys Tyr Glu Leu Thr Ala Leu Val Pro Glu Tyr Gln Lys Tyr Phe
305                 310                 315                 320

Glu Ile Gly Gln Thr Asp Gly Lys Leu Thr Val His Pro Ile Asp Arg
                325                 330                 335

Asp Ala Glu Gln Asn Glu Leu Tyr Thr Phe Thr Ile Val Ala Tyr Lys
                340                 345                 350

Cys His Asn Arg Leu Leu Asn Thr Ser Ser Glu Gly Ala Ile Ile Leu
            355                 360                 365

Leu Asp Lys Asn Asp Asn Ile Pro Glu Ile Tyr Met Lys Pro Leu Glu
        370                 375                 380

Leu Glu Phe Trp Glu Asn Thr Ile Met Glu Leu Pro Phe Asp Glu Leu
385                 390                 395                 400

Val Ile His Asp Arg Asp Leu Gly Glu Asn Ala Arg Tyr Glu Val Arg
                405                 410                 415

Leu Ala Glu Thr Val Ala Gly Val Gln Gln Thr Ala Asp Ser Phe Thr
            420                 425                 430

Ile Ile Pro Gly Asn Gly Tyr Gln Arg Val Ser Phe Thr Ile Asn Ile
        435                 440                 445

Asn Asn Ala Thr Ser Leu Asp Tyr Glu Leu Pro Glu Arg Gln Thr Phe
    450                 455                 460

Val Leu His Val Thr Ala His Glu Pro Ile Glu Pro Thr His Glu Ser
465                 470                 475                 480

Thr Gln Pro Ile Thr Ile Arg Leu Lys Asn Trp Asn Asp Glu Val Pro
                485                 490                 495

Lys Phe Gly Arg Asp Glu Tyr Gln Ile Ser Val Pro Glu Thr Ile Gly
            500                 505                 510

Ala Gly Glu Leu Leu Ala Thr Ile Thr Val Thr Asp Arg Asp Ile Asp
        515                 520                 525

Asp Gly Ile Lys Leu Ser Ala Leu Gly Arg Leu Ala Glu Ser Leu Ser
    530                 535                 540

Val Thr Glu Leu Pro Val Ser Ala Glu Pro Glu Thr Asn Leu Pro Leu
545                 550                 555                 560

Tyr Gly Phe Glu Ile Thr Thr Lys Val Gly Asp Ile Phe Asp Tyr Asp
                565                 570                 575

Ile Ala Lys Glu Val Ile Val Gln Leu Gln Ala Glu Asp Thr Leu Arg
            580                 585                 590

Thr Ala Lys Gln Glu Ser Leu His Gln Ile Phe Ser Gln Leu Thr Ile
        595                 600                 605

Thr Val Ile Asp Val Asn Asn Lys Pro Pro Gln Ile Thr Leu Pro Arg
    610                 615                 620

Gly Thr Met His Ile Leu Glu Asn Ser Val Ala Asp Ser Ala Val Ile
625                 630                 635                 640

Ile Gly Glu Glu Gln Ile Ala Gln Ile Ile Gly Thr Asp Pro Asp Thr
                645                 650                 655

Glu Ala Glu Leu Glu Phe Ser Ile Asp Trp Ser Asn Ser Tyr Gly Thr
            660                 665                 670

Lys Ser Gly Ile Arg Ala Lys Ala Glu Thr Tyr Glu Asn Cys Phe Tyr
        675                 680                 685

Ile His Glu Glu Lys Val Asn Arg Gln Arg Thr Ile Gly Thr Ile Arg
```

-continued

```
            690             695             700
Val Asn Pro Thr Phe Pro Leu Asp Val Asp His Glu Met Tyr Asp Thr
705             710             715             720

Leu Phe Leu Val Ile Arg Leu Val Asp Arg Asn Gln Thr Ile Leu Pro
            725             730             735

Asn Thr Val Glu Thr Val Ala Ile Gln Ile Asp Asp Glu Asn Asp
            740             745             750

Asn Ala Pro Tyr Phe Asp Asn Ser Thr Leu Thr Val Arg Ser Val
        755             760             765

Lys Glu Arg Ser Asp Ser Gly Val Thr Ile Gly Asn Ile Ile Ala His
770             775             780

Asp Ile Asp Gly Pro Gly Asn Asn Glu Ile Thr Phe Ala Met Glu Pro
785             790             795             800

Ile Asp Pro Ala His Lys Gly Trp Met Asn Ile Asp Asp Asn Gly Thr
            805             810             815

Val Arg Val Glu Gly Asn Arg Ser Ile Asp Cys Asp Ile Pro Pro Ile
            820             825             830

Asp Lys Val Leu Gln Asn Val Thr Ile Ser Asp Trp Lys Trp Ser Asn
            835             840             845

Trp His Val Phe Glu Ile Val Leu Met Asp Thr Asn Lys Gln Pro
850             855             860

Tyr His Asp Pro Phe Pro Asn Asp Gly Gln Val Tyr Gln Phe Glu Lys
865             870             875             880

Ile Pro Ser Asn Thr Ala Ile Val Arg Val Glu Gly Lys Asp Gln Asp
            885             890             895

Arg Asp Val Pro Tyr His Thr Val Ser Tyr Glu Ile Asn Tyr Arg Asp
            900             905             910

Phe Pro Gln Leu Gln Arg Tyr Phe Glu Val Asp Ser Thr Gly Arg Ala
            915             920             925

Tyr Val Lys Glu Asn Asn Asp Leu Leu Asp Arg Asp Ala Gly Leu Glu
            930             935             940

Ser Ile Met Ile Asn Ile Val Met Leu Asp Asn Ala Gly Gly Tyr Asp
945             950             955             960

Ile Gln Asn Arg Val Ser Thr Asn Ile Asn Leu Thr Leu Leu Asp Ile
            965             970             975

Asn Asp His Thr Pro Lys Leu Pro Glu Leu Ala Ala Asp Glu Leu Lys
            980             985             990

Val Ser Glu Asn Ala Lys Gln Gly Tyr Ile Val Lys Thr Pro Phe Ala
            995             1000            1005

Ala Leu Asp Leu Asp Asp Lys Arg Thr Pro Asn Ala Lys Ile Asn
    1010            1015            1020

Tyr Tyr Ile Glu Glu Met Thr Pro Glu Pro Glu Thr Pro Leu Phe
    1025            1030            1035

Ser Leu Glu Asn Ile Asp Glu Tyr Asn Ala Val Pro Arg Val Ala
    1040            1045            1050

Gln Asp Leu Lys Gly Phe Tyr Gly Thr Trp Thr Leu Lys Ile Lys
    1055            1060            1065

Ala Cys Asp Arg Gly Ser Glu Tyr Glu Pro Ile Ile Pro Leu Thr
    1070            1075            1080

Glu Glu Pro Lys Asp Asn Cys Glu Thr Arg Asp Tyr Glu Leu Thr
    1085            1090            1095

Val Glu Pro Phe Asn Tyr Asn Thr Pro Ser Ile Thr Tyr Pro Ser
    1100            1105            1110
```

-continued

```
Arg Ser Ala Gln Leu Arg Leu Lys Tyr Glu Ser Leu Gln Asn Gly
    1115                1120                1125
Arg Pro Leu Val Glu Thr Asn Gly Ser Pro Leu Pro Lys Phe Glu
    1130                1135                1140
Ala Ile Asp Asp Gly Gly Ile Tyr Gly Asp Val Thr Phe Ser
    1145                1150                1155
Leu Thr Ser Thr Asn Asp Gly Glu Gln Asp His Glu Val Phe Arg
    1160                1165                1170
Val Asp Lys Val Asp Asn Lys Thr Gly Leu Leu Val Leu Glu Asn
    1175                1180                1185
Ser Leu Ala Val Gln Pro Phe Pro Lys Asn Tyr Ser Ile Thr Val
    1190                1195                1200
Ile Ala Arg Asp Gly Gly Asp Arg Gln Ser Glu Ala Ala Ile His
    1205                1210                1215
Val Val Phe Ile Asn Met Thr Gly Glu Pro Ala Phe Leu Glu Pro
    1220                1225                1230
Thr Phe Asp Thr Asp Phe Thr Glu Asn Glu Glu Gly Arg Asp Glu
    1235                1240                1245
Arg Arg Gln Leu Pro Phe Ala Glu Asp Pro Lys Asn Ala Gly Leu
    1250                1255                1260
Pro Pro Gly Ala Glu Thr Asn Val Tyr Tyr Phe Ile Asp Lys Thr
    1265                1270                1275
Tyr Gly Asn Ala Ser His Leu Phe Gln Leu Asp Arg Val Ser Asn
    1280                1285                1290
Val Leu Gln Leu Ala Gln Leu Leu Asp Arg Glu Glu Ile Pro Thr
    1295                1300                1305
Pro Glu Ile Arg Ile Val Ala Thr Asn Asn Glu Asn Ser Pro Pro
    1310                1315                1320
Asp Thr Val Leu Glu Ser Ser Pro Ser Leu Leu Val Val Arg Ile
    1325                1330                1335
Lys Val Asn Asp Val Asn Asp Asn Pro Pro Val Phe Gln Gln Arg
    1340                1345                1350
Leu Tyr Ala Ala Gly Ile Thr Thr Asn Asp Arg Val Pro Lys Ala
    1355                1360                1365
Leu Phe Arg Val Tyr Ala Glu Asp Pro Asp Pro Glu Asp Glu Ile Ile
    1370                1375                1380
Arg Tyr Glu Leu Val Asn Gly Thr Ala Val Gly Glu Asn Leu Gln
    1385                1390                1395
Thr Asp Gly Leu Pro Phe Arg Leu His Pro Asp Ser Gly Glu Leu
    1400                1405                1410
Thr Leu Thr Ser Lys Val Gln Pro Asn Gln Asn Gly Tyr Tyr Gln
    1415                1420                1425
Leu Thr Leu Ile Ala Phe Asp Arg Asp Asp Thr His Asn Asp Thr
    1430                1435                1440
Val Pro Ala Lys Val Tyr Ile Val Ser Glu Ser Asn Arg Val Thr
    1445                1450                1455
Phe Val Phe Leu Asn Ser Val Glu Glu Ile Asp Gln Pro Asp Val
    1460                1465                1470
Arg Lys Phe Leu Ala Gln Glu Leu Thr Gly Ala Tyr Glu Met Glu
    1475                1480                1485
Cys Asn Ile Asp Asp Ile Asp Gln Thr Thr Ala Ser Asp Gly Arg
    1490                1495                1500
```

-continued

| | | | | | | | | | | | |
|---|---|---|---|---|---|---|---|---|---|---|---|
| Gln | Ala | Gly | Gly | Ser | Ser | Ala | Leu | Thr | Asp | Val | Arg Thr His |
| 1505 | | | | | 1510 | | | | 1515 | | |
| Phe | Ile | Gln | Asp | Asn | Gln | Ala | Val | Glu | Ala | Ser | Arg Ile Gln Gln |
| 1520 | | | | | 1525 | | | | 1530 | | |
| Arg | Ser | Ser | Asn | Arg | Thr | Phe | Val | Thr | Val | Leu | Lys Thr Thr Leu |
| 1535 | | | | | 1540 | | | | 1545 | | |
| Arg | Thr | Arg | Gly | Leu | Ser | Leu | Gln | Asp | Val | Pro | Pro Leu Ala Thr |
| 1550 | | | | | 1555 | | | | 1560 | | |
| Glu | Ala | Leu | Thr | Glu | Ala | Asp | Glu | Thr | Leu | Gln | Ile Ile Leu Ile |
| 1565 | | | | | 1570 | | | | 1575 | | |
| Val | Val | Ser | Ala | Ala | Leu | Ala | Val | Leu | Cys | Val | Ile Leu Phe Val |
| 1580 | | | | | 1585 | | | | 1590 | | |
| Ala | Phe | Phe | Ile | Lys | Ile | Arg | Ser | Leu | Asn | Arg | Gln Leu Lys Ala |
| 1595 | | | | | 1600 | | | | 1605 | | |
| Leu | Ser | Ala | Thr | Asp | Phe | Gly | Ser | Ile | Ser | Ser | Glu Leu Asn Gly |
| 1610 | | | | | 1615 | | | | 1620 | | |
| Lys | Pro | Thr | Arg | Asn | Val | Pro | Thr | Thr | Asn | Ile | Phe Ser Ile Glu |
| 1625 | | | | | 1630 | | | | 1635 | | |
| Gly | Ser | Asn | Pro | Val | Leu | Asn | Asp | Asn | Glu | Phe | Arg Asp Arg Met |
| 1640 | | | | | 1645 | | | | 1650 | | |
| Gly | Gly | Gly | Gly | Gly | Val | Tyr | Asp | Asp | Leu | Ser | Leu Gln Ser |
| 1655 | | | | | 1660 | | | | 1665 | | |
| Glu | Glu | Ser | Asp | Phe | Asn | Asp | Val | Asp | Arg | Asp | Ile Phe Ala Pro |
| 1670 | | | | | 1675 | | | | 1680 | | |
| Lys | Arg | Lys | Glu | Ser | Leu | Asn | Pro | Ala | Leu | Leu | Glu His Ile Arg |
| 1685 | | | | | 1690 | | | | 1695 | | |
| Gln | Arg | Ser | Leu | Asn | Pro | Met | Ala | Asn | Gly | Thr | Asp Lys Ser Asn |
| 1700 | | | | | 1705 | | | | 1710 | | |
| Asp | Gly | Ala | Pro | Thr | Ser | Asn | His | Lys | Lys | Leu | Asp Glu Thr Asp |
| 1715 | | | | | 1720 | | | | 1725 | | |
| Asp | Glu | Leu | Ser | His | Arg | Phe | | | | | |
| 1730 | | | | | 1735 | | | | | | |

METHOD FOR INHIBITING INSECTS WITH AN INSECT CADHERIN ECTODOMAIN

CROSS-REFERENCE TO RELATED APPLICATION

This application claims priority to provisional application Ser. No. 60/538,715, filed Jan. 22, 2004.

GOVERNMENTAL RIGHTS

This invention was made in part with government support under Grant No. AI 29092 awarded by the National Institutes of Health. The government may have certain rights in this invention.

BACKGROUND OF THE INVENTION

Various receptors on insect cells for *Bacillus thuringiensis* (*B.t.*) insecticidal toxin proteins are known in the art. See, e.g., U.S. Pat. Nos. 6,586,197; 6,429,360; 6,137,033; and 5,688,691. However, no known prior art taught or suggested administering fragments of cadherin-like proteins, especially fragments of *B.t.* toxin receptors, to insects.

*Bacillus thuringiensis* as an Insecticide. *Bacillus thuringiensis* (*B.t.*) is a facultative anaerobic, Gram-positive, motile, spore-forming bacterium. *B.t.* is accepted as a source of environment-friendly biopesticide. Farmers have applied *B.t.* as an insecticidal spray for control of lepidopteran and coleopteran pests for more than 30 years. The United States Environmental Protection Agency has considered *B.t.* sprays to be so safe that it has exempted them from the requirement of a tolerance (a standard for a maximum permissible residue limit on food).

There are other alternatives for delivery of *B.t.* toxin to target insects. *B.t.* toxin genes are inserted into microorganisms that are associated with the target insect habitat so that the transformed organisms will colonize and continue to produce enough quantities of toxin to prevent insect damage. Examples of these are the insertion of specific genes into bacteria that colonize plant leaf surface and roots externally, such as *Pseudomonas cepacia*, or internally, such as *Clavibacter xyli*. However, the release of living recombinant microorganisms causes many concerns and regulatory restrictions. Alternative methods of introducing genes into microorganisms have been developed to minimize potential horizontal gene flow to other bacterial species. These include using transposase-negative derivatives of Tn5 transposon, or suicide vectors that rely on homologous recombination for integration to be completed. There has also been a development of non-viable recombinant organisms that could increase toxin persistence in the field, such as products based on encapsulated *B.t.* toxins in *P. fluorescens*. This approach eliminates concerns associated with testing of living genetically engineered microorganisms.

*B.t.* proteins may be delivered in transgenic plants. Examples of such plants, called *B.t.* plants, protected from insect attack include cotton and corn. The U.S. Environmental Protection Agency has approved the commercial planting of *B.t.* cotton and corn since 1996.

The mechanism of action of the *B.t.* toxins proceeds through several steps that include solubilization of ingested crystal, proteolytic activation of the protoxins, binding of toxin to midgut receptors, and insertion of the toxin into the apical membrane to form ion channels or pores. Binding of the toxin to brush border membrane vesicles (BBMV) is supposed to be a two-step process involving reversible and irreversible steps. Multiple receptors may be involved in the process of toxin binding and membrane insertion.

Tabashnik et al. (Tabashnik 1992) described the phenomenon of synergy for *B.t.* Cry toxins and developed a formula for calculating synergy. Cry proteins are considered synergistic if the combined insecticidal potency is greater than the sum of the individual components. Cry1Aa and Cry1Ac are synergistic in bioassays against gypsy moth larvae (Lee and Dean, 1996). Other examples of *B.t.* synergy are reported for the Cry proteins of *B.t. israelensis* and combinations of spores and crystals against *Plutella xylostella*, the diamondback moth (Liu et al., 1998). Non-*B.t.* molecules are also known to synergize toxins. For example, ethylenediamine tetra acetic acid (EDTA) synergizes *B.t.* against *P. xylostella*. The synergy described herein is novel both in the nature of the synergistic molecule and the effect detected on important Lepidoptera larvae.

*B.t.* Toxin Receptors. Characterization of receptors from insect midgut and investigation of their interaction with Cry toxins provides an approach to elucidating toxin mode of action and designing improved Cry toxins for pest control. Most Cry toxin-binding midgut proteins identified to date belong to two main protein families: cadherin-like proteins and aminopeptidases. There is in vitro and in vivo evidence supporting the involvement of aminopeptidases in Cry1 toxicity against lepidopteran larvae. Aminopeptidases bind Cry toxins specifically allowing them to form pores in membranes (Masson et al., 1995; Sangadala et al., 2001; Sangadala et al., 1994). Recent studies provide evidence that aminopeptidase can function as receptors when expressed in cultured cells (Adang and Luo 2003) and insects (Gill and Ellar 2002; Rajagopal et al., 2002). Aminopeptidases do not always confer susceptibility to Cry toxins when expressed in heterologous systems (Banks et al., 2003; Simpson and Newcomb 2000).

Cadherin-like proteins are a class of Cry1 receptor proteins in lepidopteran larvae. *Bombyx mori*, the silkmoth, has a 175-kDa cadherin-like protein called BtR175 that functions as a receptor for Cry1Aa and Cry1Ac toxins on midgut epithelial cells (Hara et al., 2003; Nagamatsu et al., 1999). *M. sexta* has a 210-kDa cadherin-like protein, called Bt-R$_1$, that serves as a receptor for Cry1A toxins (Bulla 2002a, b; Vadlamudi et al., 1993; Vadlamudi et al., 1995). Bt-R$_1$, binds Cry1Aa, Cry1Ab, and Cry1Ac toxins on ligand blots (Francis and Bulla 1997). Purified membranes from COS cells expressing Bt-R$_1$ bound all three Cry1A toxins in binding assays and ligand blots (Keeton and Bulla 1997). Furthermore, expression of Bt-R$_1$ on the surface of COS7 cells led to toxin-induced cell toxicity as monitored by immunofluorescence microscopy with fixed cells (Dorsch et al., 2002).

Cadherin-like Bt-R$_1$ protein has been suggested to induce a conformational change in Cry1Ab that allows the formation of a pre-pore toxin oligomer and increases binding affinity for aminopeptidase (Bravo et al. 2004). In *Bombyx mori*, the cadherin-like protein BtR175 serves as a Cry1Aa receptor (Nagamatsu et al., 1998). Sf9 cells expressing BtR175 swell after exposure to Cry1Aa toxin, presumably due to formation of ion channels in cell membranes (Nagamatsu et al. 1999). When expressed in mammalian COS7 cells, BtR175 induced susceptibility to Cry1Aa (Tsuda et al., 2003).

Hua et al. (Hua et al. 2004) developed a fluorescence-based assay using *Drosophila* S2 cells to analyze the function of *Manduca sexta* cadherin (Bt-R$_{1a}$) as a Cry1 toxin receptor. Bt-R$_{1a}$ cDNA that differs from Bt-R$_1$ by 37 nucleotides and two amino acids and expressed it transiently in *Drosophila melanogaster*, Schneider 2 (S2) cells (Hua et al. 2004). Cells expressing Bt-R$_{1a}$ bound Cry1Aa, Cry1Ab, and Cry1Ac toxins on ligand blots, and in saturation binding assays. More Cry1Ab was bound relative to Cry1Aa and Cry1Ac, though each Cry1A toxin bound with high-affinity (Kd values from 1.7 nM to 3.3 nM). Using fluorescent microscopy and flow cytometry assays, (Hua et al. 2004) showed that Cry1Aa, Cry1Ab and Cry1Ac, but not Cry1Ba, killed S2 cells expressing Bt-R$_{1a}$ cadherin. These results demonstrated that *M. sexta* cadherin Bt-R$_{1a}$ functions as a receptor for the Cry1A toxins in vivo and validates our cytotoxicity assay for future receptor studies.

Involvement of a cadherin-superfamily gene disruption in resistance to Cry1Ac has been described for a laboratory resistant strain of *Heliothis virescens* (Gahan et al., 2001). The encoded protein, called HevCaLP, has the binding properties expected for a Cry1A receptor (Jurat-Fuentes et al. 2004). Similarly, *Pectinophora gossypiella* larvae with resistance alleles in genes encoding a cadherin-like protein were resistant to Cry1A toxins (Morin et al., 2003).

*B.t.* toxins bind to specific regions on cadherin-like proteins. Regions of domain II of Cry1A toxins are involved in binding to Bt-R$_1$ (Gomez et al., 2002; Gomez et al., 2001). The first toxin binding region identified in Bt-R$_1$ was a stretch of seven amino acid residues located in the cadherin repeat seven (CR7) (Gomez et al. 2002; Gomez et al. 2001). (Dorsch et al. 2002) identified a second Cry1Ab binding region within cadherin repeat 11 (CR11) in Bt-R$_1$. Recombinant and synthetic peptides containing both amino acid sequences inhibited Cry1Ab toxicity in vivo when fed to *M. sexta* larvae (Dorsch et al. 2002; Gomez et al. 2001), demonstrating their involvement in toxin action. Previously, two Bt-R$_1$ toxin-binding regions in CR 7 (Gomez et al. 2001) and 11 (Dorsch et al. 2002) were proposed as functional receptor sites. U.S. Ser. No. 60/538,753 entitled "Novel Binding Domain of Cadherin-like Toxin Receptor," by Adang et al., under Attorney Docket No. UGR-104P, identifies an additional binding site recognized by Cry toxins that functions as a receptor. This additional binding site, which is also a functional receptor region, is contained in the CR12-Membrane Proximal Extracellular Domain (MPED) of Bt-R1$_a$ (Hua et al. 2004). The HevCaLP protein of *H. virescens* has a Cry1Ac binding site at a comparable position (Xie et al. 2004), suggesting a conservation of binding sites between cadherins of different insect species.

There is no known report or suggestion of a *B.t.* toxin receptor or fragment thereof being fed, or otherwise administered, to an insect pest, with or without a *B.t.* protein, in order to kill or otherwise prevent the insect from feeding on a plant. Previous competitive-binding studies suggest that there would be no change in toxicity (Gomez et al. 2002) or a reduction in toxicity due to competitive binding (Gomez et al. 2001; Dorsch et al. 2002; Gomez et al. 2003; Xie et al. 2004).

BRIEF SUMMARY OF THE INVENTION

The subject invention pertains to the use of peptide fragments of proteins for controlling insects. In preferred embodiments, the source protein is a cadherin (including cadherin-like proteins) and/or a *Bacillus thuringiensis* (*B.t.*) crystal protein (Cry) toxin receptors. Preferably, the peptide fragment is a binding domain of the receptor. In some preferred embodiments, the peptide is the binding domain nearest to the membrane proximal ectodomain. Corresponding domains are identifiable in a variety of *B.t.* toxin receptors. Thus, one aspect of the invention pertains to the use of an isolated polynucleotide that encodes a protein comprising (or consisting of) a fragment of a cadherin-like protein.

In preferred embodiments, the peptides are fed to target insects together with one or more insecticidal proteins, preferably (but not limited to) *B.t.* Cry proteins. When used in this manner, the peptide fragment can not only enhance the apparent toxin activity of the Cry protein against the insect species that was the source of the receptor but also against other insect species.

The subject invention includes a cell (and use thereof) carrying the polynucleotide and expressing the peptide fragment, including methods of feeding the peptide (preferably with *B.t.* Cry toxins) to insects.

BRIEF DESCRIPTION OF THE FIGURES

FIG. 2 shows results of toxin binding assays under native conditions (dot blotting and binding saturation assays). Designations are according to Bt-R$_{1a}$ constructs in FIG. 1. FIG. 2 shows Cry1Ab binding to truncated and full-length Bt-R$_{1a}$ cadherin expressed in *Drosophila* S2 cells under non-denaturing conditions and competition by CR12-MPED peptide. S2 cells (5×10$^5$ cells) were dot-blotted on PVDF filters. After blocking, the filters were probed with $^{125}$I-Cry1Ab or $^{125}$I-Cry1Ab plus 1000-fold excess (molar ratio) purified CR12-MPED peptide. FIG. 2 shows $^{125}$I-Cry1Ab binding to the expressed Cad12 truncated fragment containing CR12, but not to CR11 alone.

FIG. 3 shows the amino acid sequence of CR12-MPED truncated *M. sexta* cadherin Bt-R$_{1a}$ in pET-30a(+) (Novagen). (SEQ ID NO:14). Bold letters and underline designates Bt-R$_{1a}$ amino acids. The truncated open reading frame from Bt-R$_{1a}$ is designated CR12-MPED. (264 residues total—206 residues from Bt-R$_{1a}$ (78%); 58 residues from pET-30a(+) (22%). MW=28652 Dalton.).

FIGS. 4A and 4B illustrate that CR12-MPED enhanced the potency of *B.t.* Cry1Ab. FIGS. 4A and 4B show live and dead larvae, and illustrate the reduced size of larvae in all groups fed with combinations of Cry1Ab plus CR12-MPED.

Figure 5E:
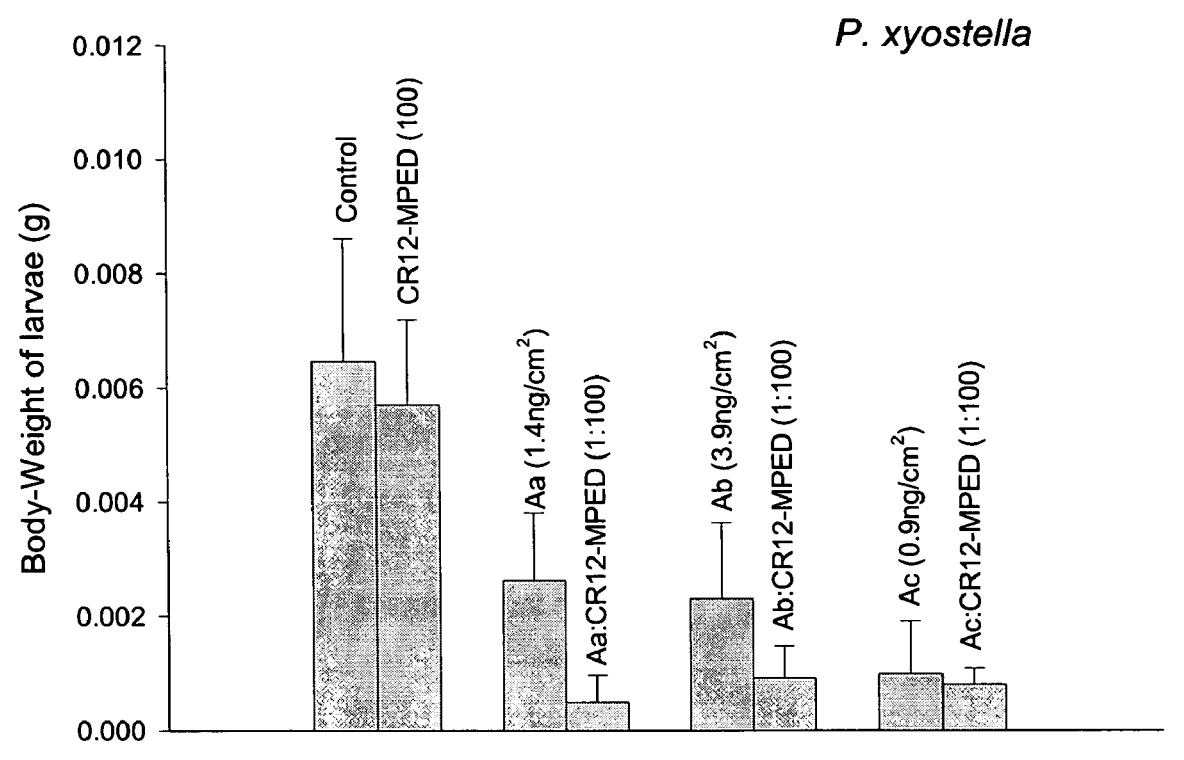

FIGS. 5A-F shows the toxicity effect as body-weight of surviving *Manduca sexta, Heliothis virescens, Helicoverpa zea, Spodoptera frugiperda,* and *Plutella xylostella* larvae fed CR12-MPED truncated cadherin peptide with Cry1A toxins.

FIGS. 6A-F show photographs of surviving *Manduca sexta, Heliothis virescens, Helicoverpa zea, Spodoptera frugiperda, B.t.*-susceptible *Plutella xylostella*, and *B.t.*-resistant *Plutella xylostella* larvae fed a mixture of *B.t.* Cry1A toxins and CR12-MPED truncated cadherin peptide with Cry1A toxins.

FIG. 7 shows that CR11-MPED enhances Cry1Ab toxicity to *Manduca sexta* (tobacco hornworm).

FIG. 8 shows bioassay of Cry1Ac with cadherin fragments on soybean looper (*Pseudoplusia includens*).

FIG. 9 shows bioassay on soybean looper with Cry2Aa and different truncations of BtR1$_a$ cadherin. Ano-PCAP data are included.

FIG. 11 illustrates results of the diet overlay bioassay on the soybean looper (*Pseudoplusia includens*) neonate mortality to the mixture of CR12-MPED and 5 ng/cm$^2$ Cry1Ac with different toxin:peptide ratios.

BRIEF DESCRIPTION OF THE SEQUENCES

Figure 1:
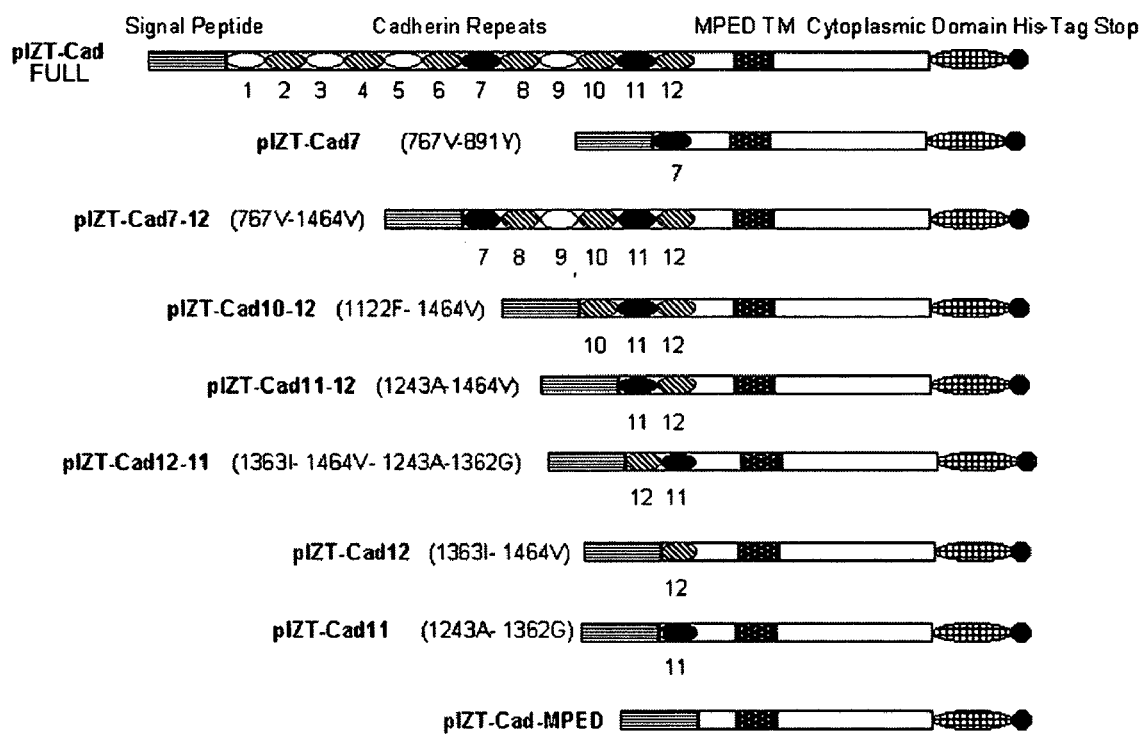
FIG. 1 illustrates Bt-R$_{1a}$ truncated cadherin constructs expressed on the surface of S2 cells using the vector pIZT-V5-His (Invitrogen) and transfected into *Drosphila* S2 cells. Plasmids are designated for the cadherin repeats (CR) encoded. Numbers in parentheses indicated the amino acid residues of the CR start and end positions. CR units 7 and 11 (in black) contain Toxin Binding Regions 1 and 2, respectively.
Figure 5A:
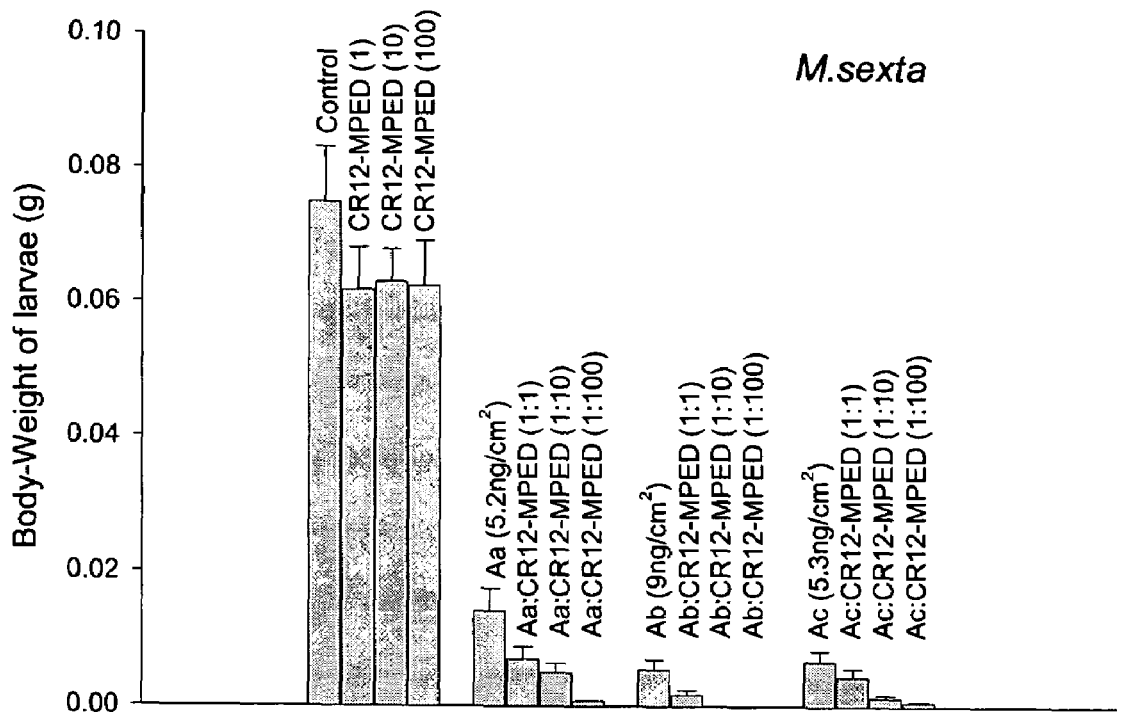
Figure 5B:
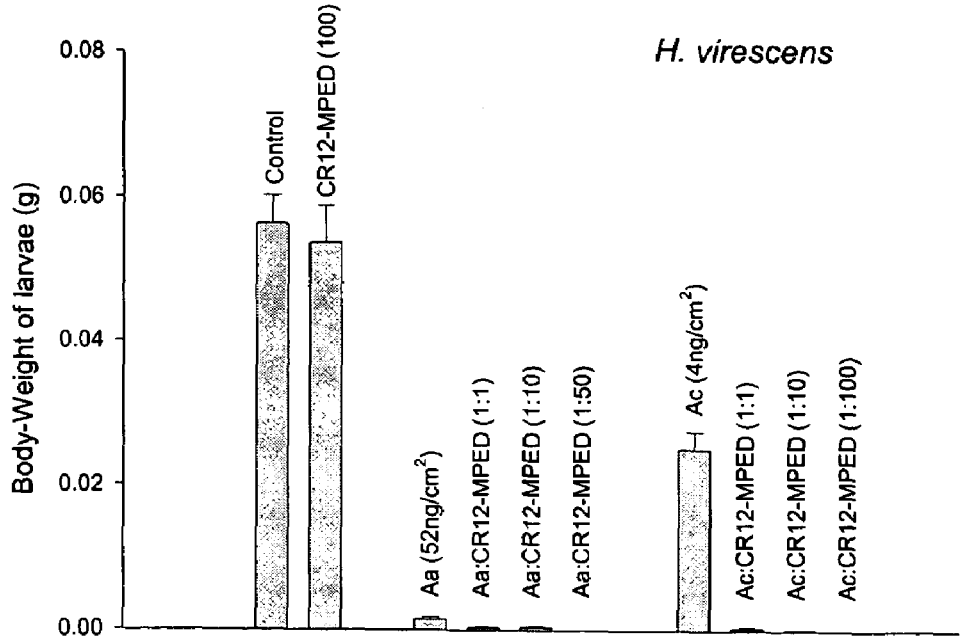
Figure 5C:
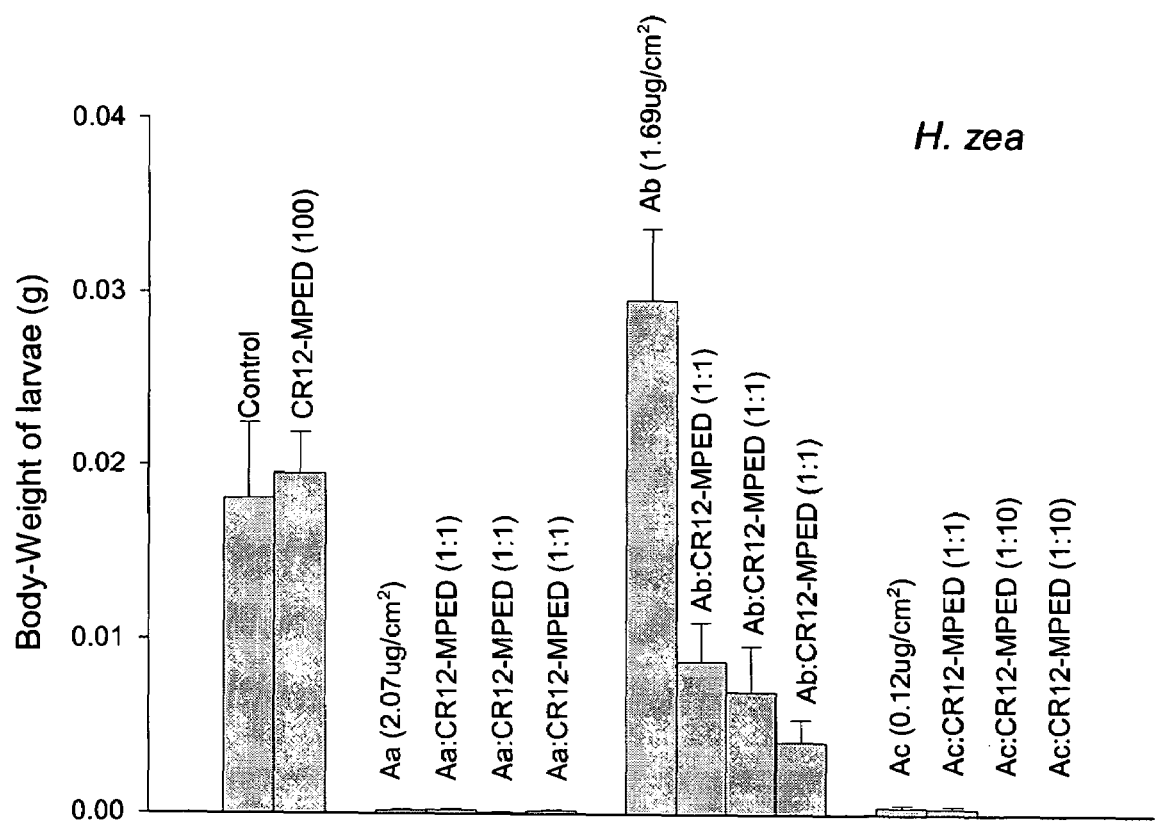
Figure 5D:
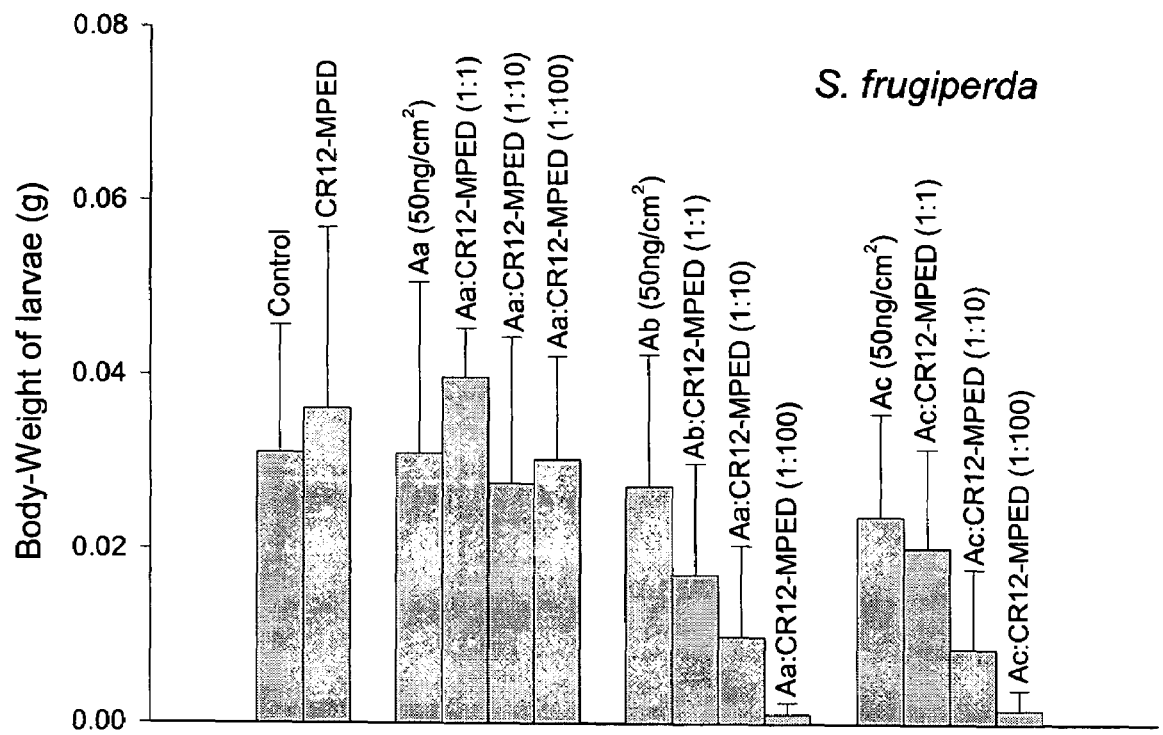

SEQ ID NO:1 is a nucleotide sequence that encodes the CR12-MPED peptide.

SEQ ID NO:2 is the amino acid sequence of the CR12-MPED peptide. This peptide may be referred to as "*B.t.* Booster" or "BTB."

SEQ ID NO:3 shows the nucleotide sequence of CR11-MPED truncated form of *M. sexta* cadherin Bt-R$_{1a}$. CR11-MPED can be referred to as BtB$_2$, which has 324 amino acid residues from *Bacillus thuringiensis*-R$_{1a}$ encoding an approximately 35,447 Dalton protein (theoretical pI=4.72).

SEQ ID NO:4 shows the amino acid sequence of CR11-MPED truncated form of *M. sexta* cadherin Bt-R$_{1a}$. This peptide is as-produced by *E. coli* strain BL21/DE3/pRIL cloned with the pET-30a vector.

SEQ ID NO:5 shows the nucleotide sequence of CR1-3 from *M. sexta* BtR1a.

SEQ ID NO:6 shows the amino acid sequence of CR1-3 from *M. sexta* BtR1a. This peptide is as-produced by *E. coli* strain BL21/DE3/pRIL cloned with the pET-30a vector.

SEQ ID NO:7 (file Anof-PCAPseq.doc) shows the nucleotide sequence of the putative cell adhesion protein of *Anopheles gambiae* (NCBI LOCUS XM_321513).

SEQ ID NO:8 (file Anof-PCAPseq.doc) shows the amino acid sequence of the putative cell adhesion protein of *Anopheles gambiae* (NCBI LOCUS XM_321513).

SEQ ID NO:9 shows the nucleotide sequence encoding "PCAP"—the truncation from the *Anopheles gambiae* putative cell-adhesion protein (PCAP).

SEQ ID NO:10 shows the truncated PCAP (putative cell-adhesion protein) region of the *Anopheles gambiae* protein. This truncated peptide is referred to herein as PCAP or Ano-PCAP (213 amino acid residues—a 24416.56 Dalton protein, theoretical pI=4.96). This peptide is as-produced from the DNA being cloned into pET-30a vector and expressed in *E. coli* strain BL2 1/DE3/pRIL.

SEQ ID NO:11 shows the full-length *Anopheles gambiae* cDNA cadherein sequence. BLAST search with the sequence matches the DNA and predicted protein sequence for a partial *Anopheles gambiae* cDNA (NCBI Locus XM_312086).

SEQ ID NO:12 shows the "Ano-Cad"-encoding fragment of SEQ ID NO:11 that was cloned into the pET-30A vector and expressed in *E. coli* strain BL21/DE3.

SEQ ID NO:13 shows the full-length *Anopheles gambiae* cadherin protein encoded by SEQ ID NO:11. Residues 1358-1569 of SEQ ID NO:13 correspond to the "Ano-Cad" peptide encoded by SEQ ID NO:12.

SEQ ID NO:14 shows the amino acid sequence of CR12-MPED truncated *M. sexta* cadherin Bt-R$_{1a}$ in pET-30a(+) (Novagen).

DETAILED DESCRIPTION OF THE INVENTION

The subject invention concerns methods and materials used for controlling insects and other pests, particularly plant pests. More specifically, the subject invention pertains to the use of peptide fragments of a protein, preferably a cadherin (including cadherin-like proteins), for controlling insects. Alternatively or in addition, the protein is preferably a *Bacillus thuringiensis* (*B.t.*) crystal protein (Cry) toxin receptor. These peptide fragments are provided, or made available, to target pests for ingestion. This can be accomplished by a variety of means that are known in the art, some of which are discussed in more detail below.

Preferred are fragments of the ectodomains of cadherin proteins (the portion of the protein that is outside of the cell when part of the cadherin protein is embedded in the cellular membrane and part is exposed at the cell surface). Preferably, the cadherins can be *Bacillus thuringiensis* (*B.t.*) crystal protein (Cry) toxin receptors. Preferably, the peptide fragment is a binding domain of the receptor. In some preferred embodiments, the peptide is the binding domain nearest to the membrane proximal ectodomain. Corresponding domains are identifiable in a variety of *B.t.* toxin receptors.

In preferred embodiments, the peptides are fed to target insects together with one or more insecticidal proteins, preferably (but not limited to) *B.t.* Cry proteins. When used in this manner, the peptide fragment can not only enhance the apparent toxin activity of the Cry protein against the insect species that was the source of the receptor but also against other insect species.

A related aspect of the inventions pertains to the use of an isolated polynucleotide that encodes a protein comprising (or consisting of) a fragment of a cadherin-like protein. The subject invention includes a cell (and use thereof) carrying the polynucleotide and expressing the peptide fragment, including methods of feeding the peptide (preferably with *B.t.* Cry toxins) to insects. The nucleotide sequences can be used to transform hosts, such as plants, to express the receptor fragments (preferably cadherin fragments) of the subject invention. Transformation of plants with the genetic constructs disclosed herein can be accomplished using techniques well known to those skilled in the art. Thus, in some embodiments, the subject invention provides nucleotide sequences that encode fragments of receptors, preferably a Bt-R$_1$ cadherin-like protein.

The receptor used as the source of this domain(s) can be derived from various pests and insects, such as *Manduca sexta, Heliothis virescens, Helicoverpa zea Spodoptera frugiperda* and *Plutella xylostella* larvae. Many sequences of such receptors are publicly available. The subject peptide fragments can not only enhance a toxin's activity against the insect species that was the source of the receptor, but also against other insect species.

Various pests can be targeted, including but not limited to *Manduca sexta, Heliothis virescens, Helicoverpa zea Spodoptera frugiperda* and *Plutella xylostella* larvae. Because of the unique and novel approach of the subject invention, pests that were typically not susceptible to *B.t.* Cry proteins can now also be targeted. For example, hemipterans represent a major group of insects that have typically not been effectively controlled by *B.t.* δ-endotoxins. Numerous hemipteran pest species, most notably *Lygus* species, cause considerable plant damage and economic loss each year. The digestive system of hemipterans (including aphids) is unusual among the insects in several ways: certain hydrolytic digestive enzymes are absent such as trypsin; the midgut lacks a peritrophic membrane, and there is no crop. These features reflect the liquid diet and sucking mode of feeding, subject to evolutionary constraints. However, because of the subject novel approach, the subject invention offers new alternatives for pest control. The subject invention can be used to enhance and expand the spectrum (or insect range) of toxicity of a given insect-toxic protein.

In some preferred embodiments, these peptide fragments can be used to enhance the potency of B.t. toxins for controlling insects. In some preferred embodiments, the peptide fragments enhance the toxicity of Cry1 toxins, but as shown herein, the subject invention is not limited to use with such toxins.

Various types of plants and crops can be protected in a variety of ways by practicing the subject invention. Cotton and corn are the main crops that can be protected by peptides (and proteins) of the subject invention, as well as soybeans and rice. Preferred methods for protecting these crops include producing transgenic crops that are engineered to produce peptides (and proteins) according to the subject invention. Preferred uses for spray-on applications include, but are not limited to, protecting vegetables and targeting forest pests (protecting planted trees and the like). Preferred pests for targeting in this manner include but are not limited to lepidopterans.

Without being bound by a specific theory or theories of mechanism of action, one possibility is that these fragments work in conjunction with B.t. toxins and enhance the pesticidal activity of the toxin. When fed to insects with a Cty toxin, the peptide can change the effect of a toxin from a growth-inhibitory effect to an insecticidal effect. In addition or alternatively, the fragments can exert at least a partial toxic effect by a separate mechanism of action. Yet another possibility is that the fragments also, or alternatively, work indirectly to stabilize the B.t. toxin. Thus, said fragment can work independently from the Cry toxin (by another mechanism of action) and/or in conjunction with the Cry toxin to enhance the insecticidal potency of the Cry toxin. However, the mechanism(s) of action are not important for practicing the subject invention. Based on the subject disclosure, one skilled in the art can practice various aspects of the subject invention in a variety of ways.

For example, the fragment of cadherin-like protein may be expressed as a fusion protein with a B.t. Cry toxin using techniques well known to those skilled in the art. As described herein, preferred fusions would be chimeric toxins produced by combining a toxin (including a fragment of a protoxin, for example) and a fragment of a cadherin-like protein. In addition, mixtures and/or combinations of toxins and cadherin-like protein fragments can be used according to the subject invention. These mixtures or chimeric proteins have the unexpected and remarkable properties of enhanced insecticidal potency.

It should similarly be noted that one skilled in the art, having the benefit of the subject disclosure, will recognize that the subject peptides potentially have a variety of functions, uses, and activities. As stated herein, the subject peptides can be administered together with a Cry protein. When used in this manner, peptides of the subject invention can effect a faster kill of the targeted insects, and/or they can enable less Cry protein to be required for killing the insects. Complete lethality, however, is not required. The ultimate preferred goal is to prevent insects from damaging plants. Thus, prevention of feeding is sufficient. Thus "inhibiting" the insects is all that is required. This can be accomplished by making the insects "sick" or by otherwise inhibiting (including killing) them so that damage to the plants being protected is reduced. Peptides of the subject invention can be used alone or in combination with another toxin to achieve this inhibitory effect, which can be referred to as "toxin activity." Thus, the inhibitory function of the subject peptides can be achieved by any mechanism of action, directly or indirectly related to the Cry protein, or completely independent of the Cry protein.

In specific embodiments, the subject invention relates to the use of a cadherin repeat 12-MPED peptide of *Manduca sexta* Bt-$R_{1a}$ cadherin-like protein to enhance the potency of B.t. toxins. A region (i.e., fragment) of a cadherin-like protein was identified that synergizes the insecticidal potency of a B.t. Cry toxin. The receptor fragment binds toxin with high-affinity, catalyzes toxin-induced cell death when expressed on the surface of cultured insects cells, and enhances (i.e., synergizes) the insecticidal potency of a Cry toxin.

However, in light of the subject disclosure, it will be recognized that other peptides can be used in like manners. For example, a novel Cry1Ab-binding site on Bt-$R_{1a}$ was identified as described in U.S. Ser. No. 60/538,753 entitled "Novel Binding Domain of Cadherin-like Toxin Receptor," by Adang et al., under Attorney Docket No. UGR-104P, which identifies an additional binding site recognized by Cry toxins that functions as a receptor. This additional binding site, which is also a functional receptor region, is contained in the CR12-Membrane Proximal Extracellular Domain (MPED) of Bt-R1$_a$ (Hua et al. 2004). The HevCaLP protein of *H. virescens* has a Cry1Ac binding site at a comparable position (Xie et al. 2004), suggesting a conservation of binding sites between cadherins of different insect species.

Full-length and truncated Bt-$R_{1a}$ fragments were genetically engineered and expressed in *Drosophila* S2 cells to test for Cry1Ab binding and cytotoxicity mediated by receptor fragments. See, e.g., FIG. 1. In toxin binding assays under denaturing conditions (ligand blotting), $^{125}$I-Cry1Ab bound to full length Bt-$R_{1a}$, and to Cad7-12, Cad10-12, and Cad11-12 truncated fragments. Binding assays under native conditions (dot blotting and binding saturation assays) revealed $^{125}$I-Cry1Ab binding to the expressed Cad12 truncated fragment containing CR12, but not to CR11 alone (See, e.g., FIG. 2). In saturation binding assays, $^{125}$I-Cry1Ab toxin bound with similar high affinity to full length Bt-$R_{1a}$, Cad7-12, Cad11-12, and Cad12, although the concentration of receptors was higher for Cad11-12. Fluorescence assisted cell sorting (FACS) assays showed that S2 cells expressing Bt-$R_{1a}$, Cad7-12, Cad10-12, Cad11-12 or Cad12 were susceptible to Cry1Ab. S2 cells expressing Cad7 or Cad11 were not killed by the toxin. Thus, described therein is a novel receptor region on Bt-$R_{1a}$ that is located on CR12. Binding to CR12 is necessary and sufficient to confer susceptibility to Cry1Ab toxin to insect cells.

The subject invention stemmed in part from the unexpected finding that a peptide comprising CR12 and the Membrane Proximal Ectodomain (MPED) (Dorsch et al. 2002) enhanced the toxicity of B.t. Cry1 toxins when fed as a mixture to insect larvae. This peptide, called CR12-MPED, is illustrated in FIG. 3. The peptide not only functions as a Cry-toxin-enhancing agent against *M. sexta*, the original source of Bt-$R_{1a}$ receptor, but functions as an enhancing agent for multiple Cry1 toxins against other pest Lepidoptera including *H. virescens, H. zea* and *S. frugiperda*. The use of a fragment of a B.t. receptor in this manner has not heretofore been described or suggested.

In preferred embodiments, the fragment of the receptor is a binding domain of the receptor. Without being bound by a specific theory regarding mechanism of action, binding of this domain to a B.t. toxin could induce a conformational change in the B.t. toxin, thus making it more toxic, more able to bind the toxin receptor, etc. In some preferred embodiments, the fragment comprises (or consists of) the CR12-MPED domain.

The peptides (such as CR12-MPED) and toxins can be fed or otherwise administered to the target (insect) pest in various ways, according to the subject invention. In one preferred embodiment, a transgenic plant produces the peptide (such as CR12-MPED) and one or more *B.t.* toxins. By consuming the peptide and *B.t.* protein produced by such plant (e.g., by eating plant tissues and cells containing the peptide and protein), the insect will thereby contact the peptide and protein. Together, they will exhibit the enhanced toxic effects in the insect gut.

Another preferred method of the subject invention is to spray the peptide (such as Cad12-MPED) onto transgenic *B.t.* plants (such as corn, cotton, soybeans, and the like). The polypeptide can be in a suitable carrier, as are known in the art. By spraying the peptide in this manner on plant tissues consumed by target pests, the pest will eat both the peptide (in the spray) and the *B.t.* protein (produced by and present in the plant).

Yet another preferred method is to spray both the peptide and the *B.t.* Cry protein onto plants and the like. Such methods are well-known in the art (but heretofore lacked the synergizing peptides of the subject invention). *B.t.* toxins, and/or the peptide of the subject invention, can be formulated with and agriculturally acceptable carrier, for example, that is suitable for spray application to plants and the like.

In one embodiment, the subject invention is drawn to the use of a polynucleotide that encodes a CR12 binding domain from *M. sexta*. In a preferred embodiment, such polynucleotides comprise (or consist of) a nucleotide sequence that encodes the CR12-MPED peptide of SEQ ID NO:2. (The N-terminal "G"—glycine residue—for example, can be removed and the remaining fragment of the exemplified sequence can be used, according to the subject invention.) One such nucleotide sequence is shown in SEQ ID NO:1.

In another embodiment, the subject invention is drawn to the use of a cell or cells transfected with a polynucleotide molecule that comprises a nucleotide sequence encoding a CR12-MPED peptide, for example. Further, the protein is preferably, but not necessarily, anchored to and localized at the cell membrane, and is capable of binding a toxin. In a more preferred embodiment, said protein mediates an observable toxicity to said cell or cells, including death upon contacting a toxin.

While CR12-MPED is one example referred to above and elsewhere herein, several other peptides are exemplified herein. Some other such peptides are discussed below in the Examples. Thus, it should be understood that these other peptides, and variants thereof, can be referred to in the same manners as is CR12-MPED.

As described in the background of the invention, many *B.t.* toxins have been isolated and sequenced. Polynucleotides encoding any known *B.t.* toxins or those yet to be discovered and active fragments thereof (see, for example, U.S. Pat. No. 5,710,020) can be used in accord with the teachings herein. See Crickmore et al. (1998) for a description of other *B.t.* toxins. A list of Cry toxins from the Crickmore et al. website is attached as Appendix A. These include, but are not limited to, polynucleotides encoding Cry1A toxins such as Cry1Aa, Cry1Ab, Cry1Ac, preferably, as well as Cry1B, Cry1C, Cry1F, Cry1E, and Cry3A. Cry2 toxins are also preferred for co-administration with peptides of the subject invention. One can also select toxin(s) from the Crickmore list, for example, based on the type of pests being targeted. For example, rootworms were targeted in an Example as discussed below. Thus, anti-rootworm toxins (such as Cry34/35 toxins) can preferably be used in such applications. The subject peptides can also be used to control mutant insects that are resistant to one or more *B.t.* toxins. Modified Cry toxins (such as those described in U.S. Pat. Nos. 6,825,006; 6,423,828; 5,914,318; and 5,942,664) can also be used according to the subject invention. *B.t.* toxins other than Cry toxins (such as "Vip" toxins as categorized in another section of the Crickmore et al. website) are also contemplated for use. Insecticidal proteins from organisms other than *B.t.*, such as *Bacillus subtilis*, are also contemplated for use.

In order to provide an understanding of a number of terms used in the specification and claims herein, the following definitions are provided.

An "isolated" nucleic acid or polynucleotide (or protein) is in a state or construct that would not be found in nature. Thus, it signifies the involvement of "the hand of man." A polynucleotide encoding a peptide of the subject invention, to the extent that the peptide does not occur in the state of nature, would be an isolated polynucleotide. This polynucleotide in a plant genome would also be "isolated" as it is not occurring in its natural state. The term therefore covers, for example, (a) a DNA which has the sequence of part of a naturally occurring genomic DNA molecule but is not flanked by both of the coding or non-coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein.

A nucleotide sequence is operably linked when it is placed into a functional relationship with another nucleotide sequence. For instance, a promoter is operably linked to a coding sequence if the promoter effects its transcription or expression. Generally, operably linked means that the sequences being linked are contiguous and, where necessary to join two protein coding regions, contiguous and in reading frame. However, it is well known that certain genetic elements, such as enhancers, may be operably linked even at a distance, i.e., even if not contiguous.

Polynucleotides of the subject invention include an isolated polynucleotide "consisting essentially of" a segment that encodes a CR12-MPED peptide, for example, attached to a label or reporter molecule and may be used to identify and isolate *B.t.* toxins and the like. Probes comprising synthetic oligonucleotides or other polynucleotides may be derived from naturally occurring or recombinant single or double stranded nucleic acids or be chemically synthesized. Polynucleotide probes may be labeled by any of the methods known in the art, e.g., random hexamer labeling, nick translation, or the Klenow fill-in reaction.

The polynucleotides may also be produced by chemical synthesis, e.g., by the phosphoramidite method described by Beaucage and Caruthers (1981) *Tetra. Letts.*, 22:1859-1862 or the triester method according to Matteuci et al. (1981) *J. Am. Chem. Soc.*, 103:3185, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

DNA constructs prepared for introduction into a prokaryotic or eukaryotic host will typically comprise a replication system (i.e., vector) recognized by the host, including the intended DNA fragment encoding the desired polypeptide, and will preferably also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included where appropriate from secreted polypeptides of the same or related species, which allow the protein to cross and/or lodge in cell membranes or be secreted from the cell.

Expression and cloning vectors will likely contain a selectable marker, that is, a gene encoding a protein necessary for the survival or growth of a host cell transformed with the vector. Although such a marker gene may be carried on another polynucleotide sequence co-introduced into the host cell, it is most often contained on the cloning vector. Only those host cells into which the marker gene has been introduced will survive and/or grow under selective conditions. Typically selection genes encode proteins that (a) confer resistance to antibiotics or other toxic substances, e.g., ampicillin, neomycin, methotrexate, etc.; (b) complement auxotrophic deficiencies; or (c) supply critical nutrients not available from complex media. The choice of the proper selectable marker will depend on the host cell; appropriate markers for different hosts are known in the art.

It will be recognized by those skilled in the art that the DNA sequences may vary due to the degeneracy of the genetic code and codon usage. All DNA sequences which code for exemplified and/or suggested peptides (and proteins) are included. For example, the subject CR12 peptides are included in this invention, including the DNA of SEQ ID NO:1 (plus an ATG preceding the coding region), which encodes SEQ ID NO:2. The subject invention also includes polynucleotides having codons that are optimized for expression in plants, including any of the specific types of plants referred to herein. Various techniques for creating plant-optimized sequences are know in the art.

Additionally, it will be recognized by those skilled in the art that allelic variations may occur in the DNA sequences which will not significantly change activity of the amino acid sequences of the peptides which the DNA sequences encode. All such equivalent DNA sequences are included within the scope of this invention and the definition of the regulated promoter region. The skilled artisan will understand that exemplified sequences (such as the CR12-MPED sequence of SEQ ID NO:1) can be used to identify and isolate additional, non-exemplified nucleotide sequences which will encode functional equivalents to the sequences given in, or an amino acid sequence of greater than 90% identity thereto and having equivalent biological activity. DNA sequences having at least 90%, or at least 95% identity to a recited DNA sequence and encoding functioning peptides (such as CR12-MPED) are considered equivalent sequences and are included in the subject invention. Other numeric ranges for variant polynucleotides and amino acid sequences are provided below (e.g., 50-99%). Following the teachings herein and using knowledge and techniques well known in the art, the skilled worker will be able to make a large number of operative embodiments having equivalent DNA sequences to those listed herein without the expense of undue experimentation.

As used herein percent sequence identity of two nucleic acids is determined using the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul et al. (1990) *J. Mol. Biol.* 215:402-410. BLAST nucleotide searches are performed with the NBLAST program, score=100, wordlength=12, to obtain nucleotide sequences with the desired percent sequence identity. To obtain gapped alignments for comparison purposes, Gapped BLAST is used as described in Altschul et al. (1997) *Nucl. Acids. Res.* 25:3389-3402. When utilizing BLAST and Gapped BLAST programs, the default parameters of the respective programs (NBLAST and XBLAST) are used. See ncbi.nih.gov website.

Polynucleotides (and the peptides and proteins they encode) can also be defined by their hybridization characteristics (their ability to hybridize to a given probe, such as the complement of a DNA sequence exemplified herein). Various degrees of stringency of hybridization can be employed. The more stringent the conditions, the greater the complementarity that is required for duplex formation. Stringency can be controlled by temperature, probe concentration, probe length, ionic strength, time, and the like. Preferably, hybridization is conducted under moderate to high stringency conditions by techniques well known in the art, as described, for example, in Keller, G. H., M. M. Manak (1987) *DNA Probes*, Stockton Press, New York, N.Y., pp. 169-170.

As used herein "moderate to high stringency" conditions for hybridization refers to conditions that achieve the same, or about the same, degree of specificity of hybridization as the conditions "as described herein." Examples of moderate to high stringency conditions are provided herein. Specifically, hybridization of immobilized DNA on Southern blots with $^{32}$P-labeled gene-specific probes was performed using standard methods (Maniatis et al.). In general, hybridization and subsequent washes were carried out under moderate to high stringency conditions that allowed for detection of target sequences with homology to sequences exemplified herein. For double-stranded DNA gene probes, hybridization was carried out overnight at 20-25° C. below the melting temperature (Tm) of the DNA hybrid in 6×SSPE, 5× Denhardt's solution, 0.1% SDS, 0.1 mg/ml denatured DNA. The melting temperature is described by the following formula from Beltz et al. (1983).

$$Tm=81.5° C.+16.6 \text{ Log}[Na+]+0.41(\% G+C)-0.61 (\% \text{ formamide}) 600/\text{length of duplex in base pairs.}$$

Washes are typically carried out as follows:

(1) Twice at room temperature for 15 minutes in 1×SSPE, 0.1% SDS (low stringency wash).

(2) Once at Tm-20° C. for 15 minutes in 0.2×SSPE, 0.1% SDS (moderate stringency wash).

For oligonucleotide probes, hybridization was carried out overnight at 10-20° C. below the melting temperature (Tm) of the hybrid in 6×SSPE, 5× Denhardt's solution, 0.1% SDS, 0.1 mg/ml denatured DNA. Tm for oligonucleotide probes was determined by the following formula from Suggs et al. (1981):

$$Tm(° C.)=2(\text{number } T/A \text{ base pairs})+4(\text{number } G/C \text{ base pairs})$$

Washes were typically carried out as follows:

(1) Twice at room temperature for 15 minutes 1×SSPE, 0.1% SDS (low stringency wash).

(2) Once at the hybridization temperature for 15 minutes in 1×SSPE, 0.1% SDS (moderate stringency wash)

In general, salt and/or temperature can be altered to change stringency. With a labeled DNA fragment of greater than about 70 or so bases in length, the following can be used:

Low: 1 or 2×SSPE, room temperature

Low: 1 or 2×SSPE, 42° C.

Moderate: 0.2× or 1×SSPE, 65° C.

High: 0.1×SSPE, 65° C.

Duplex formation and stability depend on substantial complementarity between the two strands of a hybrid, and, as noted above, a certain degree of mismatch can be tolerated. Therefore, polynucleotide sequences of the subject invention include mutations (both single and multiple), deletions, and insertions in the described sequences, and combinations thereof, wherein said mutations, insertions, and deletions permit formation of stable hybrids with a target polynucleotide of interest. Mutations, insertions, and deletions can be produced in a given polynucleotide sequence using standard methods known in the art. Other methods may become known in the future.

The mutational, insertional, and deletional variants of the polynucleotide and amino acid sequences of the invention can be used in the same manner as the exemplified sequences so long as the variants have substantial sequence similarity with the original sequence. As used herein, substantial sequence similarity refers to the extent of nucleotide similarity that is sufficient to enable the variant polynucleotide to function in the same capacity as the original sequence. Preferably, this similarity is greater than 50%; more preferably, this similarity is greater than 75%; and most preferably, this similarity is greater than 90%. The degree of similarity needed for the variant to function in its intended capacity will depend upon the intended use of the sequence. It is well within the skill of a person trained in this art to make mutational, insertional, and deletional mutations that are designed to improve the function of the sequence or otherwise provide a methodological advantage. The identity and/or similarity can also be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein.

The amino acid identity/similarity and/or homology will be highest in critical regions of the protein that account for biological activity and/or are involved in the determination of three-dimensional configuration that ultimately is responsible for the biological activity. In this regard, certain amino acid substitutions are acceptable and can be expected if these substitutions are in regions that are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 1 provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

Practicing some embodiments of the subject invention might necessitate the use of expression vectors comprising one or more polynucleotides comprising an exemplified nucleic acid sequences, and capable of expressing the subject peptides, in a suitable host cell. In the vectors of the subject invention, the polynucleotide encoding the peptide is operably linked to suitable transcriptional and/or translational regulatory elements to effect expression of the peptide in a suitable host cell. The regulatory elements may be derived from mammalian, microbial, viral or insect genes and include, for example, promoters, enhancers, transcription and translation initiation sequences, termination sequences, origins of replication, and leader and transport sequences. Suitable regulatory elements are selected for optimal expression in a desired host cell.

Possible regulatory sequences can include, but are not limited to, any promoter already shown to be constitutive for expression, such as those of viral origin (e.g., IEI promoter from Baculoviruses) or so-called "housekeeping" genes (ubiquitin, actin, tubulin) with their corresponding termination/poly A+ sequences. In addition, the gene can be placed under the regulation of inducible promoters and their termination sequences so that gene expression is induced by light (rbcS-3A, cab-1), heat (hsp gene promoters) or wounding (mannopine, HGPGs). Other suitable promoters include the metallothionein promoter, dexamethasone promoter, alcohol dehydrogenase promoter, and the baculovirus promoters, i.e., the early promoter (e.g., IE-1 and et1), the late promoters (e.g., vp39 and p6.9), the very late promoters (e.g., po1h and p10) and the hybrid promoter (e.g., vp39/po1h).

It is clear to one skilled in the art that a promoter may be used either in native or truncated form, and may be paired with its own or a heterologous termination/polyA+ sequence. In a preferred embodiment, the subject vectors are regulated by *D. melanogaster* HSP70 promoter.

Expression vectors can be constructed by well known molecular biological methods as described for example in Sambrook et al. (1989), or any of a myriad of laboratory manuals on recombinant DNA technology that are widely available. Expression vectors into which the polynucleotides of the present invention can be cloned under the control of a suitable promoter are also commercially available. Recombinant viral vectors, including retroviral, baculoviral, parvoviral and densoviral vectors can be used but are not particularly preferred. In host cells containing vectors having an inducible promoter controlling the expression of the nucleic acid encoding CR12-MPED, for example, expression is induced by methods known in the art and suitable for the selected promoter. For example, expression of nucleic acids under the control of the metallothionein promoter is induced by adding cadmium chloride or copper sulfate to the growth media of host cells.

In a specific embodiment, the subject invention includes the pest-control use of a host cell containing a vector comprising nucleotide sequences encoding CR12-MPED under the control of a promoter. The host cell may be procaryotic or eukaryotic, including bacterial, yeast, insect and mammalian cells. Insect and mammalian cells are preferred. Particularly preferred host cells include insect cell lines, such as, for example, *Spodoptera frugiperda* (Sf9 and Sf21) and *Trichoplusia ni* (Tn cells), *Estigma acrae* (Ea4 cells), *Drosophila melanogaster* (Dm cells), *Choristoneura fumiferama* (Cf-1 cells), *Mamestra brassicae* (MaBr-3 cells), *Bombyx mori* (MnN4 cells), *Helicoverpa zea* (Hz1b3 cells), and *Lymantria dispar* (Ld652Y cells), among others. The host cells may be transformed, transfected or infected with the expression vectors of the present invention by methods well-known to those of ordinary skill in the art. Transfection may be accomplished by known methods, such as liposome-mediated transfection, calcium phosphate mediated transfection, microinjection, and electroporation.

Transgenic cells of the subject invention may be obtained by transfection with a polynucleotide comprising an exemplified (or suggested) nucleic acid sequence. Equipped with the teachings herein, the skilled artisan would be able to transfect cells with the exemplifed, as well as future isolated peptide-encoding polynucleotides, to produce cells that make peptides of the subject invention. Progeny cells that retain the peptide-encoding polynucleotide are, of course, within the scope of the subject invention, as are transgenic plants.

The term "transfection" as used herein means an introduction of a foreign DNA or RNA into a cell by mechanical inoculation, electroporation, agroinfection, particle bombardment, microinjection, or by other known methods. The term "transformation" as used herein means a stable incorporation of a foreign DNA or RNA into the cell that results in a permanent, heritable alteration in the cell. Accordingly, the skilled artisan would understand that transfection of a cell may result in the transformation of that cell.

In preferred embodiments, expression of the peptide- and/or toxin-encoding gene results, directly or indirectly, in the intracellular production (and maintenance) of the peptide/protein. Plants can be rendered insect-resistant in this manner. When transgenic/recombinant/transformed/transfected host cells (or contents thereof) are ingested by the pests, the pests will ingest the toxic peptides/proteins. This is one preferred manner in which to cause contact of the pest with the toxin. The result is control (killing or making sick) of the pest. Sucking pests can also be controlled in a similar manner. Alternatively, suitable microbial hosts, e.g., *Pseudomonas* such as *P. fluorescens*, can be applied where target pests are present; the microbes can proliferate there, and are ingested by the target pests.

Where the toxin gene(s) is introduced via a suitable vector into a microbial host, and said host is applied to the environment in a living state, certain host microbes should be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera *Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc*, and *Alcaligenes*; fungi, particularly yeast, e.g., genera *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Also of interest are pigmented microorganisms.

One aspect of the subject invention is the transformation/transfection of plants, plant cells, and other host cells with polynucleotides of the subject invention that express proteins of the subject invention. Plants transformed in this manner can be rendered resistant to attack by the target pest(s).

A wide variety of methods are available for introducing a gene encoding a pesticidal protein into the target host under conditions that allow for stable maintenance and expression of the gene. These methods are well known to those skilled in the art and are described, for example, in U.S. Pat. No. 5,135,867.

For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted. The use of T-DNA for the transformation of plant cells has been intensively researched and described in EP 120 516; Hoekema (1985) In: *The Binary Plant Vector System*, Offset-durkkerij Kanters B. V., Alblasserdam, Chapter 5; Fraley et al., *Crit. Rev. Plant Sci.* 4:146; and An et al. (1985) *EMBO J.* 4:277-287.

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods. If *Agrobacteria* are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in *Agrobacteria*. The intermediate vector can be transferred into *Agrobacterium tumefaciens* by means of a helper plasmid (conjugation). Binary vectors can replicate themselves both in *E. coli* and in *Agrobacteria*. They comprise a selection marker gene and a linker or polylinker which are framed by the right and left T-DNA border regions. They can be transformed directly into *Agrobacteria* (Holsters et al. [1978] *Mol. Gen. Genet.* 163: 181-187). The *Agrobacterium* used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In some preferred embodiments of the invention, genes encoding the bacterial toxin are expressed from transcriptional units inserted into the plant genome. Preferably, said transcriptional units are recombinant vectors capable of stable integration into the plant genome and enable selection of transformed plant lines expressing mRNA encoding the proteins.

Once the inserted DNA has been integrated in the genome, it is relatively stable there (and does not come out again). It normally contains a selection marker that confers on the transformed plant cells resistance to a biocide or an antibiotic, such as kanamycin, G418, bleomycin, hygromycin, or chloramphenicol, inter alia. The individually employed marker should accordingly permit the selection of transformed cells rather than cells that do not contain the inserted DNA. The gene(s) of interest are preferably expressed either by constitutive or inducible promoters in the plant cell. Once expressed, the mRNA is translated into proteins, thereby incorporating amino acids of interest into protein. The genes encoding a toxin expressed in the plant cells can be under the control of a constitutive promoter, a tissue-specific promoter, or an inducible promoter.

Several techniques exist for introducing foreign recombinant vectors into plant cells, and for obtaining plants that stably maintain and express the introduced gene. Such techniques include the introduction of genetic material coated onto microparticles directly into cells (U.S. Pat. No. 4,945,050 to Cornell and U.S Pat No. 5,141,131 to DowElanco, now Dow AgroSciences, LLC). In addition, plants may be transformed using *Agrobacterium* technology, see U.S. Pat. No. 5,177,010 to University of Toledo; U.S. Pat. No. 5,104,310 to Texas A&M; European Patent Application 0131624B1; European Patent Applications 120516, 159418B1 and 176,112 to Schilperoot; U.S. Pat. Nos. 5,149,645, 5,469,976, 5,464,763 and 4,940,838 and 4,693,976 to Schilperoot; European Patent Applications 116718, 290799, 320500 all to Max Planck; European Patent Applications 604662 and 627752, and U.S. Pat. No. 5,591,616, to Japan Tobacco; European Patent Applications 0267159 and 0292435, and U.S. Pat. No. 5,231,019, all to Ciba Geigy, now Novartis; U.S. Pat. Nos. 5,463,174 and 4,762,785, both to Calgene; and U.S. Pat. Nos. 5,004,863 and 5,159,135, both to Agracetus. Other transformation technology includes whiskers technology. See U.S. Pat. Nos. 5,302,523 and 5,464,765, both to Zeneca. Electroporation technology has also been used to transform plants. See WO 87/06614 to Boyce Thompson Institute; U.S. Pat. Nos. 5,472,869 and 5,384,253, both to Dekalb; and WO 92/09696 and WO 93/21335, both to Plant Genetic Systems.

Furthermore, viral vectors can also be used to produce transgenic plants expressing the protein of interest. For example, monocotyledonous plant can be transformed with a viral vector using the methods described in U.S. Pat. No. 5,569,597 to Mycogen Plant Science and Ciba-Giegy, now Novartis, as well as U.S. Pat. Nos. 5,589,367 and 5,316,931, both to Biosource.

As mentioned previously, the manner in which the DNA construct is introduced into the plant host is not critical to this invention. Any method that provides for efficient transformation may be employed. For example, various methods for plant cell transformation are described herein and include the use of Ti or Ri-plasmids and the like to perform *Agrobacterium* mediated transformation. In many instances, it will be desirable to have the construct used for transformation bordered on one or both sides by T-DNA borders, more specifically the right border. This is particularly useful when the construct uses *Agrobacterium tumefaciens* or *Agrobacterium rhizogenes* as a mode for transformation, although T-DNA borders may find use with other modes of transformation. Where *Agrobacterium* is used for plant cell transformation, a vector may be used which may be introduced into the host for homologous recombination with T-DNA or the Ti or Ri plasmid present in the host. Introduction of the vector may be performed via electroporation, tri-parental mating and other techniques for transforming gram-negative bacteria, which are known to those skilled in the art. The manner of vector transformation into the *Agrobacterium* host is not critical to this invention. The Ti or Ri plasmid containing the T-DNA for recombination may be capable or incapable of causing gall formation, and is not critical to said invention so long as the vir genes are present in said host.

In some cases where *Agrobacterium* is used for transformation, the expression construct being within the T-DNA borders will be inserted into a broad spectrum vector such as pRK2 or derivatives thereof as described in Ditta et al., (PNAS USA (1980) 77:7347-7351 and EPO 0 120 515, which are incorporated herein by reference. Included within the expression construct and the T-DNA will be one or more markers as described herein which allow for selection of transformed *Agrobacterium* and transformed plant cells. The particular marker employed is not essential to this invention, with the preferred marker depending on the host and construction used.

For transformation of plant cells using *Agrobacterium*, explants may be combined and incubated with the transformed *Agrobacterium* for sufficient time to allow transformation thereof. After transformation, the *Agrobacteria* are killed by selection with the appropriate antibiotic and plant cells are cultured with the appropriate selective medium. Once calli are formed, shoot formation can be encouraged by employing the appropriate plant hormones according to methods well known in the art of plant tissue culturing and plant regeneration. However, a callus intermediate stage is not always necessary. After shoot formation, said plant cells can be transferred to medium which encourages root formation thereby completing plant regeneration. The plants may then be grown to seed and said seed can be used to establish future generations. Regardless of transformation technique, the gene encoding a bacterial toxin is preferably incorporated into a gene transfer vector adapted to express said gene in a plant cell by including in the vector a plant promoter regulatory element, as well as 3' non-translated transcriptional termination regions such as Nos and the like.

In addition to numerous technologies for transforming plants, the type of tissue that is contacted with the foreign genes may vary as well. Such tissue would include but would not be limited to embryogenic tissue, callus tissue types I, II, and III, hypocotyl, meristem, root tissue, tissues for expression in phloem, and the like. Almost all plant tissues may be transformed during dedifferentiation using appropriate techniques described herein.

A variety of selectable markers can be used, if desired. Preference for a particular marker is at the discretion of the artisan, but any of the following selectable markers may be used along with any other gene not listed herein that could function as a selectable marker.

In addition to a selectable marker, it may be desirous to use a reporter gene. In some instances a reporter gene may be used with or without a selectable marker. Reporter genes are genes that are typically not present in the recipient organism or tissue and typically encode for proteins resulting in some phenotypic change or enzymatic property. An assay for detecting reporter gene expression may then be performed at a suitable time after said gene has been introduced into recipient cells.

The skilled artisan will note that polynucleotides preferred for practicing the subject invention encode proteins (or peptides) capable of expression in cells, localization to cell membrane, and toxin binding. Accordingly, fragments of exemplified sequences as well as functional mutants may equally be used in practicing the subject invention. Such fragments and mutants will be readily obtainable following the teachings herein coupled with the state of the art. For example, using specifically exemplified polynucleotides as probes, useful polynucleotides can be obtained under conditions of appropriate stringency. Standard hybridization conditions include hybridization with nonspecific DNA, such as salmon DNA, at 50° C. and washing at 45° C. To obtain polynucleotides having the lowest detectable homology with the exemplified CR12-MPED (for example), hybridization is conducted under conditions of low standard stringency (30-37° C. and 4-6×SSC). More closely related CR12-MPED like polynucleotides (for example) can be obtained under moderate standard stringency conditions (40-50° C. in 1×SSC).

Having thus described in detail preferred embodiments of the present invention, it is to be understood that the various described embodiments are merely exemplary of the present invention and that many apparent variations thereof are possible without departing from the spirit or scope thereof. Accordingly, one skilled in the art will readily recognize that the present invention is not limited to the specific embodiments described herein.

The description provided in the following examples relates to the preferred method using the available strategy from the published protocols for constructing DNA vectors and the like. Any molecular cloning and recombinant DNA techniques needed would be carried out by standard methods (Sambrook et al., 1995).

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLE 1

Summary of Antagonistic Binding and Toxicity Blocking Assays

Previously, toxin binding regions on Bt-$R_1$ were shown to act as antagonists to Cry1Ab by blocking toxicity (Dorsch et al. 2002; Gomez et al. 2001, Gomez et al. 2003). The CR12-MPED region encoded by the region of Bt-R1a including cad 12 and the MPED was tested using similar experiments. The CR12-MPED region (SEQ ID NO:2, encoded by SEQ ID NO:1) was over-expressed in E. coli and purified. Peptide was mixed with a $LC_{50}$ dosage of Cry1Ab and fed to M. sexta larvae. Cry1Ab toxin was obtained by trypsin activation of the protoxin (Accession Number AAA22330). CR12-MPED was expected to block toxicity when mixed with Cry1Ab toxin and fed to larvae. The bioassay results were quite surprising. The CR12-MPED peptide did not suppress Cry1Ab toxicity but very surprisingly increased the mortality of Manduca larvae fed Cry1Ab. Increased concentrations of CR12-MPED mixed with a constant amount of Cry1Ab fed to the larvae killed more larvae. CR12-MPED peptide enhanced Cry1Ab toxicity. This initial result was confirmed upon further testing. CR12-MPED increases the potency of an already highly active Cry toxin against a susceptible insect.

EXAMPLE 2

M. sexta Bioassay Trial 1

"group1"—9 ng/cm2 Cry1Ab (toxin:peptide ratio 1:0),
"group2"—9 ng/cm2 Cry1Ab plus 9 ng/cm2 CR12-MPED (ratio 1:1),
"group3"—9 ng/cm2 Cry1Ab plus 90 ng/cm2 CR12-MPED (ratio 1:10),
"group4"—9 ng/cm2 Cry1Ab plus 450 ng/cm2 CR12-MPED (ratio 1:50),
"group5"—9 ng/cm2 Cry1Ab plus 900 ng/cm2 CR12-MPED (ratio 1:100),
"group6"—9 ng/cm2 Cry1Ab plus 4500 ng/cm2 CR12-MPED (ratio 1:500)
"group7"—water only as a control.
Each group had 16 replicates.

After 7 days, many larvae in groups 4 and 5 were dead. This was attributed to the possibility that the Tris-HCl buffer, as the CR12-MPED peptide was in 10 mM Tris-HCl (pH 8.0). Alternatively, the CR12-MPED peptide could have been enhancing the toxicity of Cry1Ab. To determine if the high toxicity of the Cry1Ab/CR12-MPED mixture was reproducible, the bioassay experiment was repeated with additional controls.

EXAMPLE 3

M. sexta Bioassay Trial 2

Figures 4A, 4B:
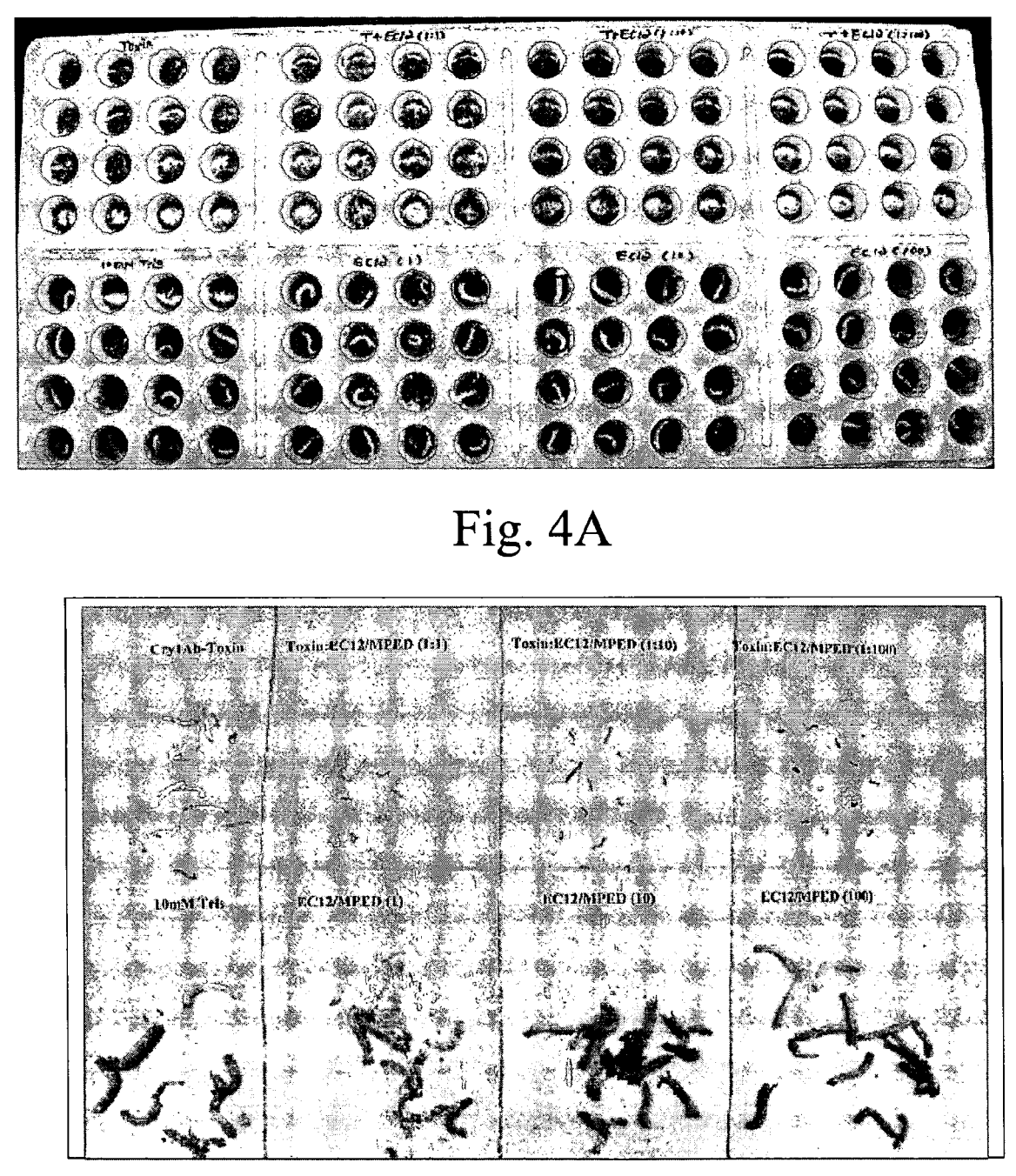

A 1:500 ratio group (i.e., group 6 above) was not included because the 1:50 and 1:100 ratios gave an enhanced effect. Four additional controls were included: 10 mM Tris-HCl (pH 8.0), 9 ng/$cm^2$ CR12-MPED, 90 ng/$cm^2$ CR12-MPED, and 900 ng/$cm^2$ CR12-MPED. In two days, almost all of the larvae in highest concentration of CR12-MPED/Cry1Ab were dead, but the larvae fed with the toxin-only were not dead. The CR12-MPED/Cry1Ab treatment groups showed the same trend as obtained in the first trial. Table 2 shows the percentage mortality for the treatments in both M. sexta trials. CR12-MPED enhanced the potency of B.t. Cry1Ab in both trials. FIGS. 4A and 4B show live and dead larvae from Trial 2. Notice the reduced size of larvae in the all groups fed with combinations of Cry1Ab plus CR12-MPED.

TABLE 2

Bioassay results for Cry1Ab with CR12-MPED to M. sexta larvae.

| | 9 ng/cm² 1Ab | 9 ng 1Ab/cm2 + 9 ng CR12-MPED | 9 ng 1Ab/cm2 + 90 ng CR12-MPED | 9 ng 1Ab/cm2 + 450 ng CR12-MPED | 9 ng 1Ab/cm2 + 900 ng CR12-MPED | 9 ng 1Ab/cm2 + 4500 ng CR12-MPED |
|---|---|---|---|---|---|---|
| Mortality trial 1 | 31.3% | 18.8% | 56.3% | 62.3% | 62.5% | 100% |
| Mortality trial 2 | 31.3% | 45.5% | 100% | | 100% | |

| | 10 mM Tris | 9 ng CR12-MPED | 90 ng CR12-MPED | 900 ng CR12-MPED |
|---|---|---|---|---|
| Mortality trial 1 | 0% | | | |
| Mortality trial 2 | 16.7% | 0% | 0% | 0% |

EXAMPLE 4

Additional Bioassays

Preliminary data suggested that CR12-MPED synergizes *B.t.* Cry1Ab toxicity to *H. virescens*. This is important because *H. virescens* is the major target of *B.t.* cotton.

The ability of the CR12-MPED peptide to function synergistically with other combinations of toxin and pest insects can now be tested, in light of the subject disclosure.

EXAMPLE 5

Synergistic Effect of CR12-MPED Peptide on Mortality of *Heliothis virescens*, *Helicoverpa zea*, *Spodoptera frugiperda*, and *Plutella xylostella* Larvae Fed CR12-MPED Peptide Plus Cry1A Toxins Eggs were hatched and reared on artificial diet on which toxin or/and CR12-MPED peptide were or not added. *Bacillus thuringiensis* toxin (Cry1Aa, 1Ab and 1Ac) were used in $LC_{50}$ dosage according to the *Bacillus thuringiensis* Toxin Specificity Database (see website at glfc.forestry.ca/bacillus). The three toxins as used were obtained by trypsin activation of protoxins (Cry1Aa: DH37 (Accession Number AAA22353); Cry1Ab: NRD12 (Accession Number AAA22330); and Cry1Ac DH73 (Accession AAA22331)). The concentration of each toxin is listed in the following tables. *H. virescens* and *H. zea* neonates were transferred to wells in a bioassay tray containing the diet with or without toxin or/and CR12-MPED peptide. Seven days later, mortality and larval body weight were measured. The mortality and body weight were recorded after seven days feeding with toxins or/and CR12-MPED peptide. Each group has sixteen larvae per treatment. The concentration of CR12-MPED peptide was in various mass ratios relative to Cry1A toxin as shown in Tables 3-7 and in FIGS. 5A-5E. FIGS. 6A-6F are photographs showing surviving *Manduca sexta*, *Heliothis virescens*, *Helicoverpa zea*, *Spodoptera frugiperda*, *B.t.*-susceptible *Plutella xylostella*, and *B.t.*-resistant *Plutella xylostella* larvae fed a mixture of *B.t.* Cry1A toxins and CR12-MPED truncated cadherin peptide.

TABLE 3

| *Manduca Sexta* | | | | |
|---|---|---|---|---|
| | CR12-MPED(0*) | CR12-MPED(1*) | CR12-MPED(10*) | CR12-MPED(100*) |
| H₂O | 0% | 0% | 0% | 0% |
| Cry1Aa (5.2 ng/cm²) | 6.25% | 6.25% | 43.75% | 100% |
| Cry1Ab (9 ng/cm²) | 31.3% | 45.5% | 100% | 100% |
| Cry1Ac (5.3 ng/cm²) | 37.5% | 43.75% | 93.75% | 100% |

*Values in parentheses designate mass ratio of CR12-MPED:Cry protein

TABLE 4

| *Heliothis virescens* | | | | |
|---|---|---|---|---|
| | CR12-MPED(0*) | CR12-MPED(1*) | CR12-MPED(10*) | CR12-MPED(100*) |
| H₂O | 0% | 0% | 0 | 0% |
| Cry1Aa (52 ng/cm²) | 6.25% | 37.5% | 50% | 56.25% |
| Cry1Ab (0.16 ng/cm²) | 0% | 12.5 | 50% | 75% |
| Cry1Ac (4 ng/cm²) | 0% | 56.25% | 75% | 100% |

*Values in parentheses designate mass ratio of CR12-MPED:Cry protein

TABLE 5

| *Helicoverpa zea* | | | | |
|---|---|---|---|---|
| | CR12-MPED(0*) | CR12-MPED(1*) | CR12-MPED(10*) | CR12-MPED(100*) |
| H₂O | 0% | | | 0% |
| Cry1Aa (2.07 ug/cm²) | 68.75% | 70.83% | | |
| Cry1Ab (1.6 ug/cm²) | 0% | 33.33% | | |
| Cry1Ac (0.12 ug/cm²) | 50% | 62.5% | 100% | 100% |

*Values in parentheses designate mass ratio of CR12-MPED:Cry protein

TABLE 6

Spodoptera frugiperda

|  | CR12-MPED(0*) | CR12-MPED(1*) | CR12-MPED(10*) | CR12-MPED(100*) |
|---|---|---|---|---|
| H$_2$O | 6.25% | 12.5% |  | 0% |
| Cry1Aa (50 ng/cm$^2$) | 18.75% | 0% | 18.75% | 6.25% |
| Cry1Ab (50 ng/cm$^2$) | 0% | 25% | 37.5% | 50% |
| Cry1Ac (50 ng/cm$^2$) | 6.25% | 6.25% | 50% | 62.5% |

*Values in parentheses designate mass ratio of CR12-MPED:Cry protein

TABLE 7

Plutella xylostella (non-resistant)

|  | CR12-MPED(0*) | | CR12-MPED(100*) | |
|---|---|---|---|---|
|  | Mortality | Pupating rate | Mortality | Pupating rate |
| H$_2$O | 0% | 100% (2 adults) | 6.25% | 87.5% (1 adult) |
| Cry1Aa (1.4 ng/cm$^2$) | 7.14% | 7.14% | 81.25% | 0% |
| Cry1Ab (3.9 ng/cm$^2$) | 25% | 31.25% | 93.75% | 0% |
| Cry1Ac (0.9 ng/cm$^2$) | 62.5% | 12.5% | 86.87% | 0% |

*Values in parentheses designate mass ratio of CR12-MPED:Cry protein

EXAMPLE 6

Theories Regarding Mechanism(s) of Action

Without being bound by specific theories regarding mechanisms of action, following are possible explanations for the "synergistic" or enhancing effects that peptides of the subject invention have on the insecticidal activity of B.t. proteins. The peptide may bind to the protein (such as a Cry protein) causing a change in conformation of the toxin, thereby allowing cleavage by midgut proteins and facilitating subsequent binding and membrane insertion events. A protein/peptide complex could increase binding to cadherin molecules. In addition, the peptide could increase toxin binding to receptor molecules such as aminopeptidase or other raft-associated proteins sorting in the cell membrane. There is evidence to further support this hypothesis, as cadherin binding increases the affinity of Cry1Ab for aminopeptidase from M. Sexta (Bravo et al. 2004). With the help of a peptide of the subject invention, the toxin could gather or collect on the surface of BBMV and form pores on cell surface. The peptides may function as an adaptor or bridge to connect toxin with cell membrane.

Alternatively or in addition, the peptide may function independently from the Cry toxin, for example. The peptides could exhibit a complete or partial toxic effect elsewhere, separately, or the peptides could function indirectly to enhance the Cry toxin. For example, the peptide could somehow contribute to the stability of the Cry toxin in the insect gut.

The exact mechanism(s) of action, however, are relatively unimportant, as one skilled in the art can now make and use a wide range of embodiments of the subject invention as discussed herein.

EXAMPLE 7

Further Studies

7A. Expression and purification of CR12-MPED peptide in E. coli. Two primers were designed with restriction sites of Nco I and Xho I according to BtR$_{1a}$ CR12-MPED sequence. CR12-MPED encoding Bt-R$_{1a}$ ($^{1362}$Ile-Pro$^{1567}$) was cloned into pET-30a(+) vector (Novagen). The vector pET-30a(+)/CR12-MPED was transferred into E. coli strain BL21/pRIL. Target protein fused with 6×His-tag at both N- and C-termini was over-expressed by 1 mM IPTG induction when the culture OD$_{600}$ reached 0.5-0.6. The culture was harvested 4 hours after induction. CR12-MPED purification was according to "Protocol7" in The QIAexpressionist (2nd Edition, summer 1992, QIAGEN) with minor modifications. The resulting peptide was dialyzed against 10 mM Tris-HCl (pH 8.0) and confirmed by 15% SDS-PAGE and western blot with anti-BtR$_1$ serum (1:5000). The CR12-MPED peptide was used in binding competition assays. The PVDF membrane dotted with S2 cells expressing truncated cadherin was incubated with CR12-MPED peptide and $^{125}$I-Cry1Ab toxin in a 500:1 mass ratio, respectively. CR12-MPED was also tested with Cry1 toxins in insect bioassays (described below).

7B. Insect bioassays. The LC$_{50}$ for Cry1Ab against M. sexta neonate larvae is 5 to 10 ng/cm2 (see website: glfc.cfs.nrcan.gc.ca/bacillus Oct. 1, 2003). In a bioassay, we confirmed this LC$_{50}$ value for Cry1Ab and selected 9 ng/cm2 Cry1Ab for testing the effect of CR12-MPED peptide. Toxin preparations were diluted in deionized water, mixed with varying concentrations of CR12-MPED and then 50 ml applied to the surface of insect diet (Southland Products, Lake Village, Ark.). M. sexta eggs were obtained from Carolina Biologicals. Mortality was scored after 7 days.

H. virescens and Helicoverpa zea eggs were obtained from Benzon Research and bioassays conducted as for M. sexta.

7C. Results. We expressed full length and truncated peptides of BtR$_{1a}$ in S2 cells to investigate their involvement in Cry1Ab binding and toxicity. All truncated cadherin constructs contained the signal leader peptide as well as the transmembrane and cytoplasmic domain for expression on the cell membrane. Truncated cadherin fragment designations included the number of the ectodomain cadherin repeats (CR) they contain and the region included. For example Cad7-12 encodes CR7 and the remainder of Bt-R$_{1a}$ to the carboxy terminus. Transfected S2 cells expressed full length and truncated cadherin fragments, which were recognized by sera against Bt-R$_1$ on immunoblots. As previously reported (Hua et al. 2003), S2 cell-expressed full length Bt-R$_1$ cadherin had a slightly smaller molecular size than Bt-R$_1$ from M. sexta BBMV. Conversely, the Cad7 and Cad7-12 truncated Bt-R$_1$ fragments expressed in S2 cells had a molecular size slightly greater than predicted.

Ligand blots of proteins from S2 transfected cells were probed with $^{125}$I-labeled Cry1Ab toxin. $^{125}$I-Cry1Ab toxin bound to truncated Bt-R$_{1a}$ that contained Cad7-12, 10-12, and 11-12. Expressed truncated proteins that did not contain both CR11 and 12 (i.e. Cad7, Cad 11, Cad12 and Cad-MPED) did not bind $^{125}$I-Cry1Ab on blots. These results agreed with previous ligand blot data of truncated Bt-R$_1$ fragments (Dorsch et al. 2002), which showed Cry1Ab binding to a region that included both CR11 and 12. To verify if the space between toxin binding region and cell membrane was important for toxin binding, CR11 was switched with CR12 and cloned into pIZT vector. Both dot-blot and ligand-blot showed Cad12/11 lost binding with Cry1Ab toxin.

Ligand blotting, which involves denaturing conditions, has been reported to yield Cry toxin binding results that are sometimes inconsistent with toxin binding assays done under native conditions (Daniel et al., 2002; Lee and Dean 1996). To investigate the possibility of alteration by ligand blotting of binding epitopes that are functional under native conditions, we performed dot blotting. S2 cells expressing truncated cadherin fragments were dotted on PVDF filters and $^{125}$I-Cry1Ab toxin binding tested. In agreement with the ligand blot experiments, proteins containing Bt-R$_1$ ectodomains CR11 and 12 (full length cadherin, Cad7-12, Cad10-12, Cad11-12) specifically bound $^{125}$I-Cy1Ab. Peptide expressed from Cad12 also bound toxins, which was a surprise since it did not bind toxin on blots. Cad7 and Cad11 did not bind Cry1Ab. Although Cad12-11 contained both CR11 and CR12 domains, it did not bind to labeled Cry1Ab toxin after they were switched each other. These results suggest that the arrangement among CR11, CR12, and MPED is important for toxin binding. Interestingly, the expressed Cad12 peptide, which contained only ectodomain CR12 and MPED, bound Cry1Ab specifically. This result was not observed in ligand blotting and is evidence that native conditions are necessary for Cry1Ab binding to ectodomain CR12, and that ectodomain CR12 is sufficient for Cry1Ab toxin binding. MPED may also be important in maintaining secondary structure of CR12 (a.k.a. EC12) or possibly collaborates with CR12 in toxin binding. These results identify ectodomain CR12 as a critical Cry1Ab binding epitope on Bt-R$_{1a}$. Interestingly, when radioactivity of the individual dots was counted, the truncated Cad11-12 peptide containing both ectodomain CR11 and 12 bound more Cry1Ab toxin than any other expressed truncated peptide, including full length cadherin (data not shown).

To quantify Cry1Ab binding to expressed Bt-R$_{1a}$ fragments, Cry1Ab binding saturation assays were performed with cell suspensions as previously reported (Hua et al. 2004). In agreement with results from dot blotting, cells expressing full-length cadherin, Cad7-12, Cad11-12 and Cad12 bound Cry1Ab. Toxin binding was specific and saturable in all cases, and cells expressing cad11-12 bound more toxin than any other cell sample. Although all Bt-R$_{1a}$ fragments binding Cry1Ab displayed the same binding affinity (Table 8), the concentration of binding sites was higher for Cad11-12 and Cad12 than for Cad7-12 or full-length cadherin. Furthermore, Cad11-12 had about 3-fold higher concentration of binding sites than Cad12. These results indicate that in full length Bt-R1 conformational limitations may exist that prevent maximal binding of Cry1Ab, and that both CR11 and CR12 contain Cry1Ab binding epitopes.

TABLE 8

Dissociation constants (K$_{com}$) and concentration of receptors (B$_{max}$) calculated from $^{125}$I-Cry1Ab toxin binding saturation assays

| BT-R$_1$ Cad fragment | K$_{com}$ (nM) ± error | B$_{max}$ (fmoles/mg protein) ± error |
|---|---|---|
| 7-12 | 2.05 ± 0.15 | 505.65 ± 22.09 |
| Cad full | 3.55 ± 1.25 | 625.36 ± 14.76 |
| 12 | 2.87 ± 0.84 | 1407.09 ± 44.73 |
| 11-12 | 3.52 ± 0.99 | 3319.54 ± 626.94 |

It was previously reported that Bt-R$_{1a}$ was a functional Cry1A toxin receptor and induced cell death when expressed in S2 cells (Hua et al. 2004). To investigate the role of ectodomains CR11 and 12 in Cry1Ab toxicity, flow cytometry was used to quantitatively measure the percentage of cytotoxic response induced by Cry1Ab in S2 cells expressing different truncated fragments. Co-expression with GFP provided a method to monitor transfection efficiency, and propidium iodide (PI) was used to detect dead cells. Cytotoxicity was quantified using a formula previously reported (Hua et al. 2004) that relates both transfection and cytotoxicity to background cell death in control (mock transfected) cells. Cry1Ab was cytotoxic to cells expressing Cad7-12, Cad10-12, Cad11-12, Cad12 and full length Bt-R$_{1a}$ cadherin. On the other hand, Cry1Ab was not toxic to S2 cells expressing Cad7, Cad11, Cad12-11 and Cad-MPED. There were no significant differences among the toxicities of Cry1Ab on S2 cells expressing Cad7-12, Cad10-12, Cad11-12, Cad12, and full cadherin. These results (summarized in Table 9) are evidence that ectodomain CR 12 is the functional receptor epitope for Cry1Ab in Bt-R$_{1a}$.

TABLE 9

Summary

| | $^{125}$I-Cry1Ab binding | | |
|---|---|---|---|
| Construct | Denatured | native | Toxicity |
| Cad/full | + | + | + |
| Cad7 | − | − | − |
| Cad7-12 | + | + | + |
| Cad10-12 | + | + | + |
| Cad11-12 | + | + | + |
| Cad12-11 | − | − | NT |
| Cad12 | − | + | + |
| Cad11 | − | − | − |
| Cad-MPED | − | − | − |

To confirm the importance of Cad12-MPED region in toxin binding, Cad12-MPED peptide was used as a competitor in dot-blot assays against $^{125}$I-Cry1Ab. Cad12-MPED was expressed in *E. coli* and purified using immobilized metal affinity chromatography. Cad12-MPED peptide competed Cry1Ab toxin binding to full-length cadherin, and truncated cadherins 7-12, 10-12, 11-12 and 12. This result was further evidence that cadherin CR12 domain is necessary and sufficient for toxin binding. CR12 contains the key Cry1Ab binding site on Bt-R$_{1a}$ cadherin.

EXAMPLE 8

Summary of Results of Peptide CR12-MPED Enhancing Toxicity of Various Cry1A Proteins Against Various Lepidopterans BtR$_{1a}$ was cloned into the insect cell expression vector pIZT-V5-His (Invitrogen). A fragment of BtR$_{1a}$ extending from cadherin repeat (CR) 12 through the membrane proximal extracellular domain (MPED) was cloned into pET30a and expressed in *Escherichia coli*. The 27-kDa expressed peptide called CR12-MPED was partially purified from inclusion bodies. Surprisingly feeding insect larvae CR12-MPED peptide with Cry1 toxin increased the toxicity of Cry1A toxins to insect larvae.

The CR12-MPED peptide was tested in combination with Cry1A toxins against lepidopteran larvae representing a range of Cry1A toxin susceptibilities. The following insects were tested: *Manduca sexta* (tobacco hornworm), *Heliothis virescens* (tobacco budworm), *Helicoverpa zea* (cotton bollworm, corn earworm), *Spodoptera frugiperda* (fall armyworm), and *Pseudoplusia includens* (soybean looper).

Cry1Aa, Cry1Ab and Cry1Ac toxins were tested with CR12-MPED using diet-surface treatments, early first instar larvae and a 7 day bioassay period.

EXAMPLE 9

Peptide CR12-MPED Enhances Toxicity of Cry1Ab and Cry1Ac Proteins Against *Manduca sexta*

In bioassays against *M. sexta*, CR12-MPED increased mortality from 1.0±1.0% for 2 ng Cry1Ab/cm$^2$ treatments to 26.0±5.5% mortality at a 1:100 Cry1Ab:CR12-MPED mass ratio. As the toxin concentration was increased to 4 ng/cm$^2$ CR12-MPED increased mortality from 4.2±1.1% to 82.3±6.8% (P<0.01). CR12-MPED was inactive alone in all bioassays.

CR12-MPED also enhanced potency of Cry1Ac against *M. sexta* larvae. For example while 2 ng Cry1Ac/cm$^2$ killed 13.5±6.5% of the larvae, Cry1Ac:CR12-MPED ratios of 1:10 and 1:100 mortality increased morality to 63.5±17.8% (P<0.05) and 93.8±3.1% (P<0.005), respectively.

EXAMPLE 10

Peptide CR12-MPED Enhances Toxicity of Cry1Ac Against *Heliothis virescens*

CR12-MPED enhances Cry1Ac toxicity to *H. virescens* (tobacco budworm). Neonate larvae were fed Cry1Ac with or without CR12-MPED. At a Cry1Ac concentration of 3 ng/cm$^2$ diet mortality was 8.4±2.1% (toxin only); with inclusion of 300 ng/cm$^2$ of CR12-MPED mortality was increased to 83.4±6.3% (P<0.01). At a Cry1Ac concentration of 6 ng/cm$^2$, CR12-MPED peptide greatly enhanced Cry1Ac toxicity to *H. virescens* larvae from 46.7±9.9% (toxin only) to 88.5±5.5% (with either 1:10 or 1:100 CR12-MPED ratio) (P<0.05).

EXAMPLE 11

Peptide CR12-MPED Enhances Toxicity of Cry1Ac Proteins Against *Helicoverpa zea*

*H. zea* (cotton bollworm, corn earworm, tomato fruitworm) has a wide host range, attacking many vegetables, fruits, and cotton. *B.t.* transgene crops are not as effective at controlling *H. zea* as they are other pests. This is because Cry1A toxins are less effective against *H. zea* than other target pests. *H. zea* is not as sensitive to Cry1Ac as *H. virescens* or *M. sexta*. Therefore, this pest was selected to determine if CR12-MPED peptide could enhance *B.t.* activity.

In this experiment, 50 ng/cm$^2$, 60 ng/cm$^2$ and 120 ng/cm$^2$ of Cry1Ac were used to test CR12-MPED. Cry1Ac toxin did not kill the larvae efficiently. At 50 ng or 60 ng/cm$^2$ dosages, only 5.2±2.8% of the larvae were killed, compared to 0% (for toxin only). However, the addition of a 1:10 ratio of CR12-MPED increased morality to 56.3±8.3% (P<0.05) and 42.7±3.8% (P<0.01). If the toxin dosage was increased to 120 ng/cm$^2$, it killed 24.0±2.8% of *H. zea* larvae while an equal proportion of added CR12-MPED increased morality to 47.9±5.5% (P<0.05). A ten-fold amount peptide increased the mortality to 85.4±2.8 (P<0.001).

EXAMPLE 12

Peptide CR12-MPED Enhances Toxicity of Cry1Ab, Cry1Ac, and Cry1C Proteins Against *Spodoptera frugiperda*

*Spodoptera frugiperda* is not susceptible to Cry1A toxins (LC$_{50}$>2000 ng/cm$^2$ dosage; see, e.g., "glfc.forestry.ca/bacillus" website. However, when Cry1Ab or Cry1Ac were combined with CR12-MPED at 1:1 and 1:10 ratios (toxin:CR12-MPED) mortality was increased, and larvae fed combinations of CR12-MPED and Cry1Ab or Cry1Ac were severely stunted in growth. *S. frugiperda* is more susceptible to Cry1Ca (LC$_{50}$ 1144 (813-3227) ng/cm$^2$) compared to Cry1A toxins. Cry1Ca protoxin (GENBANK Accession Number CAA30396), tested at 150 and 300 ng/cm$^2$, killed 6% and 19% of larvae. Addition of CR12-MPED increased morality to 31% and 41%. This is an important observation because there is no published report of Cry1Ca interaction with *M. sexta* cadherin.

EXAMPLE 13

Summary of CR12-MPED Binding Studies and Conclusions Regarding Toxin Enhancement Overall, CR12-MPED enhances or potentiates the toxicity of Cry1A and Cry1C toxins against susceptible and tolerant insects. In vitro, CR12-MPED binds to toxin forming large-sized protein clusters. These protein clusters still bind specifically to midgut brush border.

EXAMPLE 14

Peptide CR11-MPED Enhances Toxicity of Cry1Ab Against *Manduca sexta*

The CR11-MPED (SEQ ID NO:4; SEQ ID NO:3 is the DNA) region of BtR$_{1a}$ were cloned into pET30 and expressed in *E. coli*. The CR11-MPED region consists of CR11 in front of CR12-MPED. Peptide was solubilised from inclusion bodies and tested in bioassays with purified Cry1Ab toxin. Peptide CR11-MPED peptide fed with Cry1Ab toxin to *M. sexta* larvae was more toxic to larvae than toxin alone (FIG. 7). The enhancement effect was dose dependent; increasing with higher ratios of CR11-MPED:Cry1Ab.

EXAMPLE 15

Peptide CR11-MPED Enhances Toxicity of Cry1Ac Against Soybean Loopers

As discussed in more detail in Example 16, the CR11-MPED peptide also increased Cry1Ac toxicity to soybean loopers (FIG. 8).

EXAMPLE 16

Comparison of the Ability of CR1-3, CR11-MPED, and CR12-MPED Peptides to Enhance Cry1Ac Against Soybean Loopers The peptide CR1-3 (SEQ ID NO:6; SEQ ID NO:5 is the DNA) was constructed as a negative control with the expectation that it would not enhance toxicity based on the lack of a Cry1Ab binding site on the peptide. However, CR1-3 was surprisingly found to be equal to CR12-MPED in the capacity to increase Cry1Ac toxicity to soybean looper (FIG. 8).

The CR11-MPED and CR1-3 regions of $BtR_{1a}$ were cloned into pET30 and expressed in *E. coli*. All peptides were expressed and purified using standard methodology. Purified peptides were run on SDS page using standard methodology. Concentrations of the indicated samples are as follows: CR11-MPED (0.279 mg/ml); CR12-MPED (2.106 mg/ml); CR1-3 (1.809 mg/ml), Ano-Cad (0.50 mg/ml), Ano-PCAP (0.78 mg/ml) and SlyD (0.046 mg/ml). 12.5 ng/cm$^2$ of Cry1Ac was bioassayed with or without different peptides in 1:1, 1:10 and 1:100 ratio. Soybean looper neonates were set in bioassay trays, with each group having 62 larvae. The Ano-Cad, Ano-PCAP, and SlyD peptides are discussed in the following Example.

EXAMPLE 17

Preparation of Peptides Ano-Cad and Ano-PCAP from Mosquito Cadherin Proteins, and Preparation of Peptide SlyD Mosquitoes are dipterans, as opposed to lepidopterans as tested above. Because selected mosquito cadherin proteins have low amino acid similarity to BtR$_1$, peptide fragments from mosquito cadherins were expected to be less likely to enhance a toxin's effect in lepidopteran larvae, thereby serving as a negative cadherin control. Additionally, mosquito cadherin fragments could be tested for toxin-enhancing properties in mosquitoes.

Two full-length cDNAs encoding cadherin-type proteins were cloned and sequenced from the mosquito *Anopheles gambiae*. The cloned cDNA nucleotide sequences correspond to sequences deposited by the *Anopheles gambiae* genome sequencing project at *A. gambiae* loci. Fragments similar in size and location to the CR12-MPED region of $BtR_{1a}$ were cloned into pET30 vector and expressed in *E. coli*. The cDNA fragments, designated, Ano-Cad and Ano-PCAP, cloned in pET are identical to the DNA sequences of *A. gambiae* loci XM_312086 and XM_321513, respectively.

SEQ ID NO:7 shows the nucleotide sequence of the putative cell adhesion protein of *Anopheles gambiae* (NCBI LOCUS XM_321513). SEQ ID NO:8 shows the corresponding amino acid sequence. SEQ ID NO:9 shows the nucleotide sequence encoding the truncated putative cell-adhesion protein region of the *Anopheles gambiae* protein. This truncated peptide is referred to herein as PCAP (putative cell-adhesion protein) or Ano-PCAP, which has 213 amino acid residues, and is approximately 24,417 Daltons (theoretical pI=4.96). SEQ ID NO:10 shows the truncated PCAP region of the *Anopheles gambiae* protein. This sequence is for the peptide expressed in *E. coli* strain BL21/DE3/pRIL having the DNA cloned into the pET-30a vector.

SEQ ID NO:11 shows the full-length *Anopheles gambiae* cDNA cadherein sequence. BLAST search with the sequence matches the DNA and predicted protein sequence for a partial *Anopheles gambiae* cDNA (NCBI Locus XM_312086). SEQ ID NO:12 shows the "Ano-Cad"-encoding fragment of SEQ ID NO:11 that was cloned into the pET-30 vector and expressed in *E. coli* strain BL21/DE3. SEQ ID NO:13 shows the full-length *Anopheles gambiae* cadherin protein encoded by SEQ ID NO:11. Residues 1358-1569 of SEQ ID NO:13 correspond to the "Ano-Cad" peptide encoded by SEQ ID NO:12.

SlyD is 21-a kDa histidine-rich *E. coli* protein that frequently co-elutes with other proteins from immobilized metal affinity column (IMAC). Because a similar-sized protein was detected in some eluates, SlyD from *E. coli* was prepared for testing as well.

EXAMPLE 18

Comparison of the Ability of Ano-PCAP, Ano-Cad, and SlyD Peptides to Enhance Cry1Ac Against Soybean Loopers As shown in FIG. 8, Ano-PCAP (SEQ ID NO:10) induced some increase in toxicity, whereas the Ano-Cad peptide (residues 1358-1569 of SEQ ID NO:13) did not. SlyD did not have an enhancing effect.

EXAMPLE 19

Figure 9:
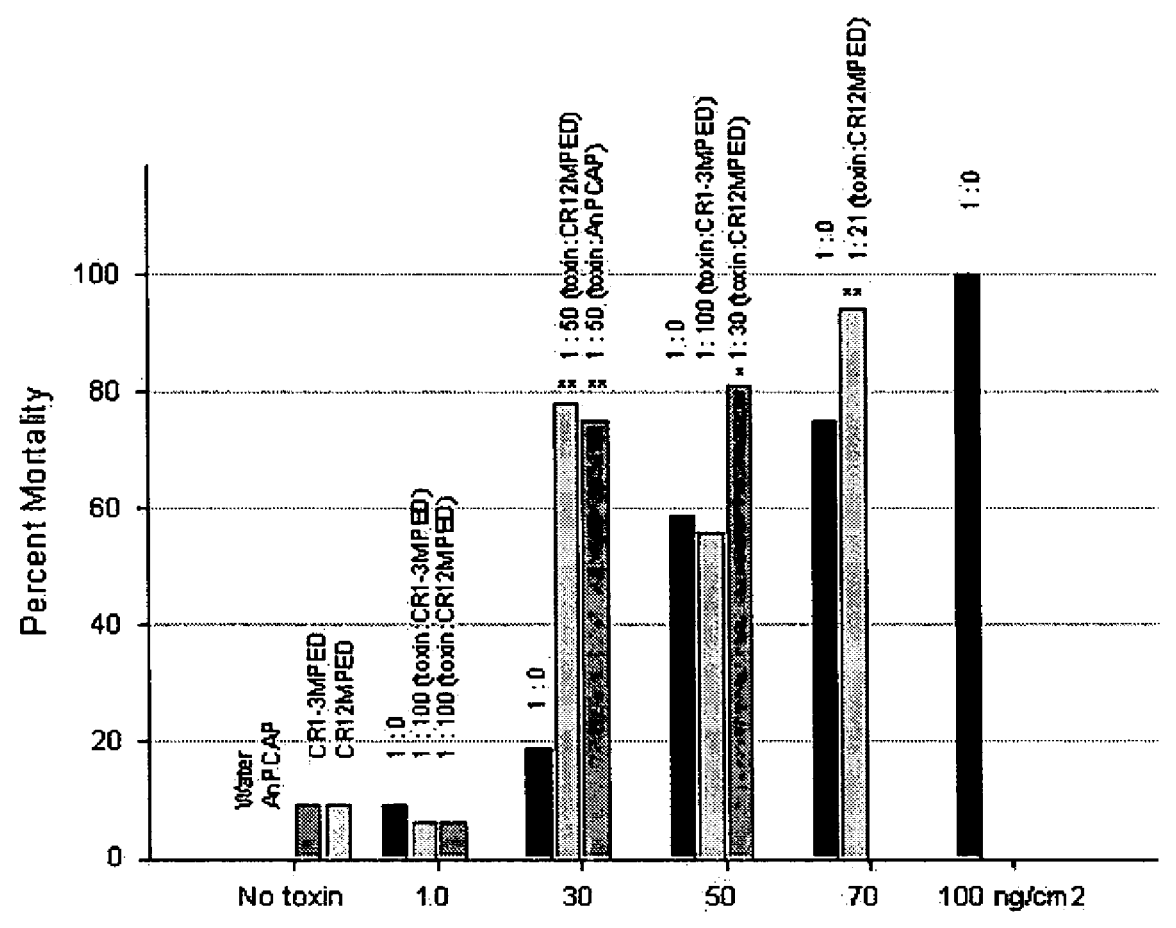

Comparison of the Ability of Ano-PCAP, CR12-MPED, and CR1-3 Peptides to Enhance Cry2Aa Against Soybean Loopers Cry2Aa protoxin (non-truncated) (GENBANK Accession Number M31738) was fed to soybean looper larvae (neonates) with CR12-MPED, CR1-3, or Ano-PCAP (SEQ ID NO:10). Both CR12-MPED and Ano-PCAP increased Cry2Aa toxicity to the larvae. See FIG. 9. Ratios of toxin: sample are indicated on the graph. CR1-3 and CR12-MPED were Ni-NTA column elution containing 0.25 M imidazole, while Ano-PCAP was purified by ion exchange chromatography (Q sepharose). Cry2Aa protoxin was expressed in *E. coli* and purified by ion exchange chromatography (Q sepharose). Single asterisks (*) denotes 0.05<P<0.1 while double asterisks (**) denotes P<0.05 in Chi square statistical calculation comparing toxin only treatment with toxin and sample treatment. CR1-3 did not enhance Cry2Aa toxicity. Both CR12-MPED and Ano-PCAP were able to significantly enhance Cry2Aa toxicity.

EXAMPLE 20

Peptides CR11-MPED, CR12-MPED, CR1-3, and Ano-Cad Have Stand-Alone Activity Against Rootworms, Cry1Aa Surprisingly Has Activity Against Rootworms (Coleopterans)

A Cry1Aa protein (GENBANK Accession Number AAA22353), which is a toxin produced in *Bacillus thuringiensis* (*B.t.*), was tested as protoxin and trypsin-treated forms to determine its level of anti-rootworm (*Diabrotica* spp.; coleopterans) activity, if any. The expectation was that this toxin would not be active against this coleopteran, as Cry1 toxins (including Cry1Aa) are known to be "lep active" toxins (toxins with proven activity against caterpillars or lepidopterans). See e.g. Hofte et al. (1989). This protein was surprisingly found to have activity against rootworms. Thus, methods of using Cry1Aa for controlling rootworms are an aspect of the subject invention.

Surprisingly, in the course of this experimentation, it was also found that the CR11-MPED and CR12-MPED peptide have stand-alone activity against rootworms. Other cadherin-like peptides eg. CR1-3 and Ano-Cad were also tested and found to have significant toxicity against rootworms, albeit at lower toxicity (CR11-MPED≈R12-MPED>CR1-3≈Ano-Cad). As the testing and data set forth herein are not exhaustive, the subject invention thus includes the use of peptides of the subject invention, alone, for controlling insects. This methodology is yet another aspect of the subject invention. In preferred embodiments of this aspect of the subject invention, "stand-alone" peptides are used to control coleopterans (which include grubs and beetles).

20.A—Preparation of Cry1Aa, CR11-MPED, CR12-MPED, CR1-3, and Ano-Cad and Rootworm Bioassays.

The Cry1Aa construct (cry1Aa gene in pKK223-3 vector) was obtained from Donald H. Dean (The Ohio State University). Toxin was expressed in E. coli and purified by HPLC. The toxin was concentrated and dialyzed against distilled water.

All peptides were over-expressed in E. coli as an inclusion body. Inclusion bodies were extracted from the bacteria and solubilized in 10 mM NaOH. Insoluble materials were removed by centrifugation. The supernatant was applied to Q-sepharose column (30 mM $Na_2CO_3$ pH 10.0), and the flow-through fractions containing CR11-MPED were collected because CR11-MPED form large aggregates that fail to bind to the anion exchange column. The fractions were pooled and centrifuged again. The supernatant was concentrated by filtration (Amicon) and dialyzed against distilled water. Rootworm eggs were purchased from Lee French (French Agricultural Research Inc., Minnesota). Southern Corn Rootworm diet was purchased from Bio-Serv.

Bioassays were performed on neonate larvae of Southern Corn Rootworm (*Diabrotica undecipunctata*). The toxin/peptides was diluted in distilled water and applied on the artificial diet in plastic bioassay trays and air dried. Six larvae were put in each well, and 24 larvae were tested at each toxin dose in Trial 1. In Trial 2, four larvae were put in each well, and 16 larvae were tested at each toxin dose. The bioassays were done at room temperature (23° C.). Mortality was recorded on Day 11 in Trial 1 and Day 10 in Trial 2.

20.B—Toxicity of Cry1Aa, CR11-MPED, CR12-MPED, CR1-3, and Ano-Cad on *D. undecipunctata*.

In Trial 1, 29% mortality was observed at a concentration of 200 g/cm² Cry1Aa protoxin and 50% mortality was observed at a concentration of 250 µg/cm². Higher mortality was recorded for trypsin-treated Cry1Aa. 72% mortality was observed at a concentration of 100 µg/cm² trypsin-treated Cry1Aa and 67% mortality was observed at a concentration of 150 µg/cm². In Trial 2, 100% mortality was achieved with Cry1Aa protoxin at a concentration of 300 µg/cm². Background mortality was between 6 and 8% in both trials. These results (summarized in Table 10) demonstrated that Cry1Aa has insecticidal activity against rootworms.

TABLE 10

Bioassay results for Cry1Aa protoxin and trypsin-treated toxin to *D. undecipunctata* larvae

|  | 200 µg/cm² Cry1Aa protoxin | 250 µg/cm² Cry1Aa protoxin |
|---|---|---|
| Mortality Trial 1 | 29% | 50% |
|  | 100 µg/cm² trypsin-treated Cry1Aa | 150 µg/cm² trypsin-treated Cry1Aa |
| Mortality Trial 1 | 72% Distilled $H_2O$ | 67% |
| Mortality Trial 1 | 8% 200 µg/cm² Cry1Aa protoxin | 300 µg/cm² Cry1Aa protoxin |
| Mortality Trial 2 | 0% Distilled $H_2O$ | 100% |
| Mortality Trial 2 | 6% |  |

The toxicity of the peptides (CR11-MPED, CR12-MPED, CR1-3, and Ano-Cad) towards the rootworm larvae was unexpected because initial tests on soybean looper larvae showed no toxic activity when the peptides were applied alone. Also, a concentration of 100 µg/cm² CR12-MPED did not cause any mortality or growth inhibition to *H. zea* neonates.

In Trial 1, 25 µg/cm² CR11-MPED killed 8%, 50 µg/cm² CR11-MPED killed 8%, 100 µg/cm² CR11-MPED killed 12%, 150 µg/cm² CR11-MPED killed 79%, 200 µg/cm² CR11-MPED killed 83%, and 250 µg/cm² CR11-MPED killed 92% of the larvae. In the same trial, 25 µg/cm² CR12-MPED killed 8%, 50 µg/cm² CR12-MPED killed 21%, 100 µg/cm² CR12-MPED killed 21%, 150 µg/cm² CR12-MPED killed 96%, 200 µg/cm² CR12-MPED killed 92%, and 250 µg/cm² CR12-MPED killed 83% of the larvae.

In Trial 2, 125 µg/cm² CR11-MPED killed 87%, 150 µg/cm² CR11-MPED killed 75%, 200 µg/cm² CR11-MPED killed 88% of the larvae. In the same trial, 125 µg/cm² CR1-3 killed 6%, 150 µg/cm² CR1-3 killed 63%, 200 µg/cm² CR1-3 killed 44% of the larvae, while 125 µg/cm² Ano-Cad killed 31%, 150 µg/cm² Ano-Cad killed 38%, 200 µg/cm² Ano-Cad killed 50% of the larvae. Background mortality was between 6 and 8% in both trials. These results (summarized in Table 11) demonstrated the stand-alone insecticidal activity of these peptides against rootworms.

TABLE 11

Bioassay results for CR11-MPED, CR12-MPED, CR1-3, and Ano-Cad to *D. undecipunctata* larvae

|  | 25 µg/cm² C11-MPED | 50 µg/cm² C11-MPED | 100 µg/cm² C11-MPED | 150 µg/cm² C11-MPED | 200 µg/cm² C11-MPED | 250 µg/cm² C11-MPED |
|---|---|---|---|---|---|---|
| Mortality Trial 1 | 8% | 8% | 12% | 79% | 83% | 92% |

|  | 25 µg/cm² CR12-MPED | 50 µg/cm² CR12-MPED | 100 µg/cm² C12-MPED | 150 µg/cm² CR12-MPED | 200 µg/cm² CR12-MPED | 250 µg/cm² C12-MPED |
|---|---|---|---|---|---|---|

TABLE 11-continued

Bioassay results for CR11-MPED, CR12-MPED, CR1-3, and Ano-Cad to *D. undecipunctata* larvae

| Mortality Trial 1 | 8% | 21% | 21% | 96% | 92% | 83% |
|---|---|---|---|---|---|---|

| | Distilled H$_2$O |
|---|---|
| Mortality Trial 1 | 8% |

| | 125 µg/cm$^2$ C11-MPED | 150 µg/cm$^2$ C11-MPED | 200 µg/cm$^2$ C11-MPED |
|---|---|---|---|
| Mortality Trial 2 | 87% | 75% | 88% |

| | 125 µg/cm$^2$ CR1-3 | 150 µg/cm$^2$ CR1-3 | 200 µg/cm$^2$ CR1-3 |
|---|---|---|---|
| Mortality Trial 2 | 6% | 63% | 44% |

| | 125 µg/cm$^2$ Ano-Cad | 150 µg/cm$^2$ Ano-Cad | 200 µg/cm$^2$ Ano-Cad | Distilled H$_2$O |
|---|---|---|---|---|
| Mortality Trial 2 | 31% | 38% | 50% | 6% |

EXAMPLE 21

Mortality of Soybean Looper (*Pseudoplusia includens*) to Mixtures of CR12-MPED and Cry1Aa Protoxin or Trypsin-digested Cry1Aa The Cry1Aa construct (cry1Aa gene in pKK223-3 vector) was obtained from Donald H. Dean (The Ohio State University). Toxin was expressed in *E. coli* and purified by HPLC. Table 12 shows the diet overlay bioassay on the soybean looper (*Pseudoplusia includens*) neonate mortality to Cry1Aa in the forms of either protoxin or trypsin-digested truncated toxin, and with mixtures of CR12-MPED at 1:100 (w/w) ratios. CR12-MPED enhances Cry1Aa toxicity to *P. includens*. At a Cry1Aa protoxin concentration of 2 ng/cm$^2$ diet mortality was 23% (toxin only); with inclusion of 200 ng/cm$^2$ of CR12-MPED mortality was increased to 50%. At a Cry1Aa protoxin concentration of 5 ng/cm$^2$, 500 ng/cm$^2$ CR12-MPED peptide greatly enhanced Cry1Aa protoxin toxicity to *P. includens* larvae from 0% (toxin only) to 88% (P<0.001).

Figure 10A:
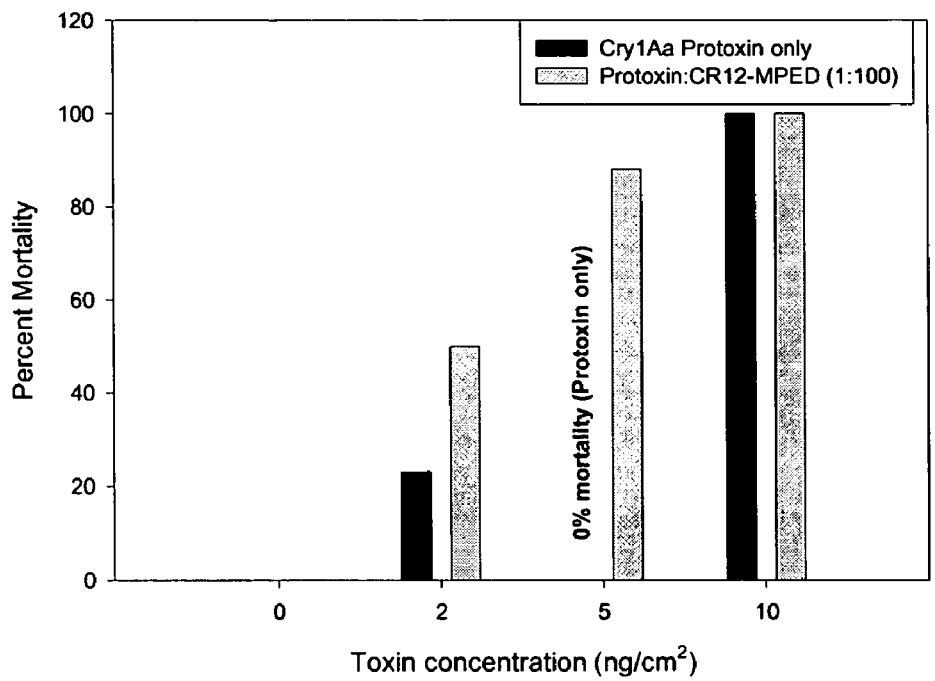
FIG. 10A demonstrates that CR12-MPED peptide was able to enhance the activity of Cry1Aa protoxin, as well as trypsin-digested truncated Cry1Aa (FIG. 10B) against *P. includens*.
Figure 10B:
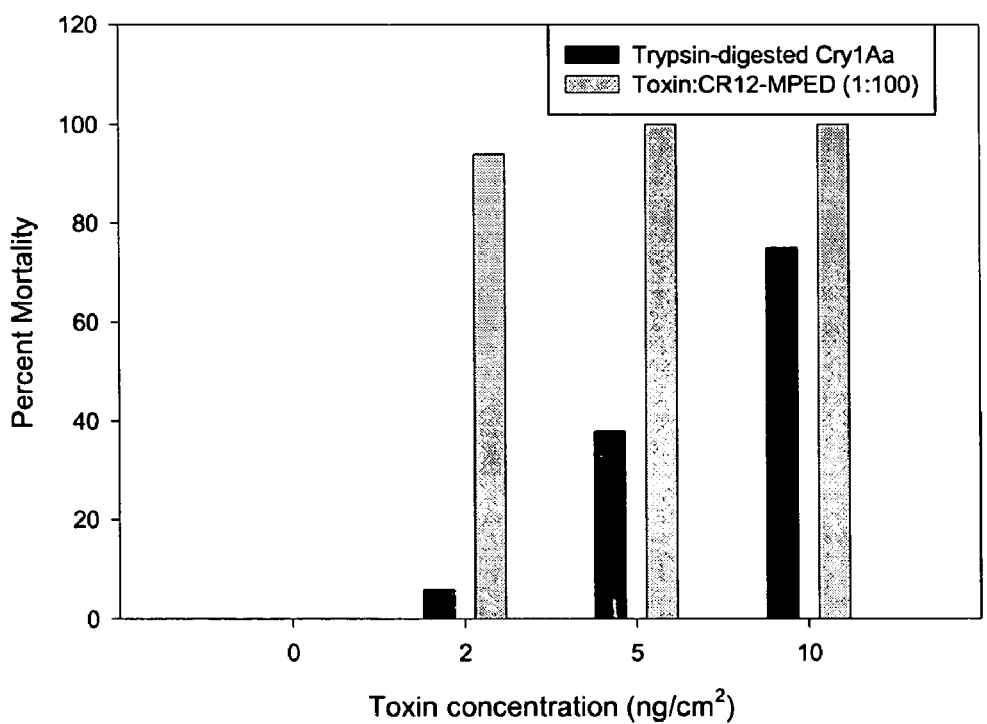

Similar results were obtained using trypsin-digested truncated Cry1Aa. At a Cry1Aa trypsin-digested toxin concentration of 2 ng/cm$^2$ diet mortality was 6% (toxin only); with inclusion of 200 ng/cm$^2$ of CR12-MPED mortality was increased to 94% (P<0.001). At a Cry1Aa trypsin-digested toxin concentration of 5 ng/cm$^2$, 500 ng/cm$^2$ CR12-MPED peptide enhanced Cry1Aa protoxin toxicity to *P. includens* larvae from 38% (toxin only) to 100% (P<0.001). Background mortality was at 0%. These results demonstrated that CR12-MPED peptide was able to enhance the activity of Cry1Aa protoxin (FIG. 10A) as well as trypsin-digested truncated Cry1Aa (FIG. 10B) against *P. includens*.

TABLE 12

Bioassay results for Cry1Aa alone and 1:100 ratio (w/w) mixtures of Cry1Aa:CR12-MPED to *Pseudoplusia includens* larvae

| | 2 ng/cm$^2$ Cry1Aa protoxin | 5 ng/cm$^2$ Cry1Aa protoxin | 10 ng/cm$^2$ Cry1Aa protoxin |
|---|---|---|---|
| Mortality | 23% | 0% | 100% |
| | 2 ng/cm Cry1Aa | 5 ng/cm Cry1Aa | 10 ng/cm$^2$ Cry1Aa |

TABLE 12-continued

Bioassay results for Cry1Aa alone and 1:100 ratio (w/w) mixtures of Cry1Aa:CR12-MPED to *Pseudoplusia includens* larvae

| | protoxin: 200 ng/cm$^2$ CR12-MPED | protoxin: 500 ng/cm$^2$ CR12-MPED | protoxin: 1000 ng/cm$^2$ CR12-MPED |
|---|---|---|---|
| Mortality | 50% | 88% | 100% |
| | 2 ng/cm$^2$ trypsin-digested Cry1Aa | 5 ng/cm$^2$ trypsin-digested Cry1Aa | 10 ng/cm$^2$ trypsin-digested Cry1Aa |
| Mortality | 6% | 38% | 75% |
| | 2 ng/cm$^2$ trypsin-digested Cry1Aa:200 ng/cm$^2$ CR12-MPED | 5 ng/cm$^2$ trypsin-digested Cry1Aa:500 ng/cm$^2$ CR12-MPED | 10 ng/cm$^2$ trypsin-digested Cry1Aa:1000 ng/cm$^2$ CR12-MPED |
| Mortality | 94% | 100% | 100% |
| | Distilled H$_2$O | | |
| Mortality | 0% | | |

EXAMPLE 22

Figure 11:
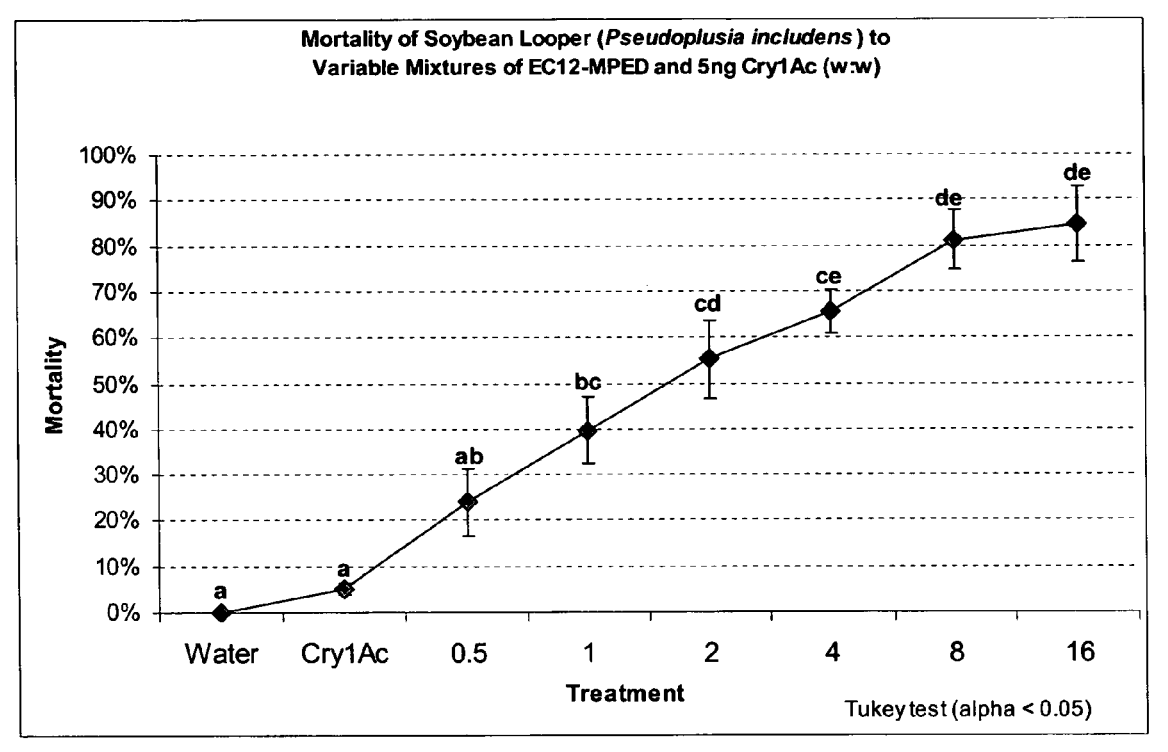

Mortality of Soybean Looper (*Pseudoplusia includens*) to Variable Mixtures of CR12-MPED and Cry1Ac FIG. 11 shows the diet overlay bioassay on the soybean looper (*Pseudoplusia includens*) neonate mortality to the mixture of CR12-MPED and 2.5 ng/cm$^2$ Cry1Ac (w:w) with different toxin:peptide ratios. The mortality was (5.2±1.1) % when only 2.5 ng/cm$^2$ Cry1Ac was applied. When same amount of Cry1Ac mixed with CR12-MPED as 1:1 ratio, the neonate mortality was significantly enhanced to (39.9±7.3) % (P<0.05). The mortality was enhanced by approximately 50% when the toxin:peptide ratio reached 1:2 (55.2±8.5) %.

EXAMPLE 23

Figure 12:
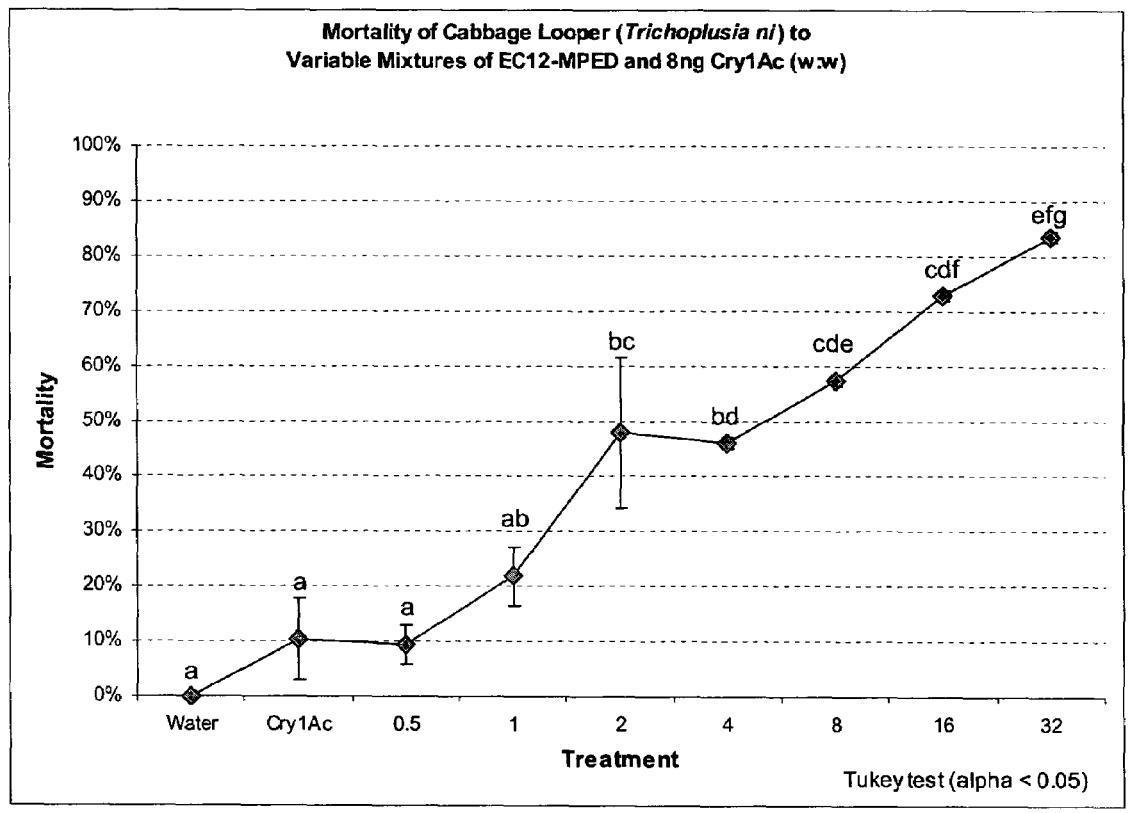
FIG. 12 illustrates results of the diet overlay bioassay on the cabbage looper (*Trichoplusia ni*) neonate mortality to the mixture of CR12-MPED and 8 ng/cm$^2$ Cry1Ac with different toxin:peptide ratios.

Mortality of Cabbage Looper (*Trichoplusia ni*) to Variable Mixtures of CR12-MPED and Cry1Ac FIG. 12 shows the diet overlay bioassay on the cabbage looper (*Trichoplusia ni*) neonate mortality to the mixture of CR12-MPED and 4 ng /cm$^2$ Cry1Ac (w:w) with different toxin:peptide ratios. The mortality was (10.4±7.5) % when only 4 ng /cm$^2$ Cry1Ac was applied. When same amount of Cry1Ac mixed with CR12-MPED as 1:2 ratio, the neonate mortality was significantly enhanced to (47.9±13.5) % (P<0.05). The mortality was significantly over 50% when toxin:peptide ratio reached 1:8 (57.3±1.0) % (P<0.05).

REFERENCES

Abdullah, M. A. F., O. Alzate, M. Mohammad, R. J. McNall, M. J. Adang, and D. H. Dean. 2003. Introduction of Culex toxicity into *Bacillus thuringiensis* Cry4Ba by protein engineering. Appl. Environ. Microbiol. 69:5343-5353

Abdullah, M. A. F., and D. H. Dean. 2004. Enhancement of Cry19Aa mosquitocidal activity against *Aedes aegypti* by mutations in the putative loop regions of domain II. Appl. Environ. Microbiol. 70:3769-3771

Adang, M. J., Luo, K., 2003. Methods and materials for identifying novel pesticide agents, U.S. Pat. No. 6,586,197 B1.

Banks, D., Hua, G. Adang, M. J., 2003. Cloning of a *Heliothis virescens* 110 kDa aminopeptidase N and expression in *Drosophila* S2 cells. Insect Biochem. Mol. Biol. 33, 499-508.

Bradford, M., 1976. A rapid and sensitive method for the quantitation of microgram quantities of protein utilizing the principle of protein-dye binding. Anal. Biochem. 72, 248-254.

Bravo, A., Gomez, I., Conde, J., Munoz-Garay, C., Sanchez, J., Miranda, R., Zhuang, M., Gill, S. S., Soberon, M. 2004. Oligomerization triggers binding of a *Bacillus thuringiensis* Cry1Ab pore-forming toxin to aminopeptidase N receptor leading to insertion into membrane microdomains. Biochimica et Biophysica Acta. 1667, 38-46.

Bulla, L. A., 2002a. Methods for screening candidate pesticides using a receptor that binds *Bacillus thuringiensis* toxin, U.S. Pat. No. 6,423,502.

Bulla, L. A., 2002b. Receptor for a *Bacillus thuringiensis* toxin, U.S. Pat. No. 6,455,266.

Daniel, A., Sangadala, S., Dean, D. H. Adang, M. J., 2002. Denaturation of either *Manduca sexta* aminopeptidase N or *Bacillus thuringiensis* Cry1A toxins exposes epitopes hidden under nondenaturing conditions. Appl. Environ. Microbiol. 68, 2106-2112.

Dorsch, J. A., Candas, M., Griko, N., Maaty, W., Midboe, E., Vadlamudi, R. Bulla, L., 2002. Cry1A toxins of *Bacillus thuringiensis* bind specifically to a region adjacent to the membrane-proximal extracellular domain of BT-R$_1$ in *Manduca sexta*: involvement of a cadherin in the entomopathogenicity of *Bacillus thuringiensis*. Insect Biochem. Molec. Biol. 32, 1025-1036.

Francis, B. R. Bulla, L. A., Jr, 1997. Further characterization of BT-R$_1$, the cadherin-like receptor for Cry1Ab toxin in tobacco hornworm (*Manduca sexta*) midguts. Insect Biochem. Molec. Biol. 27, 541-550.

Gahan, L. J., Gould, F. Heckel, D. G., 2001. Identification of a gene associated with *B.t.* resistance in *Heliothis virescens*. Science 293, 857-860.

Gill, M. Ellar, D., 2002. Transgenic *Drosophila* reveals a functional in vivo receptor for the *Bacillus thuringiensis* toxin Cry1Ac1. Insect Mol. Biol. 11, 619-625.

Gomez, B., Miranda-Rios, J., Riudino-Pinera, E., Oltean, D. I., Gill, S. S., Bravo, A. Soberon, M., 2002. Hydropathic complementarity determines interaction of epitope (869) HITDTNNK(876) in *Manduca sexta* Bt-R(1) Receptor with loop 2 of domain II of *Bacillus thuringiensis* Cry1A toxins. J. Biol. Chem. 277, 30137-30143.

Gomez, I., Oltean, D. I., Gill, S. S., Bravo, A. Soberon, M., 2001. Mapping the epitope in cadherin-like receptors involved in *Bacillus thuringiensis* Cry1A toxin interaction using phage display. J. Biol. Chem. 276, 28906-28912.

Gomez, I., Sanchez, J., Miranda, R., Bravo, A., Soberon, M., 2002. Cadherin-like receptor binding facilitates proteolytic cleavage of helix α-1 in domain I and oligomer pre-pore formation of *Bacillus thuringiensis* Cry1Ab toxin. FEBS Lett. 513, 242-246.

Gomez, I., Dean, D. H., Bravo, A., Soberon, M., 2003. Molecular basis for *Bacillus thuringiensis* Cry1Ab toxin specificity: two structural determinants in the *Manduca sexta* Bt-R$_1$ receptor interact with loops α-8 and 2 in domain II of Cry1Ab toxin. Biochem. 42, 10482-10489.

Hara, H., Atsumi, S., Yaoi, K., Nakanishi, K., Higurashi, S., Miura, N., Tabunoki, H. Sato, R., 2003. A cadherin-like protein functions as a receptor for *Bacillus thuringiensis* Cry1Aa and Cry1Ac toxins on midgut epithelial cells of *Bombyx mori* larvae. FEBS Lett. 538, 29-34.

Hua, G., Jurat-Fuentes, J. L. Adang, M. J., 2004. Fluorescent-based assays establish *Manduca sexta* Bt-R$_{1a}$ cadherin as a receptor for multiple *Bacillus thuringiensis* toxins in *Drosophila* S2 cells. Insect Biochem. Molec. Biol. In press.

Keeton, T. P. Bulla, L. A., Jr, 1997. Ligand specificity and affinity of BT-R1, the *Bacillus thuringiensis* Cry1A toxin receptor from *Manduca sexta*, expressed in mammalian and insect cell cultures. Appl. Environ. Microbiol. 63, 3419-3425.

Laemmli, U. K., 1970. Cleavage of structural proteins during the assembly of the head of bacteriophage T4. Nature 227, 680-685.

Lee, M. K. Dean, D. H., 1996. Inconsistencies in determining *Bacillus thuringiensis* toxin binding sites relationship by comparing competition assays with ligand blotting. Biochem. Biophys. Res. Comm. 220, 575-580.

Liu, Y. B., Tabashnik, B. E., Moar, W. J. Smith, R. A., 1998. Synergism between *Bacillus thuringiensis* spores and toxins against resistant and susceptible diamondback moths (*Plutella xylostella*). Appl. Environ. Microbiol. 64, 1385-1389.

Luo, K., Banks, D. Adang, M. J., 1999. Toxicity, binding and permeability analyses of four *Bacillus thuringiensis* Cry1δ-endotoxins by use of brush border membrane vesicles of *Spodoptera exigua* and *Spodoptera frugiperda*. Appl. Environ. Microbiol. 65, 457-464.

Masson, L., Lu, Y.-j., Mazza, A., Brosseau, R. Adang, M. J., 1995. The Cry1A(c) receptor purified from *Manduca sexta* displays multiple specificities. J. Biol. Chem. 270, 20309-20315.

Masson, L., Prefontaine, G., Peloquin, L., Lau, P. C. Brousseau, R., 1990. Comparative analysis of the individual protoxin components in P1 crystals of *Bacillus thuringiensis* subsp. kurstaki isolates NRD-12 and HD-1. Biochem. J. 269, 507-512.

Morin, S., Biggs, R. W., Sisteron, M. S., Shriver, L., Ellers-Kirk, C., Higginson, D., Holley, D., Gahan, L. J., Heckel, D. G., Carriere, Y., Dennehy, T. J., Brown, J. K. Tabashnik, B. E., 2003. Three cadherin alleles associated with resistance to Bacillus thuringiensis in pink bollworm. Proc. Natl. Acad. Sci. U.S.A. 100, 5004-5009.

Nagamatsu, Y., Koike, T., Sasaki, K., Yoshimoto, A. Furukawa, Y., 1999. The cadherin-like protein is essential to specificity determination and cytotoxic action of the Bacillus thuringiensis insecticidal Cry1Aa toxin. FEBS Lett. 460, 385-390.

Nagamatsu, Y., Toda, S., Yamaguchi, F., Ogo, M., Kogure, M., Nakamura, M., Shibata, Y. Katsumoto, T., 1998. Identification of Bombyx mori midgut receptor for Bacillus thuringiensis insecticidal Cry1A(a) toxin. Biosci. Biotechnol. Biochem. 62, 718-726.

Rajagopal, R., Sivakumar, S., Agrawal, N., Malhotra, P. Bhatjagar, R. K., 2002. Silencing of midgut aminopeptidase N of Spodoptera litura by dsRNA establishes its role as B.t. toxin receptor. J. Biol. Chem. 277, 46849-46851.

Sangadala, S., Azadi, P., Carlson, R. Adang, M. J., 2001. Carbohydrate analyses of Manduca sexta aminopeptidase N, co-purifying neutral lipids and their functional interaction with Bacillus thuringiensis Cry1Ac toxin. Insect Biochem. Molec. Biol. 32, 97-107.

Sangadala, S., Walters, F., English, L. H. Adang, M. J., 1994. A mixture of Manduca sexta aminopeptidase and alkaline phosphatase enhances Bacillus thuringiensis insecticidal Cry1A(c) toxin binding and $^{86}$Rb+-K+ leakage in vitro. J. Biol. Chem. 269, 10088-10092.

Simpson, R. M. Newcomb, R. D., 2000. Binding of Bacillus thuringiensis δ-endotoxins Cry1Ac and Cry1Ba to a 120-kDa aminopeptidase-N of Epiphyas postvittana purified from both brush border membrane vesicles and baculovirus-infected Sf9 cells. Insect Biochem. Molec. Biol 30, 1069-1078.

Tabashnik, B., 1992. Evaluation of synergism among Bacillus thuringiensis toxins. Appl. Environ. Microbiol. 58, 3343-3346.

Tsuda, Y., Nakatani, F., Hashimoto, K., Ikawa, S., Matsura, C., Fukada, T., Sugimoto, K. Himeno, M., 2003. Cytotoxic activity of Bacillus thuringiensis Cry proteins on mammalian cells transfected with cadherin-like Cry receptor gene of Bombyx mori (silkworm). Biochem. J. 369, 697-703.

Vadlamudi, R. K., Ji, T. H. Bulla, L. A., Jr., 1993. A specific binding protein from Manduca sexta for the insecticidal toxin of Bacillus thuringiensis subsp. berliner. J. Biol. Chem. 268, 12334-12340.

Vadlamudi, R. K., Weber, E., Ji, I., Ji, T. H. Bulla, L. A., Jr., 1995. Cloning and expression of a receptor for an insecticidal toxin of Bacillus thuringiensis. J. Biol. Chem. 270, 5490-5494.

Wolfersberger, M. G., Luthy, P., Maurer, A., Parenti, P., Sacchi, V. F., Giordana, B. Hanozet, G. M., 1987. Preparation and partial characterization of amino acid transporting brush border membrane vesicles from the larval midgut of the cabbage butterfly (Pieris brassicae). Comp. Biochem. Physiol. 86A, 301-308.

---

The invention claimed is:

1. A method of inhibiting an insect wherein said method comprises providing a peptide to said insect for ingestion, wherein said peptide comprises SEQ ID NO:2 (CR12-MPED).

2. The method of claim 1, wherein said peptide is sprayed on to a plant.

3. The method of claim 1, wherein said method further comprises providing a *Bacillus thuringiensis* Cry protein to said insect for ingestion.

4. The method of claim 3, wherein said peptide is sprayed on to a plant that produces said protein.

5. The method of claim 3, wherein said peptide and said protein are sprayed on to a plant.

6. The method of claim 3, wherein said peptide and said protein are produced by and are present in a plant.

7. A method of inhibiting an insect, wherein said method comprises providing a peptide to said insect for ingestion, wherein said peptide has toxin activity against said insect, wherein said peptide is a fragment of an insect cadherin ectodomain comprising a *Bacillus thuringiensis* crystal protein binding domain, and wherein said peptide has at least 95% amino acid identity with SEQ ID NO:2.

8. The method of claim 7, wherein said peptide is sprayed on to a plant.

9. The method of claim 7, wherein said method further comprises providing a *Bacillus thuringiensis* Cry protein to said insect for ingestion.

10. The method of claim 9, wherein said protein toxin is a *Bacillus thuringiensis* Cry protein.

11. The method of claim 9, wherein said peptide is sprayed on to a plant that produces said protein toxin.

12. The method of claim 9, wherein said peptide and said protein toxin are sprayed on to a plant.

13. The method of claim 9, wherein said peptide and said protein toxin are produced by and are present in a plant.

14. A method of inhibiting an insect, wherein said method comprises providing a peptide to said insect for ingestion, wherein said peptide comprises an amino acid sequence having at least 95% identity with amino acid residues 1363 to 1464 of Bt-R1a, said residues corresponding to residues 1 to 100 of SEQ ID:2, and wherein said peptide binds a *Bacillus thuringiensis* Cry protein.

15. The method of claim 14, wherein said peptide comprises amino acid residues 1363 to 1464 of Bt-R1a, said residues corresponding to residues 1 to 100 of SEQ ID NO:2.

* * * * *